US012018253B2

(12) United States Patent
Bell et al.

(10) Patent No.: US 12,018,253 B2
(45) Date of Patent: Jun. 25, 2024

(54) METHOD OF DETECTING POLYCOMB REPRESSIVE COMPLEX ACTIVITY

(71) Applicant: IMBA—INSTITUT FÜR MOLEKULARE BIOTECHNOLOGIE GMBH, Vienna (AT)

(72) Inventors: Oliver Bell, Malibu, CA (US); Hagar Moussa, Vienna (AT); Ramesh Yelagandula, Vienna (AT)

(73) Assignee: IMBA—INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 1221 days.

(21) Appl. No.: 16/495,677

(22) PCT Filed: Mar. 23, 2018

(86) PCT No.: PCT/EP2018/057390
§ 371 (c)(1),
(2) Date: Sep. 19, 2019

(87) PCT Pub. No.: WO2018/172500
PCT Pub. Date: Sep. 27, 2018

(65) Prior Publication Data
US 2020/0095575 A1 Mar. 26, 2020

(30) Foreign Application Priority Data
Mar. 23, 2017 (EP) ..................... 17162519

(51) Int. Cl.
C12N 15/85 (2006.01)
C12N 15/10 (2006.01)
G01N 33/50 (2006.01)

(52) U.S. Cl.
CPC ......... *C12N 15/1086* (2013.01); *C12N 15/85* (2013.01); *G01N 33/5023* (2013.01); *C12N 2015/859* (2013.01); *C12N 2800/107* (2013.01); *C12N 2800/24* (2013.01); *C12N 2840/002* (2013.01); *C12N 2840/005* (2013.01); *C12N 2840/105* (2013.01); *C12N 2840/85* (2013.01)

(58) Field of Classification Search
None
See application file for complete search history.

(56) References Cited

FOREIGN PATENT DOCUMENTS

WO 2013/188406 A1 12/2013

OTHER PUBLICATIONS

Denisenko and Bomsztyk. Molecular and Cellular Biology 17(8):4707-4717, 1997 (Year: 1997).*
Chiang et al. BMC Molecular Biology 7:16. https://bmcmolbiol.biomedcentral.com/articles/10.1186/1471-2199-7-16. pp. 1-18, 2006 (Year: 2006).*
Roseman et al. Genetics 158(1):291-307, 2001 (Year: 2001).*
Poux et al. Development 128:75-85, 2001 (Year: 2001).*
Muller. The EMBO journal 14(6): 1209-1220, 1995 (Year: 1995).*
Yeh et al. PNAS 92:7036-7040, 1995 (Year: 1995).*
Markstein et al PNAS 111(12):4530-4535, 2014 (Year: 2014).*
Extended European Search Report from European Patent Application No. 17162519.7, mailed Sep. 13, 2017.
International Search Report from International Patent Application No. PCT/EP2018/057390, mailed May 9, 2018.
Anton et al., "Visualization of Specific DNA Sequences in Living Mouse Embryonic Stem Cells with a Programmable Fluorescent CRISPR/Cas System", Nucleus (2014), 5(2), pp. 163-172.
Banaszynski et al., "Characterization of the FKBP-Rapamycin-FRB Ternary Complex", Journal of the American Chemical Society (2005), 127(13), pp. 4715-4721.
Béguelin et al., "EZH2 is Required for Germinal Center Formation and Somatic EZH2 Mutations Promote Lymphoid Transformation", Cancer Cell (2013), 23(5), pp. 677-692.
Blackledge et al., "Variant PRC1 Complex-Dependent H2A Ubiquitylation Drives PRC2 Recruitment and Polycomb Domain Formation", Cell (2014), 157(6), pp. 1445-1459.
Chen et al., "Imaging Genomic Elements in Living Cells Using CRISPR/Cas9", Methods in Enzymology (2014), vol. 546, pp. 337-354.
Cooper et al., "Jarid2 Binds Mono-Ubiquitylated H2A Lysine 119 to Mediate Crosstalk Between Polycomb Complexes PRC1 and PRC2", Nature Communications (2016), vol. 7, pp. 1-8.
Deng et al., "CASFISH: CRISPR/Cas9-Mediated in situ Labeling of Genomic Loci in Fixed Cells", PNAS (2015), 112(38), pp. 11870-11875.
Elling et al., "Forward and Reverse Genetics through Derivation of Haploid Mouse Embryonic Stem Cells", Cell Stem Cell (2011), 9(6), pp. 563-574.
Fagerlund et al., "The Cpf1 CRISPR-Cas Protein Expands Genome-Editing Tools", Genome Biology (2015), 16(251), pp. 1-3.
Hansen et al., "A Model for Transmission of the H3K27me3 Epigenetic Mark", Nature Cell Biology (2008), 10(11), pp. 1291-1300 (Plus Supplementary Information, 10 pages).
Hathaway et al., "Dynamics and Memory of Heterochromatin in Living Cells", Cell. (2012), 149(7), pp. 1447-1460.
Hopp et al., "A Short Polypeptide Marker Sequence Useful for Recombinant Protein Identification and Purification", Bio/Technology (1988), 6(10), pp. 1204-1210.

(Continued)

*Primary Examiner* — Marcia S Noble
(74) *Attorney, Agent, or Firm* — Greer, Burns & Crain, Ltd

(57) ABSTRACT

A method of detecting Polycomb Repressive Complex (PRC) activity in a cell providing a cell with a DNA having a protein binding site and at least one reporter gene expression site is operatively connected to the protein binding site, and with a DNA containing a recombinant gene of a binding protein, the binding protein being capable of binding to the protein binding site, wherein the binding protein is fused to a member of the PRC, the method including the step of expressing the recombinant gene, letting the fused binding protein bind to the protein binding site and detecting at least one reporter gene expression.

25 Claims, 33 Drawing Sheets

Specification includes a Sequence Listing.

(56) References Cited

OTHER PUBLICATIONS

Jin et al., "The Protein Phosphatase-1 (PP1) Regulator, Nuclear Inhibitor of PP1 (NIPP1), Interacts with the Polycomb Group Protein, Embryonic Ectoderm Development (EED), and Functions as a Transcriptional Repressor", Journal of Biological Chemistry (2003), 278(33), pp. 30677-30685.

Lienert et al., "Identification of Genetic Elements that Autonomously Determine DNA Methylation States", Nature Genetics (2011), 43(11), pp. 1091-1097.

Lohr et al., "Discovery and Prioritization of Somatic Mutations in Diffuse Large B-Cell Lymphoma (DLBCL) by Whole-Exome Sequencing", PNAS (2012), 109(10), pp. 3879-3884.

Lutz-Freyermuth et al., "Quantitative Determination that One of Two Potential RNA-Binding Domains of the A Protein Component of the U1 Small Nuclear Ribonucleoprotein Complex Binds with High Affinity to Stem-Loop II of U1 RNA", Proceedings of the National Academy of Sciences (1990), 87(16), pp. 6393-6397.

Martin et al., "GAP Domains Responsible for Ras p21-Dependent Inhibition of Muscarinic Atrial K+ Channel Currents", Science (1992), 255(5041), pp. 192-194.

McCabe et al., "EZH2 Inhibition as a Therapeutic Strategy for Lymphoma with EZH2-Activating Mutations", Nature (2012), 492(7427), pp. 108-112.

Morin et al., "Somatic Mutation of EZH2 (Y641) in Follicular and Diffuse Large B-Cell Lymphomas of Germinal Center Origin", Nature Genetics (2010), 42(2), pp. 181-185.

Roy et al., "The Transcriptional Repression by NIPP1 is Mediated by Polycomb Group Proteins", Biochemica et Biophysica Acta (2007), 1769(9-10), pp. 541-545.

Skinner et al., "Use of Glu-Glu-Phe C-Terminal Epitope for Rapid Purification of the Catalytic Domain of Normal and Mutant ras GTPase-Activating Proteins", The Journal of Biological Chemistry (1991), 266(22), pp. 14163-14166.

Stuckey et al., "A Cellular Chemical Probe Targeting the Chromodomains of Polycomb Repressive Complex 1", Nature Chemical Biology (2016), 12(3), pp. 180-187.

* cited by examiner

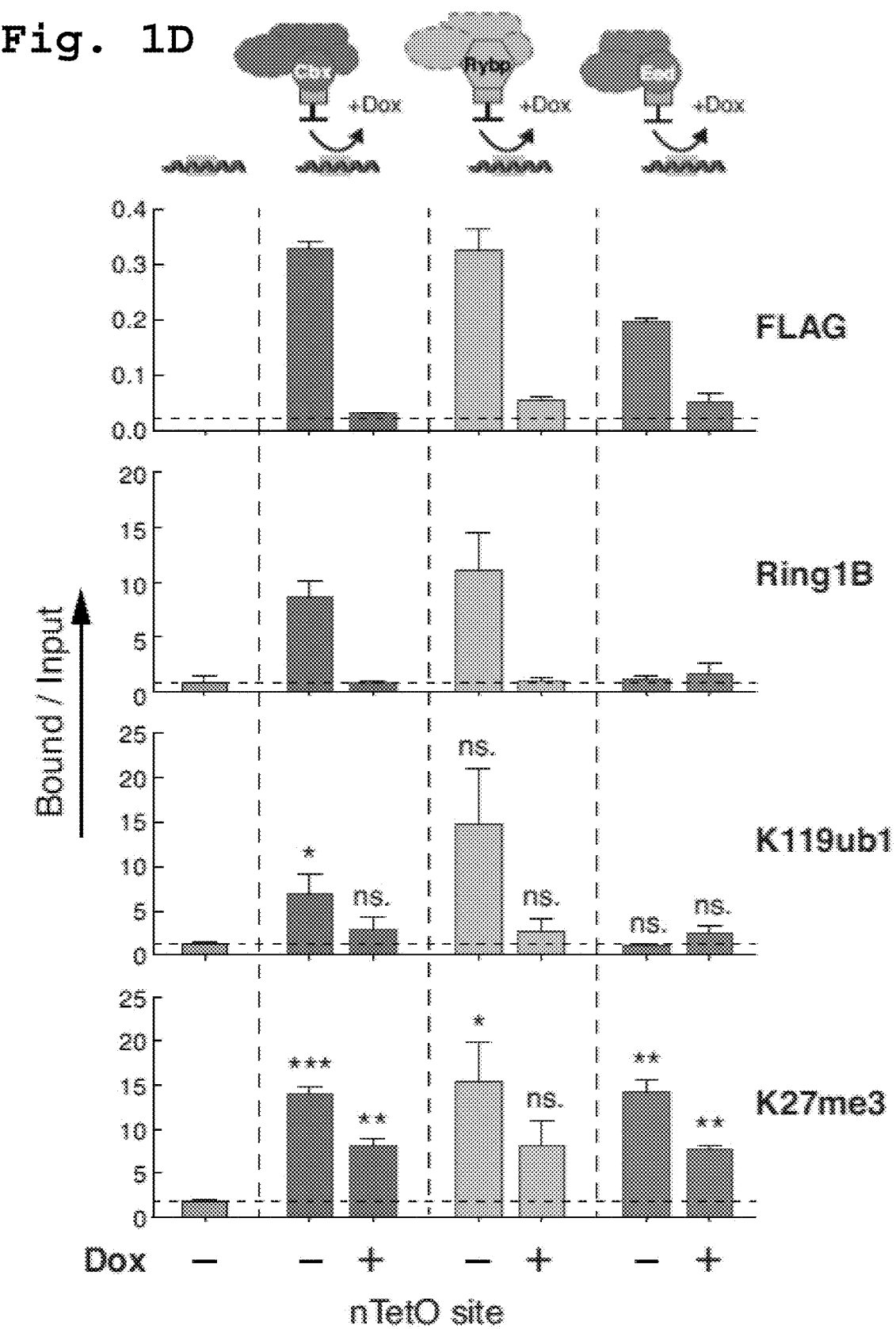

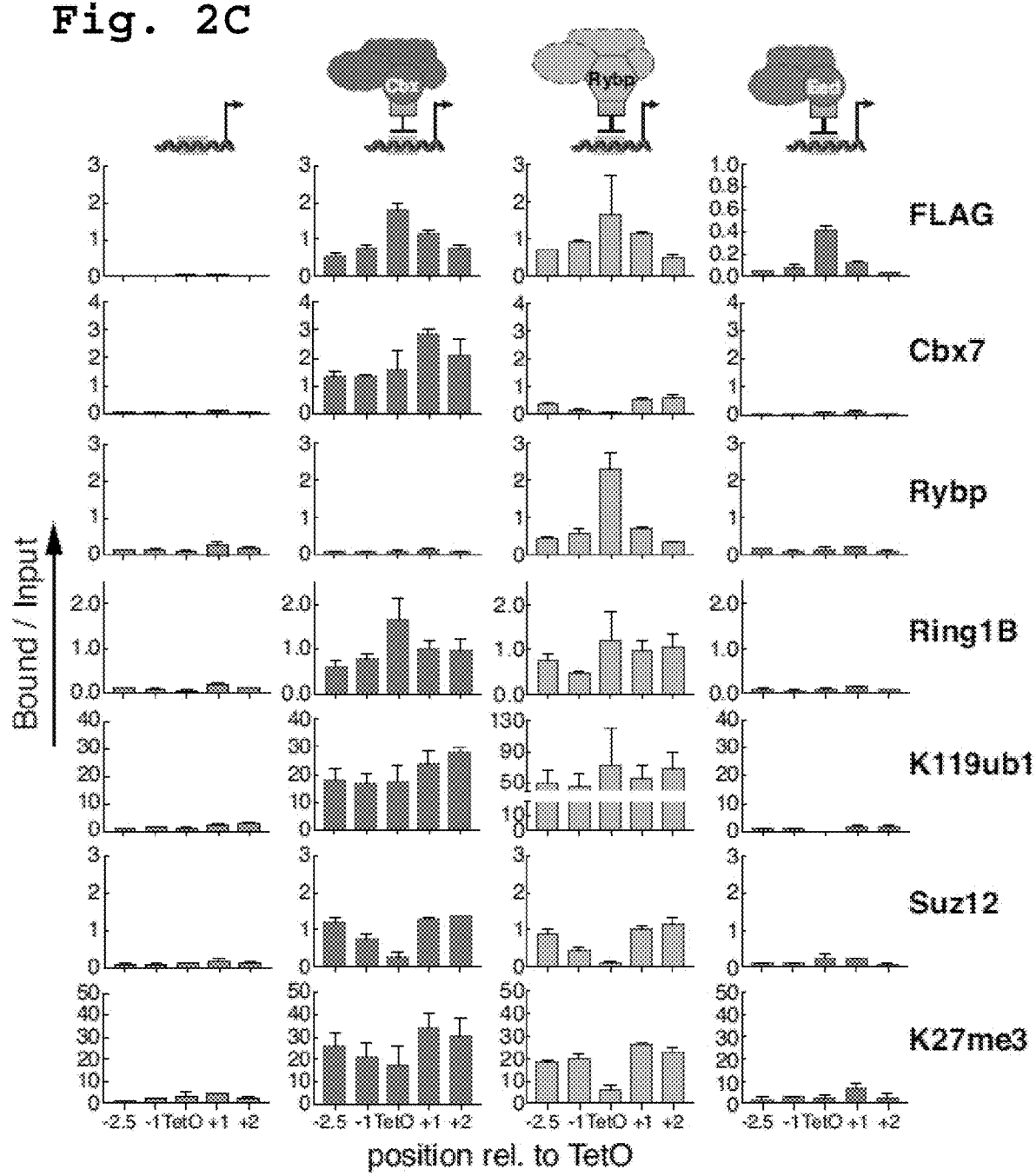

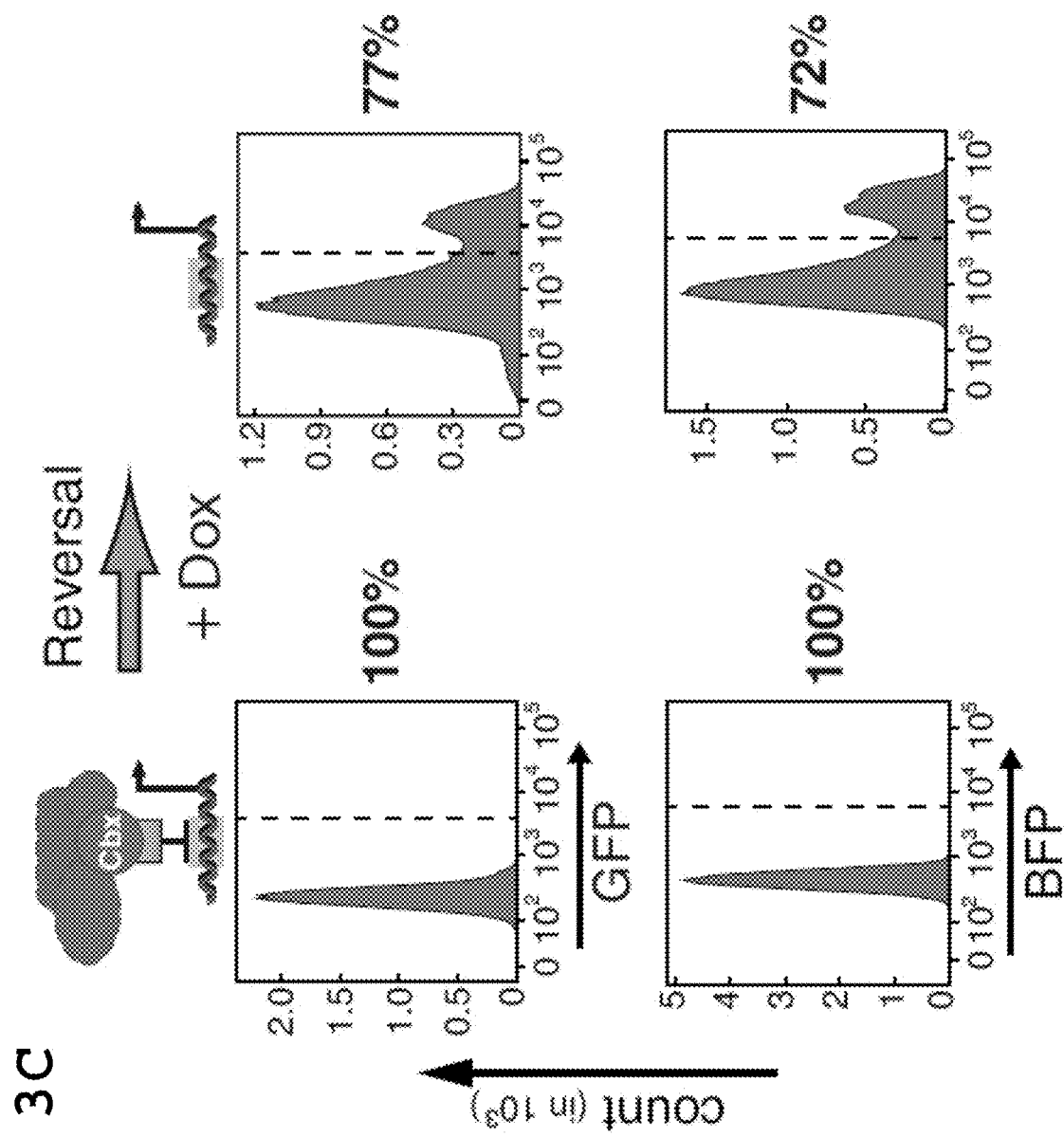

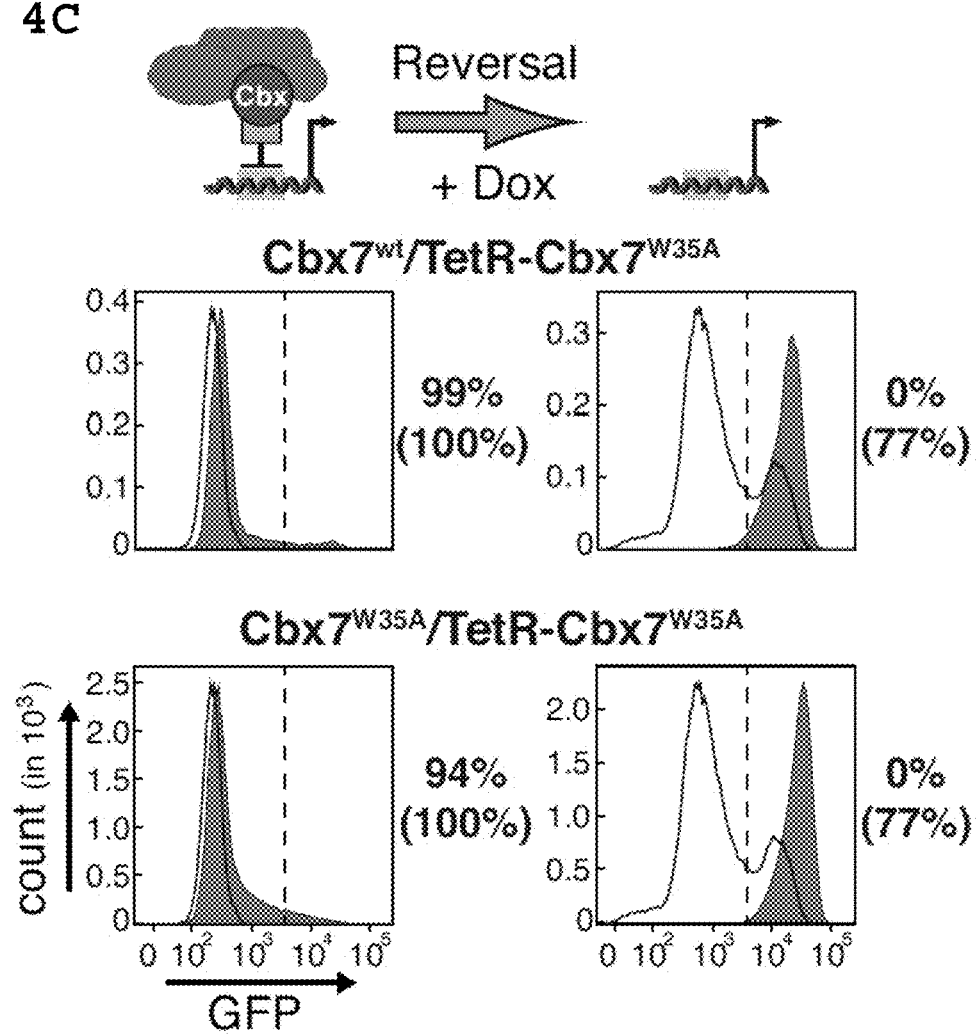

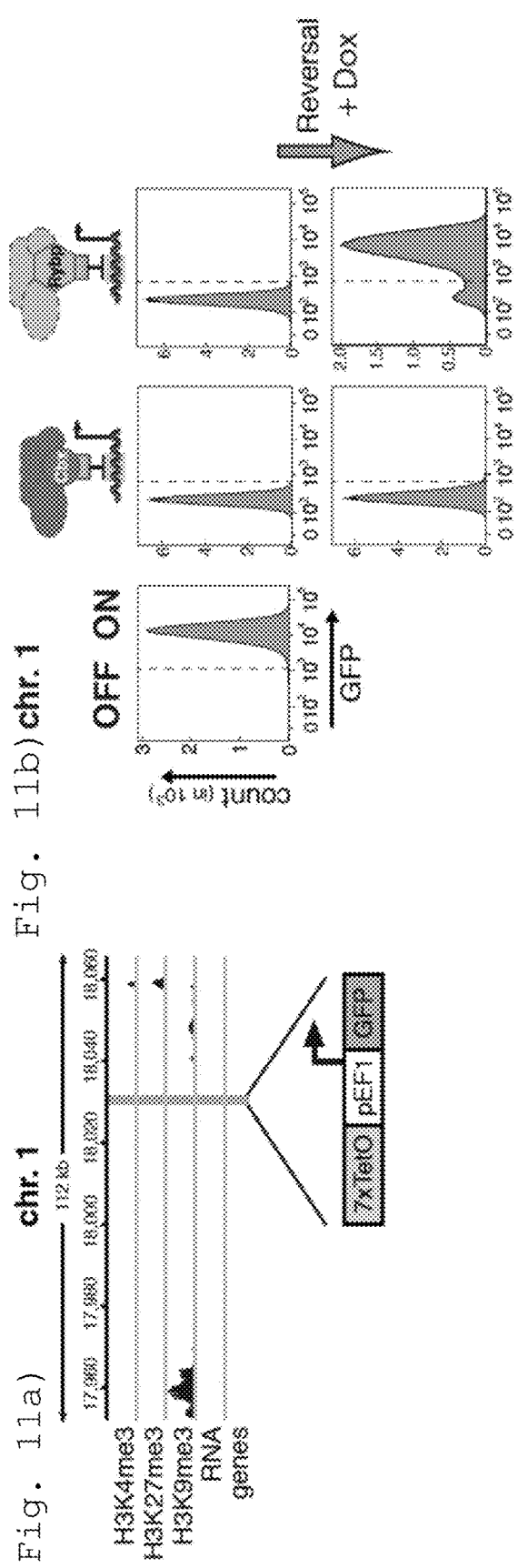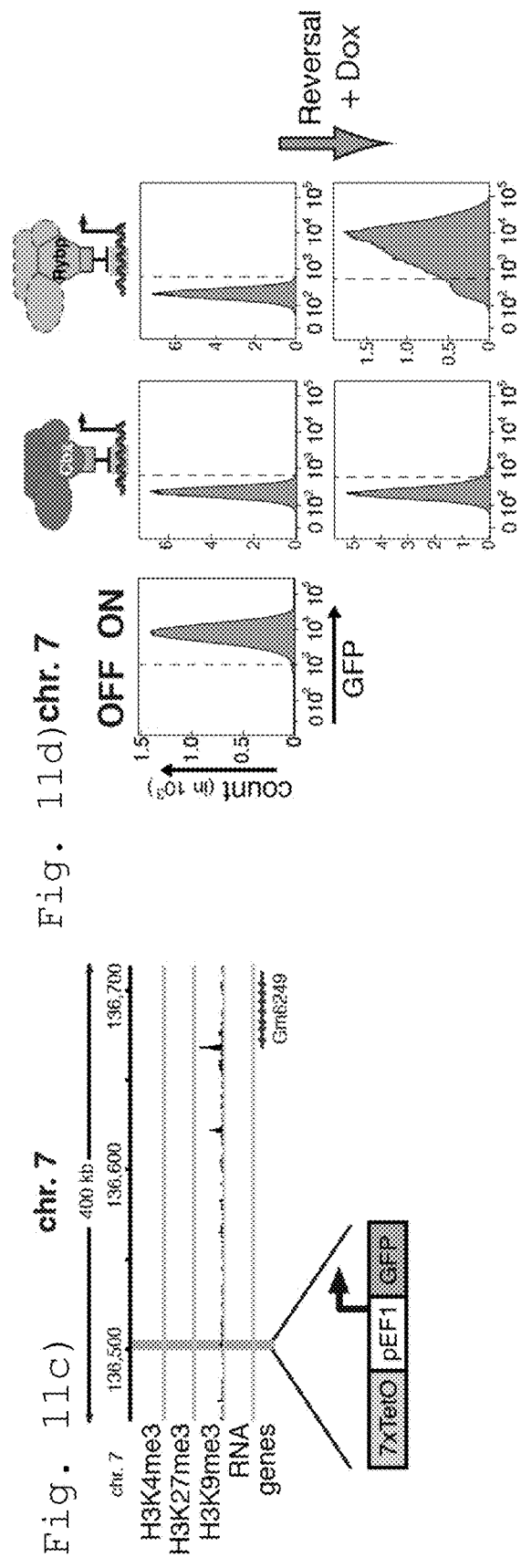

Figure 12D:
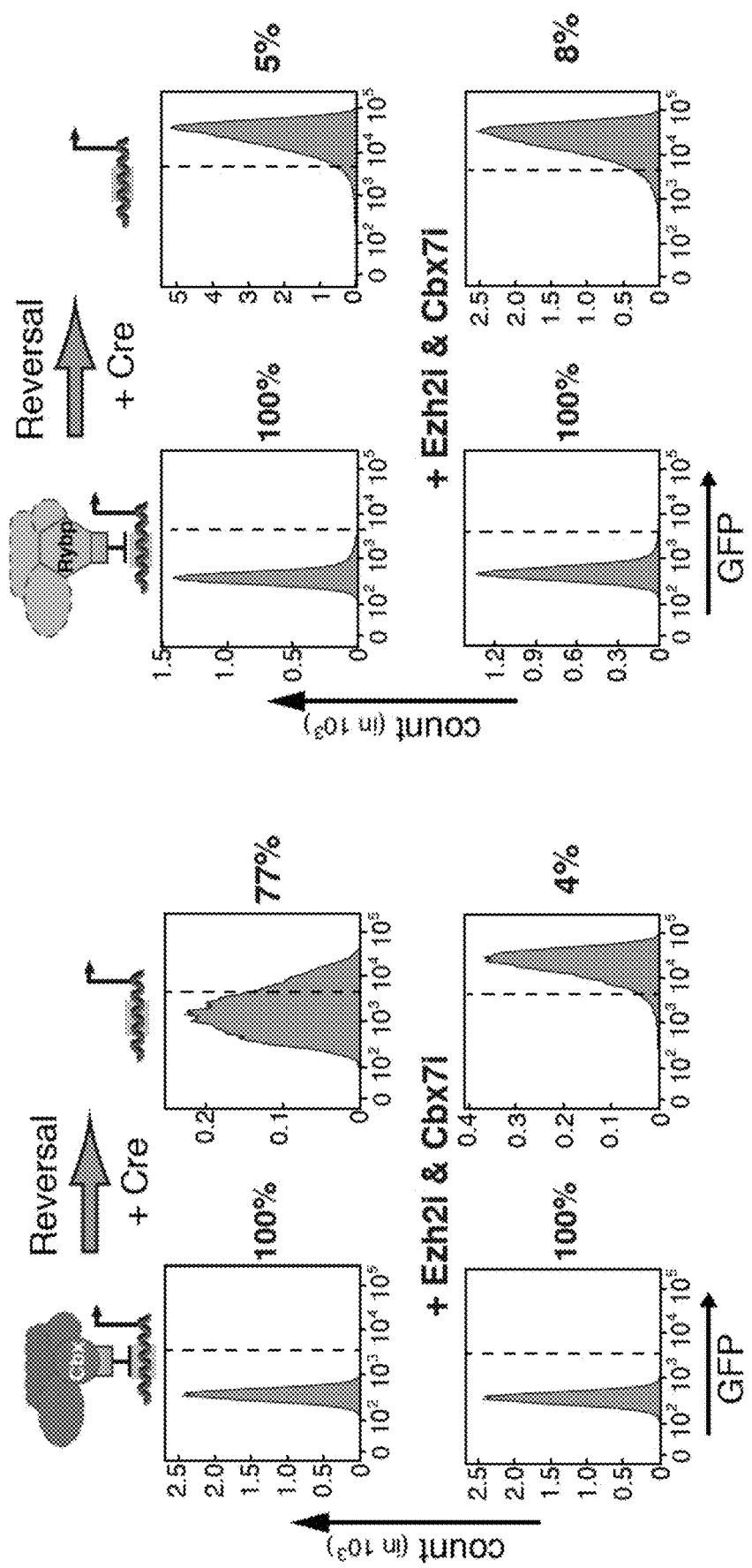
Figure 12F:
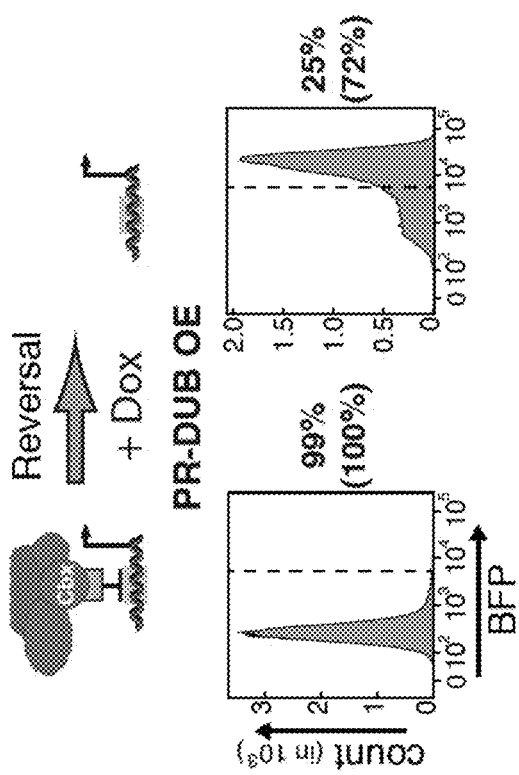

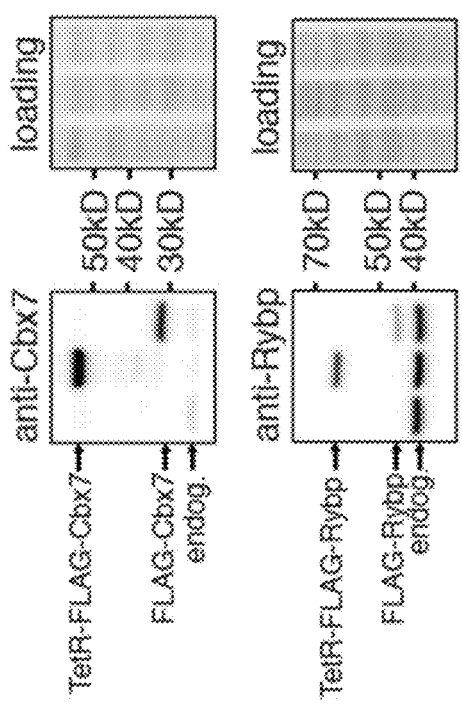
Fig. 12c)
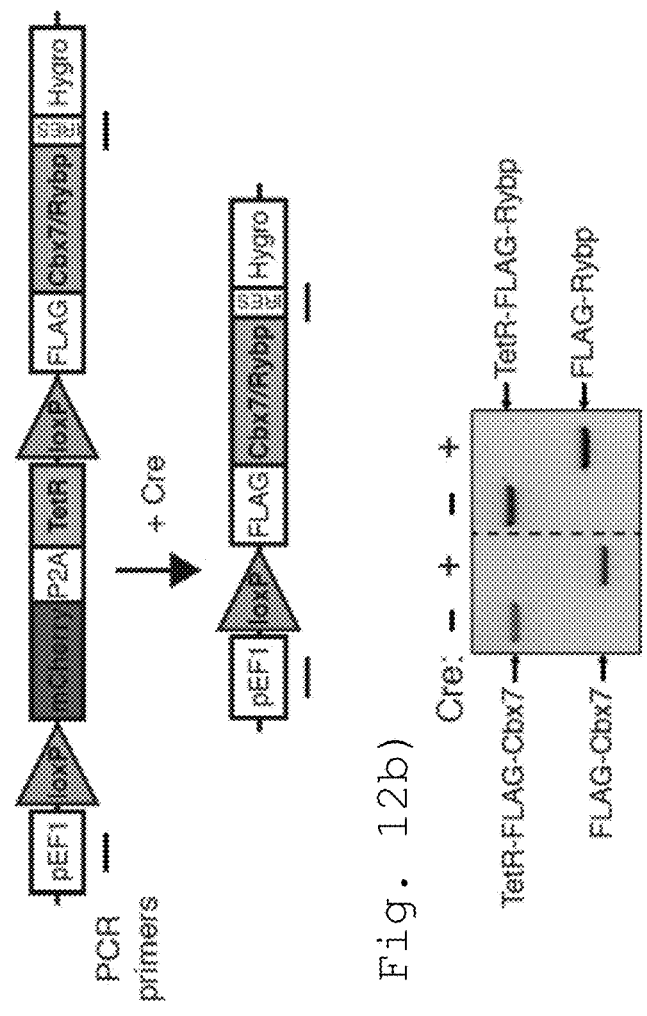
Fig. 12a)
Fig. 12b)

Examples for reporter gene expression at near active genes marked with H3K4me3

SEQUENCE LISTING

<160> NUMBER OF SEQ ID NOS: 4

<210> SEQ ID NO 1
<211> LENGTH: 44
<212> TYPE: DNA
<213> ORGANISM: Homo sapiens

<400> SEQUENCE: 1
ggcaaagttg aatatctggt gaagtggaaa ggagctcccc ccaa                44

```
<210> SEQ ID NO 2
<211> LENGTH: 14
<212> TYPE: PRT
<213> ORGANISM: Homo sapiens

<400> SEQUENCE: 2

Gly Lys Val Glu Tyr Leu Val Lys Trp Lys Gly Ala Pro Pro
1               5                   10

<210> SEQ ID NO 3
<211> LENGTH: 44
<212> TYPE: DNA
<213> ORGANISM: Artificial Sequence
<220> FEATURE:
<223> OTHER INFORMATION: Produced in a laboratory

<400> SEQUENCE: 3
ggcaaagttg aatatctggt gaagtggaaa ggatggcccc ccaa              44

<210> SEQ ID NO 4
<211> LENGTH: 14
<212> TYPE: PRT
<213> ORGANISM: Artificial Sequence
<220> FEATURE:
<223> OTHER INFORMATION: Produced in a laboratory

<400> SEQUENCE: 4

Gly Lys Val Glu Tyr Leu Val Lys Trp Lys Gly Trp Pro Pro
1               5                   10
```

METHOD OF DETECTING POLYCOMB REPRESSIVE COMPLEX ACTIVITY

INCORPORATION OF SEQUENCE LISTING

This application contains a Sequence Listing file named "1CM3744.txt" of 2 KB in size and which was submitted to the USPTO electronically on May 2, 2023. The sequence listing contained in the 1CM3744.txt file is part of the specification and is hereby incorporated by reference herein in its entirety.

The invention relates to the field of protein-protein or protein-DNA interaction monitoring, e.g. for the screening of chemical agents for their ability to interfere in catalytic activity, protein-protein or protein-DNA interaction.

BACKGROUND

Epigenetic mechanisms support heritable transmission of differential gene expression patterns, stabilizing diverse cell types in metazoans. Silencing of key developmental genes by Polycomb group (PcG) proteins is arguably the premier paradigm for epigenetic regulation of cell fate inheritance. PcG proteins assemble into distinct multi-subunit complexes with inherent catalytic and non-catalytic activities. Among the two major families, Polycomb Repressive Complex 1 (PRC1) catalyzes monoubiquitiniation of lysine 119 on histone H2A (H2AK119ub1) and has the capacity to condense nucleosomes in vitro whereas PRC2 is responsible for di- and trimethylation of lysine 27 of histone H3 (H3K27me2/3). While these activities are intimately linked to forming and maintaining repressive chromatin domains, the molecular underpinnings of epigenetic repression remain poorly understood.

In vertebrates, the PRC1 family has diversified into many heterogeneous complexes that can be broadly classified by the presence or absence of Cbx (chromobox-containing protein) subunits. In canonical PRC1 (cPRC1), Cbx confers the ability to bind H3K27me3. This interaction is critical for cPRC1 recruitment to PRC2 target genes and transcriptional silencing. Moreover, mitotic transmission of H3K27me3 has been linked to inheritance of Polycomb chromatin domains after genome replication. In contrast, variant PRC1 complexes, which harbour Rybp (Ring1B and Yy1 binding protein), or its homolog Yaf2, are recruited to chromatin independently of H3K27me3. Exclusively, vPRC1 targets are only moderately repressed, suggesting distinct modes of transcriptional regulation compared to the concerted action of canonical PRC1 and PRC2. A method of monitoring chromatin changes, in particular by determining effects of HP1alpha recruitment on H3K9me3, is disclosed in WO 2013/188406. Blackledge et al. (*Cell.* 157, 1445-1459 (2014)) have shown that by ectopic tethering different PRC1 complexes have diverse catalytic activities but the impacts of their modifications on gene expression and epigenetic inheritance was still not known. How the different PcG complexes and their chromatin modifying activities achieve and transmit heritable gene silencing remains unresolved.

Development of cancer is frequently caused by genetic mutations resulting in aberrant gene regulation and/or function. Sequential acquisition of mutations may lead to the constitutive activation of proto-oncogenes and the loss of function of tumor suppressor genes that in summary drive cancer development. It has become increasingly evident that tumor development also involves epigenetic changes. These epigenetic changes include both genome-wide losses and regional gains of DNA methylation, as well as altered patterns of histone modification. Deregulation of PRC1 and PRC2 have been implicated in tumorigenesis. Canonical PRC1 subunits Cbx7 and Bmi1 and the catalytic subunit of PRC2 are thought to be oncogenic and their overexpression directly correlates with the invasive potential of a variety of cancers. E.g. PRC2 can abnormally repress DAB2-interacting protein (a tumor necrosis factor), leading to cancer. Further evidence for direct roles of PcG-dependent chromatin modifications in cancer includes loss-of-function mutations of the H3K27 demethylase UTX and the recent discoveries of somatic mutations of lysine 27 in H3.3 in pediatric glioblastoma. As consequence targeted interference PcG activity has emerged a major strategy to control tumorigenesis. Indeed, several chemical probes targeting PRC1 and PRC2 activities are currently in clinical trials for potential cancer medication.

Hansen et. al. (Nature Cell Biology 10(11) (2008): 1291-1300) describes a reporter system to determine histone methylation maintenance during DNA replication. The transcriptional reporter is randomly integrated, both quantitively and qualitatively. For reporter experiments, a cell was selected with high luciferase activity, which indicates many integrations at active euchromatin sites.

Roy et al. (Biochimica et Biophysica acta 1769 (9-10) (2007): 541-545) employed a reporter assay involving transient transduction of two vectors; one expressing the Gal4 fusion protein and another one comprising of five DNA binding sites for Gal4 upstream of a luciferase reporter gene.

Similarly, Jin et al. (Journal of Biological Chemistry 278 (33) (2003): 30677-30685) described a reporter assay with transient expression of Gal4 fusions and transient presentation of the reporter plasmid comprising five GAL4 DNA-binding sites, a SV40 promoter controlling the luciferase reporter gene.

It is a goal of the present invention to provide insight into complex interactions and to provide means to manipulate PRC function, especially for cancer medicament development and monitoring PRC activity. In particular, the invention has the goal of providing improved reporter systems with higher sensitivity to determine PRC function and facilitate high-throughput screening to identify genetic and pharmacologic modulators.

SUMMARY

The present invention provides a method of detecting Polycomb Repressive Complex (PRC) activity in a cell. The cell contains a DNA with a protein binding site and at least one reporter gene (at a reporter gene expression site) operatively connected to the protein binding site. In some embodiments, the protein binding site is integrated in the genome. In addition, the cell expresses a recombinant gene of a binding protein, said binding protein being capable of binding to said protein binding site, fused to a member of the PRC; said method comprising the steps of expressing said recombinant gene, letting said fused binding protein bind to said protein binding site and detecting at least one reporter gene expression.

The said method entails reversible recruitment of selective PRC activities which facilitates discriminating initiation of repressive chromatin modifications and gene silencing from epigenetic inheritance of repressive chromatin and gene silencing.

The invention further provides a kit comprising a1) a cell with a DNA having a protein binding site and at least one reporter gene expression site is operatively connected to said protein binding site or a2) a DNA vector having a protein binding site and at least one reporter gene expression site is operatively connected to said protein binding site; said kit further comprises b) a DNA vector with a recombinant gene of a binding protein, said binding protein being capable of binding to said protein binding site, wherein said binding protein is fused to a member of a Polycomb Repressive Complex (PRC).

Even further provided is a cell comprising a DNA having a protein binding site and at least one reporter gene expression site is operatively connected to said protein binding site, and further comprising a DNA comprising a recombinant gene of a binding protein, said binding protein being capable of binding to said protein binding site, wherein said binding protein is fused to a member of a Polycomb Repressive Complex (PRC).

All embodiments of the invention are described together in the following detailed description and all preferred embodiments relate to all embodiments, aspects, methods, DNA constructs, cells and kits alike. E.g. descriptions of methods as such also read on the cells used in the inventive methods. Kits or their components, such as DNA constructs and cells, can be used in or be suitable for inventive methods. Any component used in the described methods can be in the kit. Preferred and detailed descriptions of the inventive methods read alike on suitability and resulting cells of the inventions. All embodiments can be combined with each other, except where explicitly stated.

DETAILED DESCRIPTION

According to the invention, a PRC, in particular PRC1 and PRC2, were reversibly tethered to an artificial DNA site, i.e. an ectopic target site, operatively linked to a transcriptional reporter gene. Changes in reporter gene expression indicates Polycomb Repressive Complex (PRC) activity. The measurement is performed in an isolated cell or cell culture, e.g. a plurality of cells, e.g. in vitro. The following description of "a cell" or "the cells" of course reads on all cells modified according to the invention to be used in the inventive methods or kits. The cell has a DNA having a protein binding site and at least one reporter gene expression site is operatively connected to said protein binding site. The cell also has a DNA comprising a recombinant gene of a binding protein, said binding protein being capable of binding to said protein binding site. Both DNA may have been introduced into the cell by a vector. Usually, either DNA or both DNAs are integrated into the genome of the cells. In some embodiments, the DNA may be on different DNA molecules as long as expression of the above proteins is allowed, e.g. on an expression vector. The binding protein is fused or joined or tethered to a member of the PRC. The recombinant gene is expressed in the cell, thereby letting said fused binding protein bind to said protein binding site. At least one reporter gene expression is then detected or monitored. Detection or monitoring can be for any signal that the reporter gene expression exhibits.

In detail, the main concept in this method is that the PRC member is bound to a DNA in the vicinity of the reporter gene, an ectopic site. The PRC member determines assembly of a specific, functionally active PRC at the ectopic site. Different modes of assembly for the individual PRCs exist, while PRC1 assembles to a bound or tethered PRC1 member, PRC2 can also be recruited as a consequence of PRC1-dependent chromatin modification, eg. H2AK119ub1. In turn, the now active PRC will act on the reporter gene, most effectively on its promoter, by posttranslational modification of histones (eg. methylation or ubiquitination) or non-catalytic chromatin modifications (nucleosome compaction) thereby preventing expression of the reporter gene. PRC-mediated modification of chromatin in proximity to the promoter may lead to an inhibited expression of the reporter gene by e.g. preventing unwinding of the DNA portion required for reporter gene expression. The detection of suppressed reporter gene expression informs on the activity of the PRC. Accordingly, the reporter expression or changes in reporter expression are determined according to the inventive method in response to PRC activity, including PRC assembly or PRC catalytic activity. Different tethered PRC members can be determined for their ability to assemble an active PRC. Furthermore, chemical compounds or modified cellular culturing conditions can be investigated for their ability to affect, e.g. interfere, in PRC activity.

By selecting a PCR member to be bound (also referred to as "tethered") to the protein binding site on the DNA (indirectly via a binding protein), determines the type or types of PRC to be assembled. Some PRC members are selective for a particular PRC, other members are ubiquitous in two or more PRCs. For example Cbx7 (chromobox homolog 7) is a selective member of canonical PRC1, Rybp (RING1 and YY1-binding protein) is a selective member of variant PRC1 and Eed (embryonic ectoderm development protein) is a selective member of PRC2. Any of these members can be bound. Members shared by PRCs are members of the PCGF (Polycomb-group RING finger), e.g. PCGF 1, 2, 3, 4, 5, 6, and Ring1A (E3 ubiquitin-protein ligase RING1) or Ring1B (RNF2 or E3 ubiquitin-protein ligase RING2). The PRC member can also be a member of Polycomb repressive deubiquitinase (PR-DUB). In preferred embodiments of the inventive method, kit or cell the PRC is selected from variant or non-canonical PRC1 (vPRC1), canonical PRC1 (cPRC1) and PRC2. The PRC can be selective for one of vPRC1, cPRC1 and PRC2, i.e. a PRC member only found in vPRC1, cPRC1 or PRC2 is bound, or non-selective, i.e. a PRC member found in at least two PRCs (e.g. in both vPRC1 and cPRC1) is bound. One of the following PRC2 members may be used: EED (embryonic ectoderm development), EZH1 (enhancer of zeste 1 polycomb repressive complex 2 subunit), EZH2 (enhancer of zeste 2 polycomb repressive complex 2 subunit), RBBP4 (RB binding protein 4, chromatin remodeling factor), RBBP7 (RB binding protein 7, chromatin remodeling factor), SUZ12 (suppressor of zeste 12), JARID2 (Jumonji/ARID domain-containing protein 2), AEBP (Adipocyte enhancer-binding protein 2), Epop (Elongin BC and Polycomb repressive complex 2-associated protein).

One of the following PRC1 members may be used: CBX (Chromobox family), e.g. CBX 2, 4, 6, 7 or 8; PHC1 (Polyhomeotic-like protein 1), PHC2 (Polyhomeotic-like protein 2), PHC3 (Polyhomeotic-like protein 3), Ring1A, Ring1B, PCGF1 (aka Nervous system Polycomb-1), PCGF2 (aka Mel18), PCGF3, PCGF4 (aka Bmi1), PCGF5, PCGF6 (aka MBLR), AUTS2 (Autism susceptibility gene 2 protein), BCL-6 (B-cell lymphoma 6 protein). One of the following PR-DUB members may be used: ASXL1 (Additional sex combs-like protein 1), ASXL2 (Additional sex combs-like protein 2), BAP1 (BRCA1-associated protein 1) and OGT1 (UDP-N-acetylglucosamine-peptide N-acetylglucosaminyltransferase 110 kDa subunit).

In addition, recruitment of PRC1 or PRC2 members with known cancer mutations facilitates selective compound screening. E.g. aberrant EZH2 with point mutations in the SET domains conferring catalytic hyperactivity will provide a specific handle to selectively model mutant EZH2-containing complexes described in diffuse large B cell lymphoma and follicular lymphoma (Beguelin et al. (2013). EZH2 is required for germinal center formation and somatic EZH2 mutations promote lymphoid transformation. Cancer Cell 23, 677-692; Morin et al. (2010). Somatic mutations altering EZH2 (Tyr641) in follicular and diffuse large B-cell lymphomas of germinal-center origin. Nat. Genet. 42, 181-185; Lohr et al. (2012). Discovery and prioritization of somatic mutations in diffuse large B-cell lymphoma (DLBCL) by whole-exome sequencing. Proc. Natl. Acad. Sci. USA 109, 3879-3884; McCabe et al. (2012b). EZH2 inhibition as a therapeutic strategy for lymphoma with EZH2-activating mutations. Nature 492, 108-112.) Preferred members of the PRC that is bound or fused to the binding protein are Cbx7, Rybp, Eed, Ring1a, Ring1b, or PCGF1 through 6.

Individual PRCs may have different effects on chromatin structure and the maintenance of such a modification. For example PRC1 recruitment (or assembly) initiates transcriptional repression and Polycomb-dependent chromatin modifications, including PRC2-mediated histone H3K27me3. However, unlike variant PRC1, canonical PRC1 (cPRC1) also maintains silencing upon release from the target DNA. It was found that the Cbx7 subunit of cPRC1 interacts with H3K27me3, promoting a cPRC1-PRC2 feedback loop that enables inheritance of repression after loss of the initial stimulus. Thus, distinct PRC1 complexes in vertebrates can differentially regulate epigenetic maintenance of gene silencing potentially enabling dynamic responses to complex stimuli.

Reversible tethering of PRC activities facilitates discriminating initiation from epigenetic maintenance of chromatin modifications and gene repression. Hence upon reversal of PRC member tethering, the inventive method provides an opportunity to selectively study perturbations of epigenetic maintenance for example by chemical compound interference.

The reporter gene expression site operatively connected to the protein binding site (whereto the PRC member is indirectly bound to via the binding protein). "Operatively connected" means that the site is functionally associated for histone modifications at the reporter gene by the PRC that is assembled to the bound PRC member. This histone modification leads to a detectable signal, including a reduction of the signal, by the reporter gene. This connection requires special vicinity, which can be determined easily for a given cell by standard assays. Spatial vicinity preferably means that the reporter gene expression site is within a distance of 12 kb (kilo bases, i.e. 1000 bases) in length from said protein binding site. The reporter gene expression site may be located upstream or downstream of the protein binding site. Further preferred distances are within a distance of 10 kb, of 8 kb or of 6 kb, in length from said protein binding site. The distance is preferably to the promoter of the reporter gene, which is strongly affected by histone modification. Modification of a histone at the coding region of the reporter gene may be less effective since a DNA polymerase may have an intrinsic ability to unwind histone bound DNA, when transcription has already started.

Possible reporter genes include genes of e.g. fluorescent proteins, preferably GFP (green fluorescent protein), enhanced green fluorescent protein (eGFP), d2EGFP, CFP (cyan fluorescent protein), YFP (yellow fluorescent protein), RFP (drFP583; also red fluorescent protein), BFP (blue fluorescent protein), smURFP (Small ultra red fluorescent protein), HcRed, DsRed, DsRed monomer, ZsGreen, AmCyan, ZsYellow enhanced blue fluorescent protein (eBFP), enhanced yellow fluorescent protein (eYFP), GFPuv, enhanced cyan fluorescent protein (eCFP), far red Reef Coral Fluorescent Protein; β-galactosidase; luciferase; a peroxidase, e.g. horse radish peroxidase; alkaline phosphatases, e.g., SEAP, and glucose oxidase, any cell surface marker such as Thy1.1.

Another type of reporter coding domain of interest that can be used in an inventive reporter gene is one that encodes an enzymatic label. "Enzymatic label" means an enzyme that converts a substrate to a detectable product. Suitable label enzymes for use in the present invention include, but are not limited to, galactosidase, horseradish peroxidase, luciferases, e.g., firefly and renilla luciferase, alkaline phosphatases, e.g., SEAP, and glucose oxidase. The presence of the label can be determined through the enzyme's catalysis of substrate into an identifiable product. Also possible are reporter compounds that may be indirectly detected, e.g. a reporter compound that is detectable as a partner of a binding pair. "Partner of a binding pair" means one of a first and a second moiety, wherein the first and the second moiety have a suitable binding affinity for each other to detect the pair with its members bound to each other. Suitable binding pairs for use in the invention include, but are not limited to, antigens/antibodies (for example, digoxigenin/antidigoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avidin (or biotin/streptavidin or biotin/neutravidin) and calmodulin binding protein (CBP)/calmodulin. Other suitable binding pairs include polypeptides such as the FLAG-peptide [Hopp et al., BioTechnology, 6:1204-1210 (1988)]; the KT3 epitope peptide [Martin et al., Science, 255:192-194 (1992)]; tubulin epitope peptide [Skinner of al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)] and the antibodies each thereto. A partner of one binding pair may also be a partner of another binding pair. For example, an antigen (first moiety) may bind to a first antibody (second moiety) which may, in turn, be an antigen for a second antibody (third moiety). It will be further appreciated that such a circumstance allows indirect binding of a first moiety and a third moiety via an intermediary second moiety that is a binding pair partner to each. As will be appreciated by those in the art, a partner of a binding pair may comprise a label, as described above. It will be further appreciated that this allows for a tag to be indirectly labeled upon the binding of a binding partner comprising a label. Attaching a label to a tag which is a partner of a binding pair, as just described, is referred to herein as "indirect labeling". Any such moiety or binding partner can be used in a reporter gene of the present invention.

In addition to detecting a reporter gene expression, it is also possible to detecting a chromatin or histone modification-change, preferably of histone H3. Such methods are disclosed in WO 2013/188406.

In preferments, at least one reporter gene expression sites comprise one, two or more reporter gene expression sites, preferably only one or—if two or more—of different reporter genes. Each of them is operatively connected to the binding site as said above, e.g. within the above mentioned distances. This pair of at least one reporter gene and the operatively connected binding site is also referred to as a "construct" herein, which is preferably integrated into the genome of the cells, in particular by only one integration into the genome of said cell. More than one reporter gene expression site can be used to create different signals (if different reporter gene expression sites are used). More than one reporter genes can be used to analyze the different effect of the PRC at different distances from the protein binding site, especially the dynamics and extent of chromatin modification spreading can be investigated by different reporter genes at different distances from the protein binding site. To distinguish such different effects, preferably different reporter genes are used at different distances. Different distances are e.g. a quarter, a third, half, two thirds or three quarters of the distance of the protein binding site to the reporter gene with the longer distance, or any range in between these fractions. Thus, for example, in a preferred embodiment of the present invention a first of said two or more expression sites is within a distance from said protein binding site that is less than two thirds the distance of a second of said two or more expression sites. According to another example, a first of said two or more expression sites is within a distance from said protein binding site that is less than three quarters but greater than one quarter the distance of a second of said two or more expression sites. If two or more reporter gene expression sites are used, preferably at least one is downstream and at least another one is upstream of the protein binding site.

The protein binding site is preferably integrated into the genome at a transcriptionally neutral locus or region, e.g. within a region that lacks genes and regulatory elements such as promoters or enhancers and lacks active and repressive histone modifications. Transcriptional neutral means that the construct there (most importantly the reporter gene) does not receive significant activation or repression from the neighboring locus or region. "Transcriptionally neutral locus or region" refers to the naive site before integration of a construct. The inventive construct can of course result in expression of the reporter gene independent thereon. Preferably there is a single copy of the protein binding site-reporter gene construct per different reporter gene in a cell. Such single reporter genes per cell prevent mixed signals or e.g. differently regulated reporters, such as with one reporter signalling activation the other signalling inactivation. These measures (transcriptionally neutral locus and single copy)—both independently but especially preferred together—result in vastly increased sensitivity of the method as shown in example 9.

Preferably the transcriptionally neutral locus or region lacks any native genomic gene expression promoter and/or repressor within 10000 nt in distance, preferably within 30000 nt in distance, especially preferred within 50000 nt or more in distance, from the ends of the inventive construct comprising the protein binding site and the reporter gene, that would be able to act on the reporter gene. "Native" genomic gene expression promoter refers to any other promoter found in the cell apart from the inventive construct comprising the reporter gene expression site, which of course may comprise a promoter.

Preferably, the transcriptionally neutral locus or region lacks active and repressive histone modifications within 10000 nt in distance, preferably within 30000 nt in distance, especially preferred within 50000 nt or more in distance, from the ends of the inventive construct comprising the protein binding site and the reporter gene. An example active (or activating) histone modification is H3K4 methylation. Example repressive histone modifications are H3K27 methylation and H3K9 methylation. Histone K methylation can be a trimethylation (H3K4me3, H3K9me3, H3K27me3). The negative impact of these methylations has been shown in FIGS. 13 and 14, wherein the distinction between the active and repressed states dependent on to PRC activity loses discriminative quality.

Lacking active and repressive histone methylation shall not be understood in an absolute sense but refers to significant difference to normal methylation background. Active and repressive histone methylation shall be understood as a methylation so that gene expression activation or repression occurs due to histone methylation. In particular active histone methylation shall refer to an activating methylation of 20% or less, preferably 10% or less, or 5% or less, activating methylation as in transcriptionally active euchromatin in said cell. In particular, repressive histone methylation shall refer to a repressive methylation of 20% or less, preferably 10% or less, or 5% or less repressive methylation as in transcriptionally repressed heterochromatin in said cell. Of course, for said comparison said cell is capable of such methylation at wild-type levels. This absent or non-significant methylation shall again be in the nearby region at the integration site as said above (within 10000 nt in distance, preferably within 30000 nt in distance, especially preferred within 50000 nt or more in distance)

It is also preferred to avoid methylation peaks within the nearby region (within 10000 nt in distance, preferably within 30000 nt in distance, especially preferred within 50000 nt or more in distance). Accordingly, preferably said locus or region, has no 100 nt long sub-region ("peak") with more than 30%, preferably with more than 20% even more preferred with more than 10%, of a methylation of a 100 nt sub-region ("peak"), which is the maximally methylated 100 nt sub-region in euchromatin (for activating methylation) or heterochromatin (for repressive methylation).

The transcriptionally neutral locus or region is preferably located distal to heterochromatin, i.e. an inactive genetic locus decorated with "repressive" histone modifications. Inactivity may be characterized by histone methylation, such as H3K27me3, H3K9me3 or any combination thereof. Such histone methylation should preferably be avoided within 10000 nt in distance, preferably within 30000 nt or more in distance, especially preferred within 50000 nt or more in distance, from the ends of the inventive construct comprising the protein binding site and the reporter gene.

Insertions into the genome can be site directed or random. In case of random insertions, a specific selection of the desired insertion is needed. Site-directed integration is preferred. Accordingly, the genomic histone methylation status and absence of gene promoters and/or repressors can be verified before integrations. Promoters and repressors can usually be avoided by selecting a genetic locus without any nearby gene annotations. "Nearby", as above, preferably means within 10000 nt in distance, preferably within 30000 nt in distance, especially preferred within 50000 nt or more in distance. Site-directed insertions into the genome can be facilitated by e.g. targeted recombination, e.g. CRISPR/Cas enhanced recombination and/or integration, or Cre recombinase directed insertion (e.g. into a cell line that has an identified Cre recombinase sites at a locus of interest).

Preferably, the genome only comprises one insertion of the construct comprising the protein binding site and the reporter gene into the genome. "One insertion" refers to the entire construct. It is of course possible to have multiple copies of protein binding sites in tandem that act on the same reporter gene but increase binding efficiency of the protein binding site. Such tandem sites are e.g. close together, e.g. with at most 50 nt between the protein binding sites, preferably they are directly adjacent (0 nt between).

The inventive method can be used to one or more screen candidate compounds for its ability to interfere or modify PRC activity on the reporter gene(s). A candidate compound may interfere with PRC activity, thereby no or a reduced signal from the reporter gene(s) as result of PRC activity is observed. "Signal as result of PRC activity", as above, may mean a reduction of the reporter gene expression through histone modification (which by itself is inhibitory to gene expression).

A variety of different candidate compounds may be screened by the above methods. Candidate compounds encompass numerous chemical classes, though typically they are organic molecules, preferably small organic compounds having a molecular weight of more than 50 and less than about 2,500 daltons. Candidate compounds may comprise functional groups necessary for structural interaction with proteins. Example candidate compounds are peptides and peptide analogues. Usually, the following observations can be compared: a) normal expression of the reporter gene without PRC activity at the protein binding site; b) expression of the reporter gene with active PRC (with any PRC member being fused to the binding protein, preferably Cbx); c) expression of the reporter gene with active PRC as above but with the candidate compound. For example c) can be compared with b). B) can be compared with a). It is also possible to compare b) with b) when a different PRC is fused to the binding protein, e.g. in order to investigate PRC mechanisms. C) can be compared with c) if different candidate compounds are investigated.

The candidate compound can be an intracellular manufactured compound, such as a recombinant protein; or it can be extracellularly administered to the cell. Any compound, in particular small organic molecules, e.g. molecules up to a size of 5 kDa can be administered. The extracellular administration is preferred because also the cells capacity for uptake is included in the mechanism for signal generation by the reporter gene(s). Accordingly potential pharmaceutical compounds, e.g. for cancer treatment can be investigated. Preferably, the cell is contacted with a candidate compound and the step of detecting at least one reporter gene expression (c) is compared with such detection in a cell without being contacted by the candidate compound (especially b).

Compounds known to interfere with PRC activity are UNC3866 (Stuckey et al., Nature Chemical Biology. 12, 180-187 (2016), GSK126 (McCabe et al. EZH2 inhibition as a therapeutic strategy for lymphoma with EZH2-activating mutations. *Nature* 492, 108-112 (2012)). Compounds can also be used in a comparison between two different compounds, e.g. a comparison c) to c).

The inventive method can also be used to screen one or more gene hyperactivation, gene suppressions or gene mutations for its ability to interfere or modify PRC activity on the reporter gene(s). Such a genetic modification (hyperactivation, suppression, mutation) can be introduced into a cell parallel to the inventive modification with the introduced PRC reporter. Any changes in PRC repression in comparison to the repression without the mutation can be monitored to determine the mutation's effect on the PRC.

A further preferred embodiment of the inventive method, combinable with all other embodiments, is based on single cell measurements. Generally, in an assay a plurality of cells can be used and a signal is obtained from said combined cells. On the other hand, preferably single cell signals are recorded to determine PRC activity/repression in single cells. Single cells measurements can be facilitated by known methods, such as flow cytometry (especially fluorescence-activated cell sorting, FACS) or handling single cells.

The present invention provides several means to increase signal sensitivity to distinguish an activated PRC and a non-active PRC via the reporter gene. Sensitivity can be increased by only one binding site-reporter gene construct integration into the genome to avoid mixed signals that would occur with multiple insertions. Another method is single cell measurements to avoid mixed signals of several cells (wherein in different cells different activation of the PRC can occur, leading to mixed signals). A further method variation is using well-placed integration of the protein binding site/construct at a transcriptionally neutral locus or region of the genome of the cell in order to avoid genomic activating or repressing effects on the reporter gene. Any of these means can be selected to increase sensitivity. Of course, these means can be combined, as is preferred.

A particular goal of the invention is to provide a screening assay for high-throughput screening, e.g. for compound or genetic screening as described above. High-throughput screening usually required a high signal sensitivity to allow automated processes a distinction between the PRC-active and PRC-inactive states. Preferably the sensitivity is shown by a signal intensity difference between the PRC-active and PRC-inactive states by a factor of at least 10, preferably at least 50.

High-throughput screening is usually performed in parallel. Preferably, 10 or more different cells are screened in parallel.

A further mode to investigate reporter gene signals is in altered PRC activity at the protein binding site. By artificial induction PRC can be inactivated or disassembled or dislocated from the protein binding site. In particular, binding protein binding to the protein binding site can be inducible or disruptable. This allows control of reversible binding of the binding protein to the protein binding site. For example, the protein binding site can be an inducible binding site, preferably wherein the induction of binding is mediated by the presence of a binding cofactor or a binding disruptor. A binding cofactor is e.g. cofactor that allows binding of at least two linker molecules. Such a cofactor can be a dimerizer that mediates dimerization of at least two polypeptides, which act as linker molecules. Upon binding of the dimerizer, the at least two polypeptides bind to form a di- or multimer. At first the linker molecules/polypeptides binds the DNA at the protein binding site. Another linker molecule/polypeptide, that is a binding partner to the first linker molecule/polypeptide, binds to a member of the PRC. Such a dimerizer is e.g. rapamycin and the polypeptides are e.g. FKBP12 and FRB that form a heterodimer with rapamycin (Banaszynski et al., J. Am. Chem. Soc. 2005, 127, 4715-4721).

A binding disrupter can be a molecule that inhibits binding of the binding protein to DNA at the protein binding site or that dissociates two linker molecules. Of the two linker molecules, as above, a linker molecule can bind the DNA (at the protein binding site) or is bound to a binding protein and another linker molecule is bound to the member of the PRC. Introduction of the binding disrupter prevents or disrupts binding of the linker molecules that would otherwise bind to each other. An example binding disrupter is a tetracycline including their analogues, such as doxycycline. Tetracyclines, analogues or doxycycline act in the Tet-Off and Tet-On system, which are forms of an inducible expression system, that can be used according to the invention as system for inducible DNA binding of the binding protein to the DNA at the protein binding site. In a Tet-Off system or Tet-On system, the DNA binding protein is a TetR (tetracycline repressor) and the protein binding site is one or more TetO site(s). Preferably an array of TetO sites is used of e.g. 2, 3, 4, 5, 6, 7, 8, 9 or 10 or more TetO sites in functional proximity so that each TetO site may act upon the at least one reporter gene expression. Thus, in preferred embodiments of the invention, the inducible binding site is a TetO site, preferably wherein the binding disruptor is a tetracycline, especially doxycycline. The binding protein is preferably a Tet repressor or tetracycline transactivator (tTA) protein.

Preferably, the inventive method uses a reversible binding of the binding protein to the protein binding site, e.g. by control of such an inducer or disrupter. Preferably the reporter is determined in a binding and a non-binding configuration. Preferably, the binding configuration is followed by a non-binding configuration. This allows detection of persisting effects on silencing of the reporter. The inventive kits and cells may have DNA constructs for such a switch between binding configurations. The kit preferably also comprises an inducer or disrupter. By reversing the tethering it is possible to measure the epigenetic nature of PRC-mediated chromatin modifications. E.g. hit-and-run epigenetic mutations, such as DNA methylation or aberrant chromatin modifications, can be epigenetically manifested leading to disease. Such mutations and PCR behavior can be detected according to the invention.

Another possible protein binding site is a zinc finger binding site, e.g. a ZFHD1 binding site. In this case, the binding protein comprises a zinc finger motif capable of binding to said zinc finger binding site. Further examples are a LexA DNA binding site, a transcription factor DNA binding site, a Group H nuclear receptor member DNA binding site, a steroid/thyroid hormone nuclear receptor superfamily member DNA binding site, a bacterial LacZ DNA binding site, etc. A further protein binding site may comprise an Upstream Activating Sequence (UAS). UAS is known from the Gal4-UAS system. In this case, the binding protein comprises Gal4 capable of binding to said UAS. Furthermore, PRC members may be recruited using DNA binding protein of the CRISPR-Cas system. In this case a PRC member is fused to catalytic dead versions of Cas9, Cas9 orthologues or Cpf1 (Fagerlund et al., *Genome Biology* 2015 16:251), e.g. dCas9, as binding protein. The DNA binding protein of the CRISPR-Cas system targets assembly of the PRC through expression of a guide RNA specific for a DNA sequence (referred to as "protein binding site" herein, now a site that is bound by Cas9, or its orthologue, in guide RNA dependence) in proximity of the reporter gene. Thus the CRISPR-Cas system allows guided DNA binding via its guide RNA sequence (Deng et al., PNAS 2015, 112(38): 11870-11875; Chen et al. Methods in Enzymology, 2014, 546:337; Anton et al., Nucleus 2014, 5(2):163-172).

Consequently, a further observation that can be compared with the above a), b) or c) observations is d) expression of the reporter gene with activatable PRC that is disrupted or lacks a required induced binding (also referred to as non-induced binding or non-induction) of the binding protein to the DNA binding site (if the PRC requires induction to be active), so that the PRC member is not indirectly bound to the protein binding site. In the above a), b) and c), the indirect binding of the PRC member to the protein binding site takes place and the PRC assembles, if not interrupted by a candidate compound. Preferably, detecting at least one reporter gene expression is compared between induction and non-induction of the binding site. This also includes detecting at least one reporter gene expression when comparing between non-disruption and disruption of the binding site. Preferred disruption methods are disruptors of protein to DNA binding, such as via the TetO method as described above, or a linker dissociation method. Such a comparison allows switching binding or active PRC formation from on (active) to off (inactive, not bound) or from off to on. This is particularly favorable since this switch can happen inside the cell without altering the conditions, except of course the introduction of the inducer or disrupter, so that undisturbed measurements can be performed, which in turn allows improved comparison between the on and off states. Thus, it is preferred to perform induces/non-disrupted detection of the at least one reporter gene in a cell and then perform the non-induced/disrupted detection of the at least one reporter gene expression in a cell, in particular in the same cell. A particular advantage of the measurements in the same cell allows monitoring of persistence or maintenance of histone modifications in a switch on to off system (first induced/non-disrupted then non-induced/disrupted). Histone modification from the "on" case may persist and thereby continue a reduction of reporter gene expression in the "off" phase. In other embodiments, histone modification will not persist. Histone modification is detected through the detection of reporter gene expression as detailed herein. This behavior is dependent on the recruited PRC. In particular PRC2 recruitment will lead to persistence. The invention can be used to distinguish persistence behaviors after an on-to-off switch dependent on individual bound or tethered PRC members. It is particular preferred to test a change in persistence behavior under the influence of a candidate compound, e.g. persistence behavior is detected with and without a candidate compound.

Preferably the binding protein fused to the member of the PRC is stably expressed, in particular constitutively expressed. A strong expression may be desired for sufficient supply of binding protein and of the fused PRC member. This measure will increase sensitivity of the inventive method. Strong expression can for example be selected by linking the fusion protein to a marker protein or peptide, such as an optically recognizable protein or peptide (e.g. mCherry). Cells with sufficient marker allows easy monitoring of sufficient expression of the binding protein during the inventive PRC assay (e.g. unwanted silencing can be detected and excluded).

The cell may also be allowed to growth and undergo cell division. It may be of interest to reporter gene expression before and after a cell division, in particular persistence of histone modification (by detecting the reporter gene expression reduction) is determined after and before cell division. Such a detection scheme may comprise an on to off switch as detailed above, then letting the cell divide and then determining reporter gene expression after cell division.

Cells used according to the present invention are preferably insect or mammalian cells. The cells can be human cells or of a non-human animal, e.g. a rodent cells, such as a mouse, rat or hamster cell, or equine, bovine, ovine, canine, feline, non-human primate cells. The cells are usually isolated cells and can e.g. be grown or maintained in a container ex vivo, such as a vial or a well-plate. The cells may be totipotent but preferably are pluripotent, multipotent or unipotent. Pluripotency may be induced pluripotency. Ex vivo refers to outside of a living multicellular organism, such as a non-human animal or human.

A "totipotent" cell can differentiate into any cell type in the body, including the germ line following exposure to stimuli like that normally occurring in development. Accordingly, a totipotent cell may be defined as a cell being capable of growing, i.e. developing, into an entire organism.

It will be understood that the cells that are subject of the present invention are preferably not totipotent, but (strictly) pluripotent. The cell should be a living cell.

A "pluripotent" cell is not able of growing into an entire organism, but is capable of giving rise to cell types originating from all three germ layers, i.e., mesoderm, endoderm, and ectoderm, and may be capable of giving rise to all cell types of an organism.

A "multipotent" cell is capable of giving rise to at least one cell type from each of two or more different organs or tissues of an organism, wherein the said cell types may originate from the same or from different germ layers, but is not capable of giving rise to all cell types of an organism. In contrast, a "unipotent" cell is capable of differentiating to cells of only one cell lineage.

Among the various species, various types of cells may be used, such as hematopoietic, neural, glial, mesenchymal, cutaneous, mucosal, stromal, muscle (including smooth muscle cells), spleen, reticulo- endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

Cells can be used or provided in a cell culture, as a plurality of cells. In particular, the plurality of cells may comprise 10 cells to 1 Billion cells, preferably 100 cells to 100 Million cells, 1000 cells to 50 Million cells or 10000 cells to 10 Million cells, preferably about 1 Million cells. "About" refers to +/−20%. In a kit, preferably at least 25%, at least 50% or at least 75% have the inventive modification for suitability for the inventive method or comprising the specified elements.

In a further, related, aspect of the invention a kit is provided. The kit may be suitable to perform any one of the inventive methods and provides means thereto. Any kit of the invention may comprise containers to hold these means (e.g. DNA construct or cells). The kit may comprise a cell with a DNA having a protein binding site and at least one reporter gene expression sites functionally linked to said protein binding site; said kit further comprises a DNA vector with a recombinant gene of a binding protein, said binding protein being capable of binding to said protein binding site, wherein said binding protein is fused to a member of a Polycomb Repressive Complex (PRC).

A kit may also comprise a DNA vector of a DNA having a protein binding site and at least one reporter gene expression sites operatively connected to said protein binding site; said kit further comprises a DNA vector with a recombinant gene of a binding protein, said binding protein being capable of binding to said protein binding site, wherein said binding protein is fused to a member of a Polycomb Repressive Complex (PRC).

Details of said vectors and their DNA parts like binding sites and genes (reporter gene expression sites) are described above and the same applies to the kit.

The kit may be used to generate different cells suitable for the inventive methods, e.g. introducing genes for expression of different bound PRC members in order to investigate the different behavior of the cells with different PRC members and their effect on different PRC assembly and activity. Accordingly but not necessarily restricted to this use, the invention also provides a method of generating a cell usable in a method of the invention, comprising providing the inventive kit and introducing the vector(s) into the/a cell.

In addition to the above components, the inventive kits may further include (in certain embodiments) instructions for practicing the inventive method.

Also provided is a cell comprising a DNA having a protein binding site and at least one reporter gene expression sites operatively connected to said protein binding site, and further comprising a DNA comprising a recombinant gene of a binding protein, said binding protein being capable of binding to said protein binding site, wherein said binding protein is fused to a member of a Polycomb Repressive Complex (PRC).

In the inventive method, kit or cells, essentially two DNA parts are required, i) a DNA having a protein binding site and at least one reporter gene expression sites and ii) DNA comprising a recombinant gene of a binding protein. DNA i) and ii) may be the same or a different DNA molecule, e.g. when integrated into the genome on the same or different chromosomes. The location is not important but it is preferred that the reporter gene expression site has at least one, e.g. 2, 3, 4, 5, 6, 7, 8, 9, 10 or more CpG sites that can be methylated thereby increasing the reduction of expression by histone modifications.

Preferably, the invention is defined according to the following embodiments:

1. A method of detecting Polycomb Repressive Complex (PRC) activity in a cell, the method comprising the step of providing a cell with a DNA having a protein binding site and at least one reporter gene expression site that is operatively connected to said protein binding site, and with a DNA comprising a recombinant gene of a binding protein, said binding protein being capable of binding to said protein binding site, wherein said binding protein is fused to a member of the PRC, said method further comprising the steps of expressing said recombinant gene, letting said fused binding protein bind to said protein binding site and detecting at least one reporter gene expression.

2. The method of 1, wherein an operatively connected reporter gene expression site is within a distance of 12 kb in length from said protein binding site.

3. The method of 1 or 2, wherein the at least one reporter gene expression site comprises two or more of the at least one reporter gene expression sites, preferably of different reporter genes.

4. The method of 3, wherein a first of said two or more expression sites is within a distance from said protein binding site that is less than two thirds the distance of a second of said two or more expression sites.

5. The method of any one of 1 to 4, wherein the at least one reporter gene expression is selected from expression of fluorescent proteins, preferably GFP, CFP, YFP, drFP583, BFP, smURFP; β-galactosidase; luciferase; a peroxidase.

6. The method of any one of 1 to 5, wherein the cell is contacted with a candidate compound and the step of detecting at least one reporter gene expression is compared with such detection in a cell without being contacted by the candidate compound.

7. The method of any one of 1 to 6, wherein the member of the PRC that is fused to the binding protein is selected from Cbx7, Rybp, Eed, Ring1a, Ring1b, PCGF1, PCGF2, PCGF3, PCGF4, PCGF5, PCGF6.

8. The method of any one of 1 to 7, wherein the protein binding site is an inducible binding site, preferably wherein the induction of binding is mediated by the presence of a binding co-factor or a binding disruptor.

9. The method of 8, wherein detecting at least one reporter gene expression is compared between induction and non-induction of the binding site.

10. The method of 8 or 9, wherein the inducible binding site is a TetO site, preferably wherein the binding disruptor is tetracycline or doxycycline.

11. The method of any one of 1 to 7, wherein the protein binding site is a zinc finger binding site and said binding protein comprises a zinc finger motif capable of binding to said zinc finger binding site.

12. A kit comprising a1) a cell with a DNA having a protein binding site and at least one reporter gene expression site operatively connected to said protein binding site or a2) a DNA vector having a protein binding site and at least one reporter gene expression site is operatively connected to said protein binding site; said kit further comprises b) a DNA vector with a recombinant gene of a binding protein, said binding protein being capable of binding to said protein binding site, wherein said binding protein is fused to a member of a Polycomb Repressive Complex (PRC).

13. A method of generating a cell usable in a method of any one of 1 to 11, comprising providing the kit of 12 and introducing the vector b) into the cell of a1) or introducing the vectors of a2) and b) into a cell.

14. A cell comprising a DNA having a protein binding site and at least one reporter gene expression site is operatively connected to said protein binding site, and further comprising a DNA comprising a recombinant gene of a binding protein, said binding protein being capable of binding to said protein binding site, wherein said binding protein is fused to a member of a Polycomb Repressive Complex (PRC).

15. The method, kit or cell of any one of 1 to 14, wherein PRC is selected from variant PRC1, canonical PRC1 and PRC2.

The present invention is further illustrated by the following figures and examples, without necessarily being limited to these embodiments of the invention.

FIGURES

FIG. 1. Reversible PcG protein targeting establishes repressive chromatin modifications and maintenance of H3K27me3 at a transcriptionally inactive locus. A) Scheme of experimental design. TetR fusion facilitates reversible tethering of different PcG proteins to Tet Operator sites (TetO) upstream of a reporter gene and tests the consequences of chromatin modifications on transcriptional regulation. Doxycycline (Dox) addition releases TetR binding to determine heritable maintenance of chromatin modifications and expression state in the absence of the initial stimulus. B) Histone modifications and RNA expression surrounding a single naive TetO binding site (nTetO) located on chromosome 1 in mouse ES cells. C) ChIP-qPCR shows relative enrichments of TetR fusions, PcG proteins and histone modifications at nTetO and IAP, which serves as negative control. Data are mean ±SD (error bars) of three experimental replicates. D) ChIP-qPCR shows changes in relative enrichments of TetR fusions, PcG proteins and histone modifications at nTetO before and after six days of Dox treatment. Data are mean ±SD (error bars) of three experimental replicates. Statistical significance was calculated relative to no TetR fusion control (or IAP in case of FLAG) using Student t-test (P values: ≥0.05; ≤0.05 (*); ≤0.01 (); ≤0.001 (*)).

FIG. 2. Targeting of canonical and variant PRC1 establishes repressive chromatin modifications and silences reporter genes. A) Histone modifications and RNA expression surrounding the integration site of the dual reporter gene construct in mESCs expressing TetR PcG fusion proteins. B) Flow cytometry histograms of GFP expression in the absence and presence of TetR PcG fusion proteins. C) ChIP-qPCR analysis shows relative enrichments of TetR fusion, PcG proteins and histone modifications upstream and downstream of the TetO DNA binding sites (DBS). Data are mean ±SD (error bars) of three experimental replicates.

FIG. 3. Canonical but not variant PRC1 supports maintenance of repressive chromatin modifications and reporter gene silencing. A) and B) Flow cytometry histograms relate GFP expression before and after reversal of TetR PcG fusion protein binding in response to Dox treatment for six days. Percentages (%) indicate fraction of silenced cells. C) and D) ChIP qPCR analyses of compares relative enrichments of TetR fusions, PcG proteins and histone modifications before and after six days of Dox treatment. Data are mean ±SD (error bars) of three experimental replicates.

FIG. 4. Interaction of Cbx7 with H3K27me3 is essential for cPRC1-dependent maintenance of reporter gene silencing. A) Bar graph shows mean and standard deviation of the percentage of the GFP-negative cells before and after Dox six days of treatment of cPRC1-TetO mESCs from at least three independent experiments. Statistical significance was calculated relative to controls (ctrl) using Student t-test (P values: ≥0.05; ≤0.05 (*); ≤0.01 (); ≤0.001 (*); ≤0.0001 (****)). B) Percentage of GFP- and BFP-negative cells before and after six days of Dox treatment in response to increasing concentrations of Ezh2 inhibition by GSK126. C) Flow cytometry histograms compare GFP expression before and after six days of Dox treatment of wildtype (gray—upper panels) and Cbx7$^{W35}$A mutant dual reporter cells expressing TetR-Cbx7$^{W35}$A (gray—lower panels). Wildtype TetR-Cbx7 reporter cells (no fill) serve as reference. Percentages indicate fraction of silenced cells in mutant and wildtype reporter cell lines (in brackets). D) Percentage of GFP-negative cells before and after six days of Dox treatment in response to increasing concentrations of Cbx7 inhibitor (UNC3866) alone, in combination with 4 μM GSK126 or control compound (UNC4219). E) GFP histograms before and after six days of Dox addition to TetR-Cbx7 reporter cells with overexpression of Bap1 and Asx11 (PR-DUB OE), components of the human PR-DUB complex specific for H2AK119ub1. Wildtype TetR-Cbx7 reporter cells (no fill) serve as reference. Percentages indicate fraction of silenced cells in PR-DUB OE and wildtype reporter cell lines (in brackets). F) Model of the regulation of canonical and variant PRC1 complexes in relation to PRC2. CPRC1 and PRC2 engage in a reciprocal feedback mechanism to promote sequence-independent epigenetic gene silencing. Arrows indicate catalytic activity of different PcG complexes. Dashed arrows indicate signalling function of histone modifications. Stop bars highlight antagonistic effects.

FIG. 5. Ectopic expression of TetR fusion proteins does not disrupt normal Polycomb regulation and cell proliferation. A) Immuno blots showing expression levels of TetR fusion proteins relative to endogenous Cbx7, Rybp and Eed. Ponceau membrave staining serves as loading controls. B) ChIP qPCR analyses of PcG proteins and histone modifications in the absence and presence of TetR fusion proteins at the Evx2 promoter (positive control) and at IAP (negative control). Data are mean ±SD (error bars) of three experimental replicates. C) Growth curves of parental TetO-mESCs, cPRC1-TetO-, vPRC1-TetO- and PRC2-TetO-mESCs. Doubling times were determined based on two independent cell count measurements in 24 hour intervals as indicated.

Figure 6A:
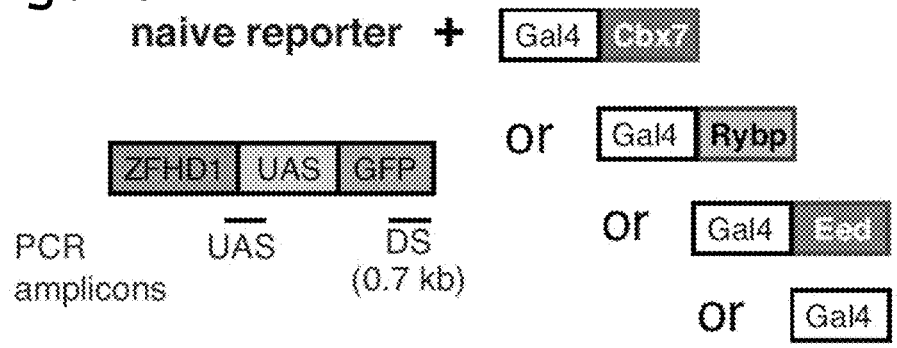
Figure 6B:
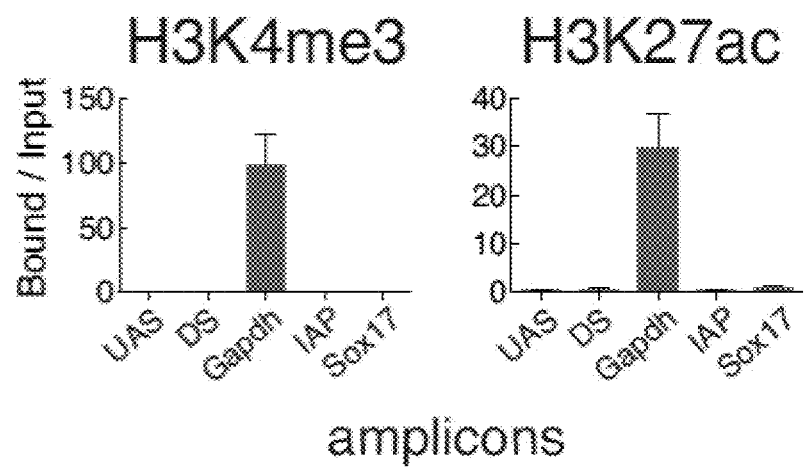
Figure 6C:
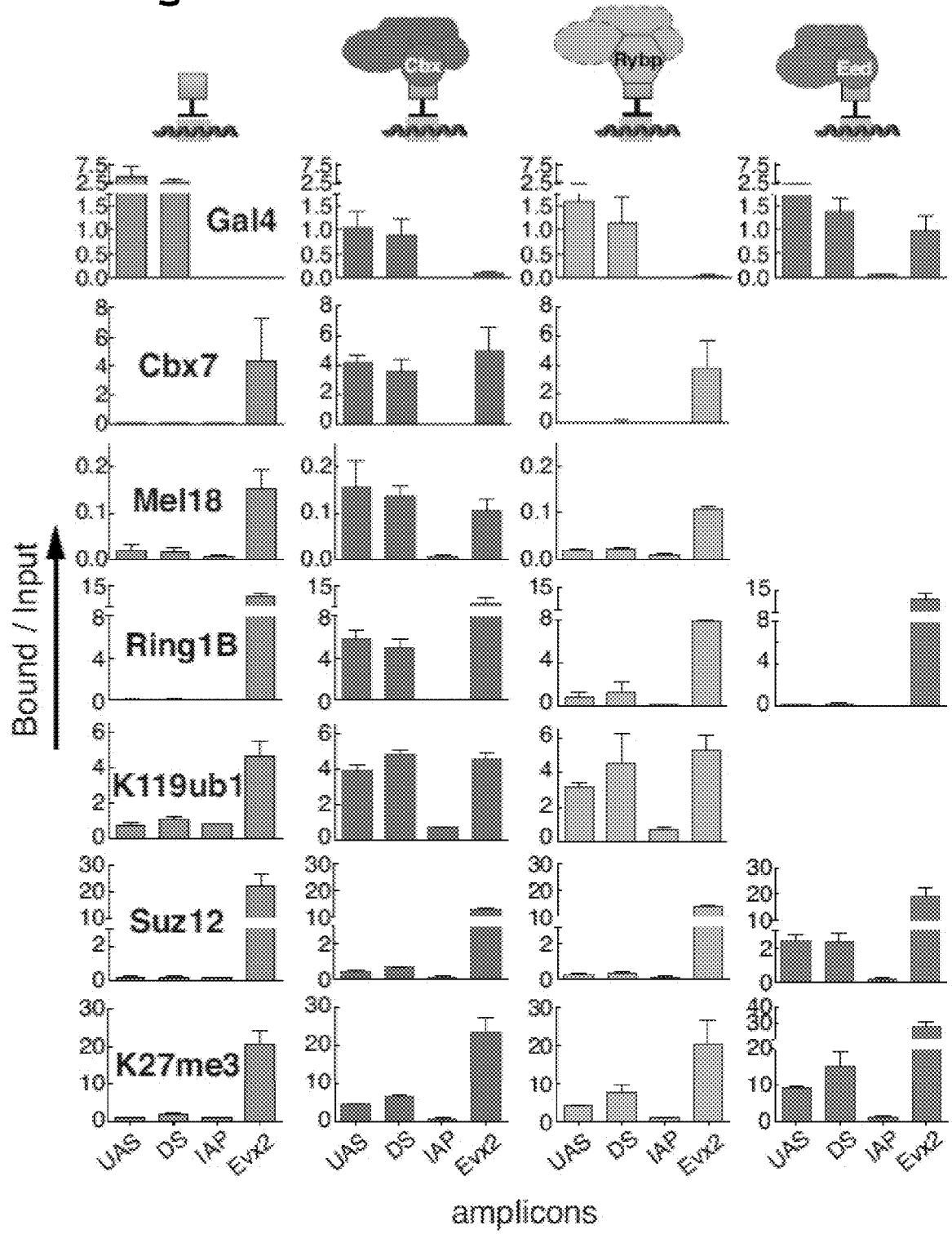

FIG. 6. Targeting core PRC1 and PRC2 subunits at a TetO-independent naïve locus validates establishment of distinct and functional PcG complexes A) Design of mESC line harbouring a single integration of an array of DNA binding sites (12xZFHD1 and 4xGal4 UAS) upstream of a CpG-free GFP. Cbx7, Rybp and Eed are tethered to the DNA binding sites via Gal4-fusion. UAS and DS mark positions of qPCR amplicons. B) ChIP qPCR analyses of active histone modifications in the absence of Gal4 fusion proteins. Gapdh serves as positive control. IAP and Sox17 are negative controls. C) ChIP qPCR analyses show relative enrichments of Gal4 fusions, PcG proteins and histone modifications at the UAS and 0.7 kb downstream (DS) in reporter cells expressing Gal4 alone or fused to Cbx7, Rybp or Eed. IAP and Evx2 serve as negative and positive controls, respectively. Data are mean ±SD (error bars) of three experimental replicates.

FIG. 7. Active histone modifications decorate the 7xTetO site and flanking transcriptionally active reporter genes in parental TetO-mESCs. A) Flow cytometry histograms of BFP expression in the absence and presence of TetR PcG fusion proteins. B) ChIP analyses of active histone modifications in the absence of TetR fusion proteins. Gapdh and IAP serve as positive and negative controls, respectively. Data are mean ±SD (error bars) of three experimental replicates.

FIG. 8. Reversal of TetR-Cbx7 creates a bimodal cell population that persists through DNA replication and cell division. A) Flow cytometry histograms of GFP expression in parental TetOmESCs before and after six days of Dox treatment. B) Flow cytometry histograms show GFP expression in cPRC1-TetO-mESCs at different time points of extended Dox treatment. Percentages (%) indicate fraction of silenced cells. C) Flow cytometry histogram of GFP expression before and after Dox treatment of three different clonal populations of cPRC1-TetO-mESCs. D) Flow cytometry histograms of GFP expression of parental TetO-ESC populations transduced with TetR-Cbx7 or TetR-Rybp before and after six days of Dox treatment. E) Flow cytometry histogram of cPRC1-TetO-mESCs treated with Dox for additional three days after FACS of GFP-positive and -negative cells in response to TetR-Cbx7 reversal.

Figure 9A:
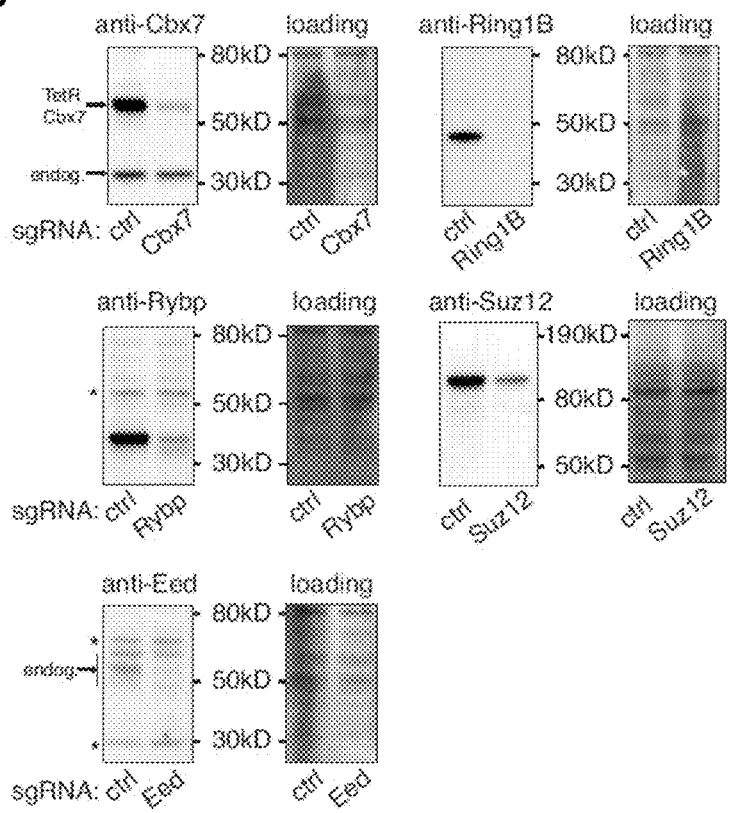
Figure 9B:
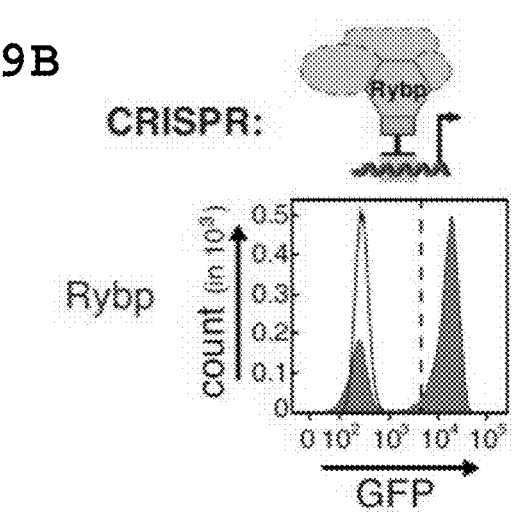
Figure 9C:
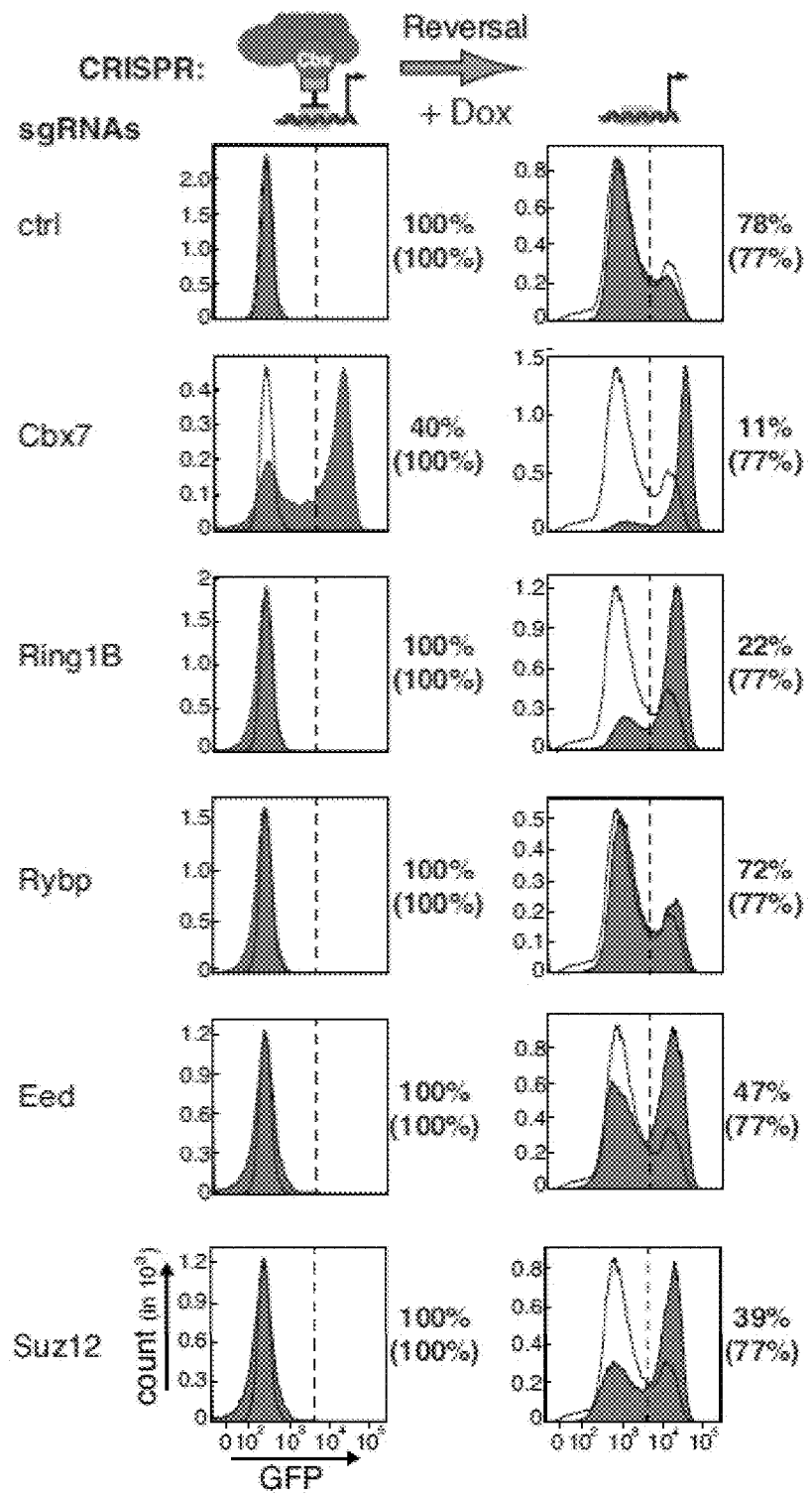

FIG. 9. Functional canonical PRC1 and PRC2 but not variant PRC1 are required to maintain gene silencing established by cPRC1. A) Immuno blots of cPRC1-TetO-mESCs expressing Cas9 together with sgRNAs targeting endogenous PcG proteins. SgRNA against Slc6a6 serves as control. * asterisk denotes unspecific bands. Membrane staining with Coomassie serves as loading controls. B) Flow cytometry of vPRC1-TetO-mESCs in response to transduction of Cas9 and Rybp sgRNAs demonstrates activity and specificity of CRISPR-Cas9 construct used in FIG. 4A. C) Representative flow cytometry analyses of cPRC1-TetO-mESCs expressing Cas9 and sgRNAs against endogenous PRC1 and PRC2 components. Histograms compare GFP expression in untreated and transduced cPRC1-TetO-mESCs with CRISPR-Cas9 constructs before and after six days of Dox addition. SgRNAs are indicated on the left. Percentages indicate GFP-silenced fraction in CRISPR mutant cells and wildtype reporter cells (in brackets).

FIG. 10. Genetic and pharmacological perturbations reveal that Cbx7-H3K27me3 interaction is critical for heritable gene silencing by canonical PRC1 A) Immuno blots of H3K27me3, Ezh2 and Cbx7 show specific and reversible inhibition of the catalytic activity of PRC2 after treatment of parental TetO-mESCs with 4 µM of GSK126 without disrupting endogenous PRC2 and cPRC1 stability. B) Sanger sequencing analysis of endogenous mutant Cbx7 alleles (exon 2, introns 1 and 2 showing the nucleic acid sequence with SEQ ID NO. 1 before the mutation and its corresponding amino acid sequence with SEQ ID NO. 2) confirms homozygous DNA editing that results in amino acid substitution Cbx7W35A (the amino acid sequence with SEQ ID NO. 4 and its corresponding DNA sequence with SEQ ID NO: 3) in the parental TetOmESCs. C) Representative flow cytometry analyses of GFP expression used in FIGS. 4B and D in the context of 30 µM of UNC3688, 30 µM of UNC4219, 4 µM GSK126 or a combination of 30 µM of UNC3688 and 4 µM GSK126. D) Percentage of BFP-negative cells before and after six days of Dox treatment in response to increasing concentrations of Cbx7 inhibitor (UNC3866) alone, in combination with 4 µM GSK126 or the control compound (UNC4219).

Figure 11F:
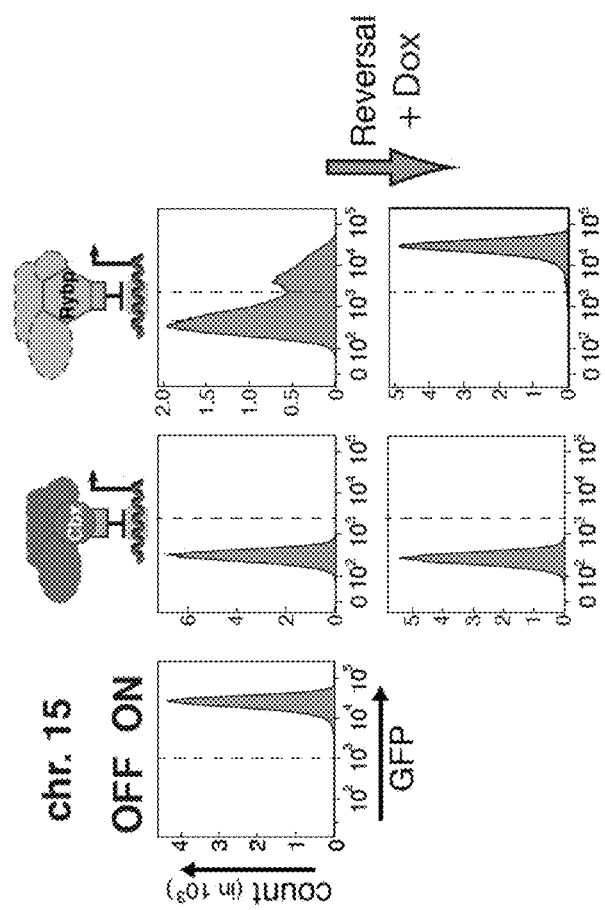
Figure 11E:
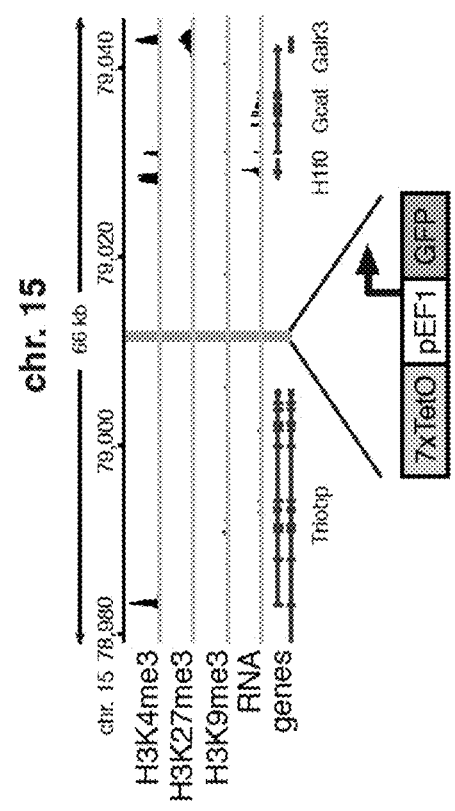

FIG. 11. a), c) and e) Histone modifications and RNA expression surrounding the integration site of a single reporter gene construct located either on chromosomes 1, 7 or 15 in three independent TetO-mESCs. b), d) and f) Flow cytometry histograms relate GFP expression in the absence of TetR PcG fusion proteins, and before and after reversal of TetR fusion protein recruitment in response to Dox treatment for six days.

FIG. 12. Reduction of bulk H2AK119ub1 levels upon PR-DUB overexpression disrupts heritable gene silencing by canonical PRC1. a) Schematic representation of TetR fusion transgenes that enable genetic release of TetR binding to validate heritable maintenance of chromatin modifications and expression state in the absence of the initial stimulus. The DNA sequences encoding mCherry and the TetR DNA binding domain are flanked by two loxp sites enabling Cre recombinase mediated deletion without disrupting downstream DNA sequences. Horizontal black bars indicate primer binding sites for PCR genotyping. b) PCR analyses of TetO-mESCs with transgenes harboring conditional TetR DNA binding domain before and after transfection with Cre recombinase. c) Immuno blot of Cbx7 and Rybp protein expression before and after transfection with Cre recombinase in TetO-mESCs with transgenes harboring conditional TetR DNA binding domain. Membrane staining with Coomassie serve as loading controls. d) Flow cytometry histograms of GFP expression before and after genetic release of TetR DNA binding four days after transfection with Cre recombinase. Combined treatment with 30 µM of UNC3688 and 4 µM GSK126 was used to evaluate the dependence of GFP repression on interaction of the Cbx7 chromodomain with H3K27me3. Percentages (%) indicate fraction of silenced cells. e) Immuno blot compares bulk level of H2AK119ub1 in cPRC1-TetO-mESCs at different dilutions with H2AK119ub1 levels in cPRC1-TetO-mESCs expressing ectopic Bap1 and N-terminal Asx11 (1-479 aa). Detection of PARP serves as a loading control. f) BFP histograms before and after six days of Dox addition to cPRC1-TetO-mESCs without and with overexpression of Bap1 and Asx11 (PR-DUB OE), components of the human PR-DUB complex specific for H2AK119ub1. Parental cPRC1TetO-mESCs (no fill) serve as reference. Percentages indicate fraction of silenced cPRC1-TetO-mESCs with PR-DUB OE and without (in brackets). g) ChIP-qPCR analysis compares the relative enrichments of Cbx2 proteins at TetO site, Evx2 promoter (positive control) and at IAP (negative control) in TetO-mESCs expressing TetR fusions. Similar to endogenous Cbx7, ectopic expression of TetR-Cbx7 leads to downregulation of endogenous Cbx2. Data are mean ±SD (error bars) of three independent experiments.

Figure 13:
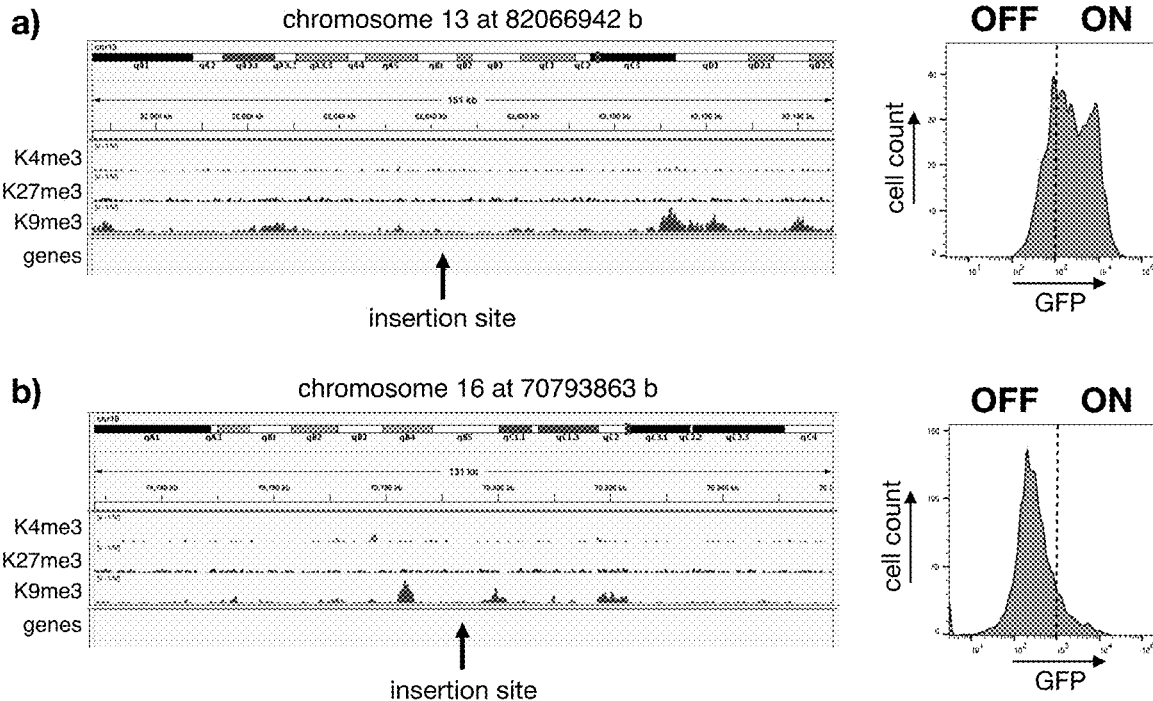
Figure 13:
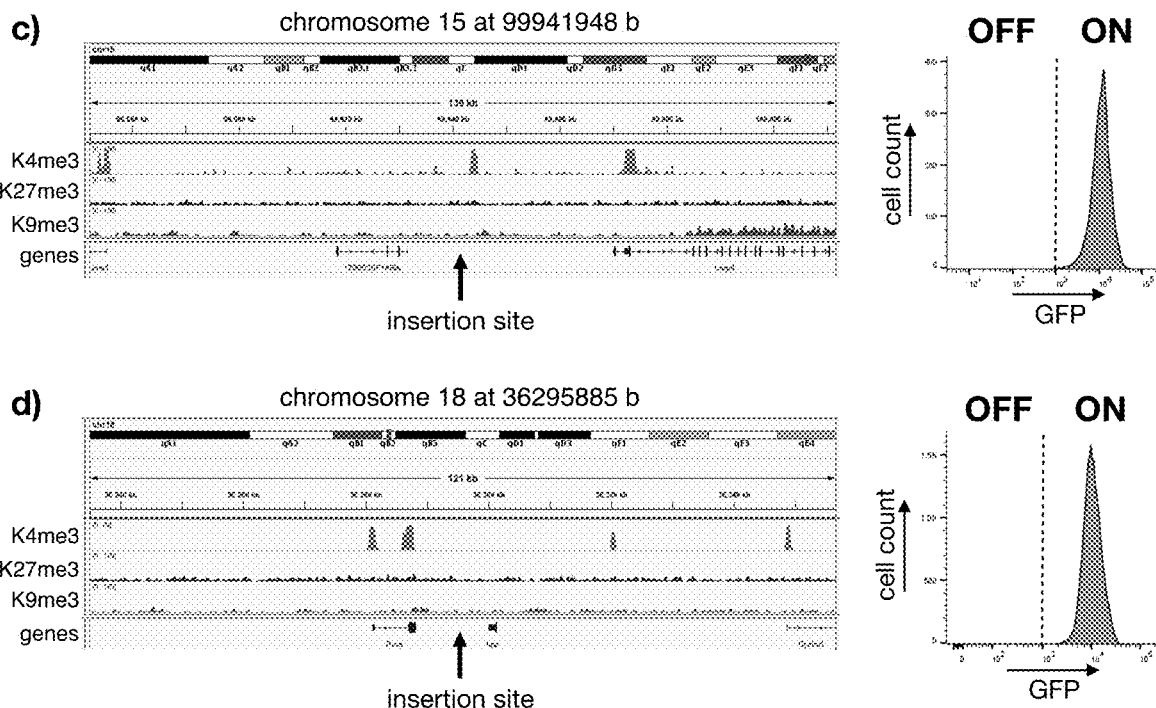

FIG. 13. genomic loci variegation. a) and b) demonstrate a variegated GFP expression pattern is linked to single insertions of the reporter gene in proximity of heterochromatic chromatin modifications including H3K9me3. As a result of predisposed reporter gene silencing, the transcriptional control of the chromatin in vivo assay will be compromised and the dynamic range of GFP signal is reduced. By comparison, c) and d) show that reporter gene insertion in proximity of active genes marked with H3K4me3 can promote GFP expression. In turn, "open" chromatin environment impacts the ability of induced transcriptional repression in response to tethering of chromatin modifiers to the landing site upstream of the reporter gene.

Figure 14:
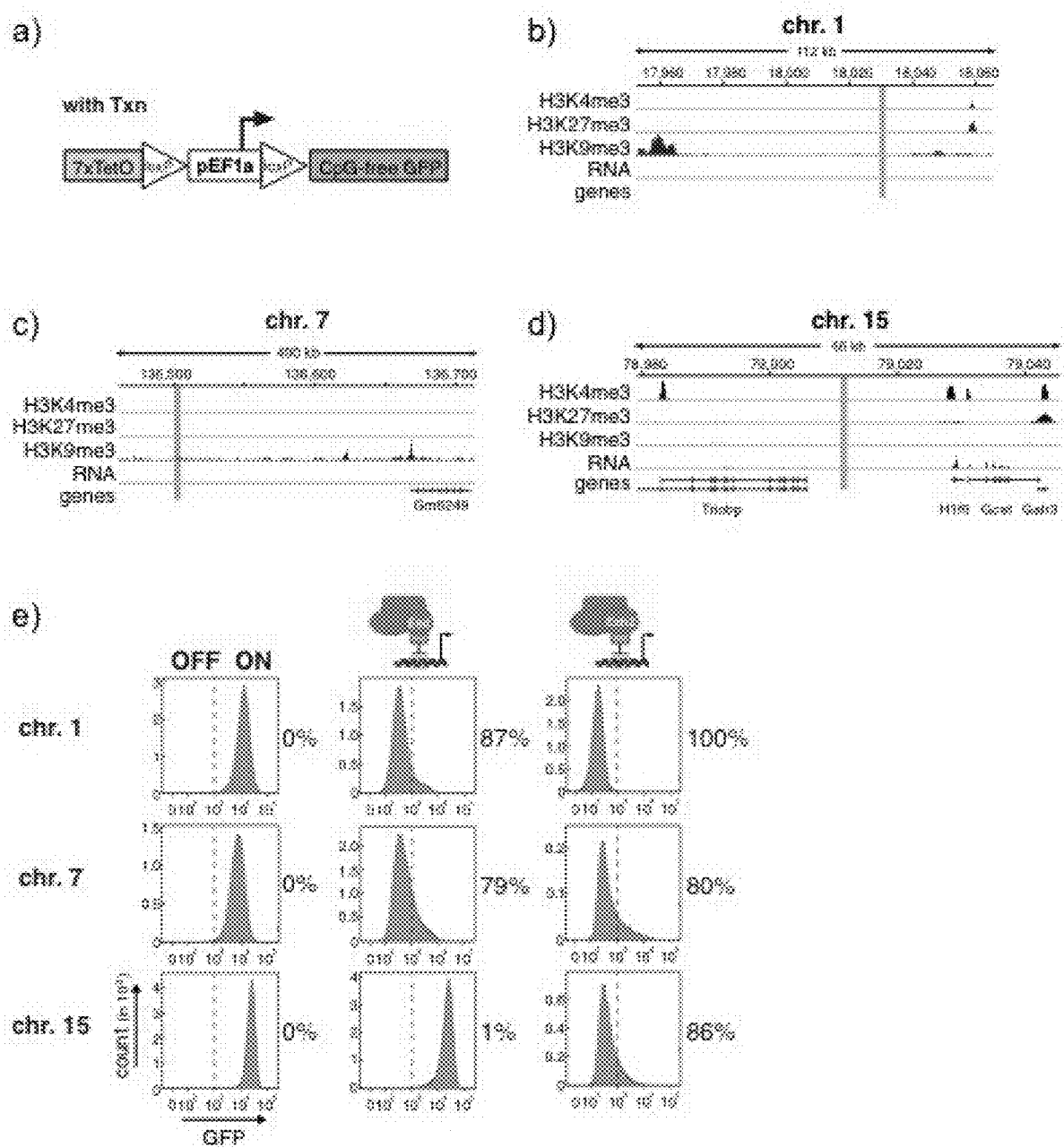

FIG. 14, a) design of the landing site and reporter gene is identical between integration sites on chromosome 1, 7 and 15. b)-d) ChIP-seq and RNA-seq tracks in mouse ES cells shows histone modifications and RNA expression at reporter gene insertion sites on chromosomes 1, 7 and 15. e) Flow cytometry shows GFP expression before and after expression of TetR fusions with Eed and Ezh2. Both fusion proteins can induce transcriptional repression of TetO reporter genes inserted in "naïve" chromatin environments on chromosomes 1 and 7. In contrast, only TetR-Ezh2, but not TetR-Eed, can nucleate repressive chromatin modifications at the insertion site on chromosome 15 which is proximal to active genes and "open" chromatin as marked by H3K4me3.

Figure 15:
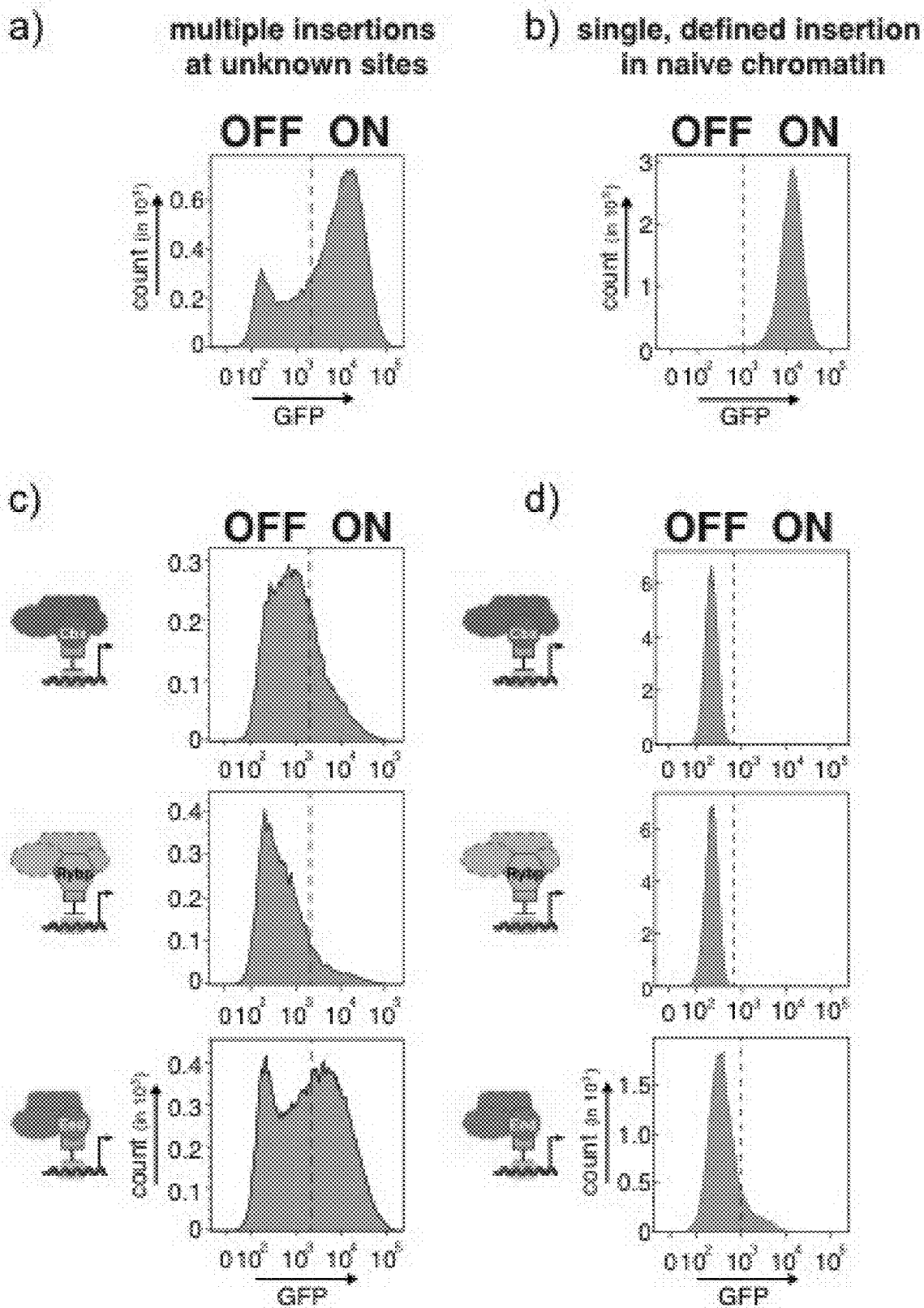

FIG. 15, a) Clonal mESC line with random insertion of reporter gene shows variegated GFP expression. b) Clonal mESC line with known reporter insertion on chromosome 1 in chromatin that lack active and repressive histone modifications. c) Transduced population of reporter cell line in a) with TetR fusions of Cbx7, Rybp and Eed. Population with heterogenous expression of transgene shows variable degree of repression in response to tethering of the respective PcG protein. d) Individual clones of reporter cell line in b) expressing TetR fusions with Cbx7, Rybp and Eed.

EXAMPLES

Example 1: Materials and Methods

Construct Design and Delivery

All constructs were created as lentiviral plasmids under the control of an EF1a- or an UCOE-SFFV promoter driving the genes of interest and an antibiotic resistance (Blasticidin (Invitrogen, R210-01) used at 5 µg/ml or Puromycin (Sigma P8833) or an mCherry-fluorophore tag. For cloning, the genes of interest were PCR amplified by KOD PCR (Novagen, 71086) and inserted into the delivery constructs by Gibson assembly. Lentivirus was produced by PEI co-transfection of the desired construct and two packaging vectors VSV-G (addgene #8454) and psPAX2 (addgene #12260) in HEK293T cells. After 48-72 hours the virus was collected. MESCs were then transduced with the virus for 48 hours in the presence of 8 µg/ml polybrene (Santa Cruz Biotechnology, SACSC-134220). Generation and cell culture conditions of mESC lines. All mESCs used in this study were derived from haploid mESCs (Elling et al., Cell Stem Cell. 9, 563-574 (2011)). Cells were cultivated in ES cell medium consisting of high-glucose-DMEM with 13.5% FBS (Sigma), supplemented with 10 mM HEPES pH 7.4, 2 mM GlutaMAX (Gibco), 1 mM sodium pyruvate (Sigma), 100 U penicillin/ml (Sigma), 0.1 mg streptomycin/ml (Sigma), 1×MEM non-essential amino acids (Sigma), 50 mM β-mercoptoethanol (Gibco) and recombinant LIF. For generation of TetO-mESCs a construct consisting of 12×ZFHD and 5×Gal4 DNA binding sequences upstream of an EF1a promoter driven tagBFP with a SV40 poly-A tail sequence followed by 7xTetO DNA sequences upstream of a PGK promoter driven puromycin antibiotic resistance and a eGFP separated by an IRES sequence with another SV40 poly-A tail. The sequence replaced a genetrap on chromosome 15 by recombinase-mediated cassette exchange RMCE) (Lienert et al., Nature Publishing Group. 43, 1091-1097 2011)). The TetOFF-independent reporter mESC line was generated by random integration of a construct consisting of 12×ZFHD and 5×Gal4 DNA binding sequences upstream of a coding sequence of a CpG less GFP with a poly-A tail followed by a PGK driven Cre-ER-T2, IRES and a neomycin antibiotic resistance sequence flanked by loxP sites. For reversal of TetR fusion protein binding, TetO-mESCs were transferred to ES cell medium supplemented with 1 µg/ml doxycycline (Sigma, D9891).

Flow Cytometry Analysis and Sorting

All flow cytometry analyses were conducted on a LSR Fortessa (BD Biosciences) using BD FACS Diva or FlowJo software. For fluorescent cell sorting a FACS ARIA III (BD Biosciences) was used. Isolation of haploid mESCs entailed incubation with 20 µg/ml Hoechst 33342 (Thermo Scientific Fisher) for 30 min at 37° C. and 5% $CO_2$ prior to FACS. Selection of transgene expression by Thy 1.1 required surface staining with a Thy1.1 specific antibody. After incubation in PBS containing 1% FBS with Fc-blocking antibody at 1:500 (Affymetrix eBioscience Anti-Mouse CD16/CD32 Purified) for 5 min at RT, mESCs were treated with Thy 1.1 antibody (Affymetrix eBioscience Anti-Mouse/Rat CD90.1 (thy-1.1) APC-eFluor 780) at 1:750 for 30 min in darkness.

Chromatin Immunoprecipitation (ChIP-qPCR)

Chromatin Immunoprecipitations were performed as previously described (Hathaway et al., Cell. 149, 1447-1460 (2012)). Briefly, 30-50×$10^6$ mESCs were trypsinized for 6-8 min prior to quenching with FBS containing ES cell medium. 25×$10^6$ mES cells were collected, washed in once in 1×PBS and crosslinked with formaldehyde at a final concentration of 1% for 7 min. The crosslinking was stopped on ice and with glycine at final 0.125 M concentration. The crosslinked cells were pelleted by centrifugation for 5 min at 1200 g at 4° C. Nuclei were prepared by washes with NP-Rinse buffer 1 (final: 10 mM Tris pH 8.0, 10 mM EDTA pH 8.0, 0.5 mM EGTA, 0.25% Triton X-100) followed by NP-Rinse buffer 2 (final: 10 mM Tris pH 8.0, 1 mM EDTA, 0.5 mM EGTA, 200 mM NaCl). Afterwards the cells were prepared for shearing by sonication by two washes with Covaris shearing buffer (final: 1 mM EDTA pH 8.0, 10 mM Tris-HCl pH 8.0, 0.1% SDS) and resuspension of the nuclei in 0.9 mL Covaris shearing buffer (with 1× protease inhibitors hibitors complete mini (Roche)). The nuclei were sonicated for 15 min (Duty factor 5.0; PIP 140.0; Cycles per Burst 200; Bath Temperature 4° C.) in 1 ml Covaris glass cap tubes using a Covaris E220 High Performance Focused Ultrasonicator.

Input samples were prepared from 25 µL sonicated lysate. Therefore, chromatin was RNase A and Proteinase K digested and cross-link reversed overnight at 65° C. DNA was then precipitated and shearing of DNA was confirmed to be between 500-1000 bp by agarose gel electrophoresis. Crude chromatin lysate was further processed by spinning at 20000 g at 4° C. for 15 min and supernatant used for ChIP. An equivalent of 50 µg DNA was incubated overnight in 1×IP buffer (final: 50 mM HEPES/KOH pH 7.5, 300 mM NaCl, 1 mM EDTA, 1% Triton X-100, 0.1% DOC, 0.1% SDS) with following antibodies at 4° C. on a rotating wheel: 0.5 µl H3K27me3 (Diagenode, C15410195), 3 µl Ring1B (Cell Signaling, D22F2), 1.5 µl Suz12 (Cell Signaling, D39F6), 1.5 µl H3K4me3 (Millipore, 05-745R), 7.5 µl Me118 (Santa Cruz, sc-10744), 2 µl Cbx7 (Abcam, ab21873), 1.5 µl RYBP (Sigma Aldrich, PRS2227), 1.5 µl FLAG (Sigma Aldrich, F1804), 1.5 µl H3K27ac (Abcam, ab4729), 1.5 µl H2AK119ub (Cell Signaling, D27C4), 7.5 µl Gal4 (Santa Cruz, sc-510).

The overnight IPs were incubated with BSA-preblocked Protein G coupled Dynabeads (Thermo Fisher Scientific) for more than 6 h at 4° C. on a rotating wheel. IPs were subsequently washed 5× with 1×IP buffer (final: 50 mM HEPES/KOH pH 7.5, 300 mM NaCl, 1 mM EDTA, 1% Triton-X100, 0.1% DOC, 0.1% SDS), 3× with DOC buffer (10 mM Tris pH 8, 0.25 mM LiCl, 1 mM EDTA, 0.5% NP40, 0.5% DOC) and 1× with TE (+50 mM NaCl). The DNA was then eluted 2× with 150 µL Elution buffer (final: 1% SDS, 0.1 M NaHCO3) for 20 min each at 65° C. The eluate was treated with RNase A and Proteinase K and crosslink reversed overnight at 65° C. The IP DNA was PCIA extracted and precipitated and quantified using qPCR on a CFX Connect Real-Time PCR Detection System (Biorad).

Western Blot

Nuclear extract from 10×10$^6$ mESCs was obtained by lysis in Buffer A (final: 25 mM Hepes ph 7.6, 5 mM MgCl2, 25 mM KCl, 0.05 mM EDTA, 10% Glycerol, 1 mM DTT, 1 mM PMSF, 1× Complete Mini protease inhibitor) followed by collection in RIPA buffer (final: 150 mM NaCl, 1% triton, 0.5% sodium deoxy-cholate, 0.1% SDS, 50 mM Tris pH 8.0). Nuclear extracts were homogenized by sonication in a Diagenode Bioruptor and concentration was determined by Bradford assay (Biorad). 20 µg/lane total protein was run on Novex Life Technology NuPAGE 4-12% Bis-Tris gels in Invitrogen NuPAGE MES SDS Running Buffer and transferred on a Merck Chemicals Immobilon-P Membrane (PVDF 45 µm). The membrane was blocked (5% non-fat dry milk in 1×PBS, 0.1% Tween 20) and incubated with the following primary antibodies (5% non-fat dry milk in 1×PBS, 0.1% Tween 20): H3K27me3 (Diagenode, C15410195), Cbx7 (Abcam, ab21873), RYBP (Sigma, PRS2227), H2AK119ub (Cell Signaling, D27C4), Ezh2 (Active Motif, 39901). Finally, the membrane was incubated with corresponding secondary HRP coupled antibodies (5% non-fat dry milk in 1×PBS, 0.1% Tween 20), developed using Clarity Western ECL Substrate (Biorad) and imaged by a ChemiDoc XRS+ Imaging system (Biorad).

Generation of Cbx7$^{W35}$A TetO-mESCs and CRISPR/Cas9 Editing in cPRC1-TetO-mESCs MESCs harboring homozygous Cbx7$^{W35}$A chromodomain point mutation in exon 2 of the endogenous Cbx7 gene were generated by CRISPR/Cas9 technology. CRISPR KOs of endogenous PcG genes in cPRC1-TetO-mESCs were obtained by CRISPR/Cas9 technology. CRISPR guide RNAs were designed using the online tool of the Zhang lab (crispr.mit.edu, Zhang, MIT 2015) and cloned in modified lentiviral CRISPR/Cas9 expression vectors expressing the gRNAs driven by a U6 promoter and a wildtype hSPCas9 with either a Thy1.1 marker or a blasticidin selection marker separated by a P2A driven by an EFS promoter. Parental TetO-mESCs were co-transfected with CRISPR/Cas9 expression vectors and a 200 bp double-stranded DNA oligonucleotide with homology arms flanking a substitution of GCT for TGG (FIG. 10B) using the Amaxa nucleofection protocol for mESCs (Lonza). After 24-36 hrs the cells were sorted positive for Thy1.1. Positive Cbx7$^{W35}$A TetO-mESC clones were identified by PCR genotyping. CRIPSR/Cas9 expression vectors to disrupt endogenous PcG genes was delivered into cPRC1-TetO-mESCs via lentiviral infection followed by blasticidin selection.

Chemical Inhibition of Ezh2 and/or Cbx4/7 in TetR-Flag-Cbx7 mES Cells $4 \times 10^3$ cPRC1-TetO-mESCs were treated for three days on 96 well plates in both absence and presence of 1 µg/ml doxycycline (Sigma, D9891) with following chemical inhibitors: Ezh2 inhibitor GSK126 (Axora, BV-2282), increasing concentrations of negative control compound UNC4219, Cbx4/7 antagonist UNC3866 alone or in combination with 4 µM GSK126 (Stuckey et al., *Nature Chemical Biology*. 12, 180-187 (2016)). Dilutions of UNC3866 and UNC4219 were prepared in DMSO.

Generation of Growth Curves $1 \times 10^5$ respective mESCs were plated in the beginning. After 24, 48 and 72 hours mESCs were collected and stained with trypan blue for counting (Countess™, Invitrogen AMQAX1000). Cell counts were performed in duplicates.

Conditional Depletion of TetR-AID-Cbx7 Transgene

Parental TetO-mESCs and Cbx7$^{KO}$ TetO-mESCs were transduced with DB52 and DB53 and clones with high TIR1 and TetR-AID-Cbx7 expression were isolated. All cells were treated for 72 hrs in the presence or absence of Doxycycline (1 µg/ml final concentration) alone or in combination with Auxin (500 µM final concentration).

Conditional Deletions of TetR DNA Binding Domains

TetO-mESCs were transduced with DB82 and DB84 and mCherry-positive clones were isolated. For genetic reversal of TetR fusion protein binding, reporter cell clones expressing conditional TetR fusions were transduced with Cre recombinase using the mouse ES Cell Nucleofector Kit (Lonza) and Thy1.1-positive cells were sorted out after 24-36 hours. Flow cytometry analysis of mCherry and GFP expression was carried out after 96 hours. Both nuclear protein extracts and genomic DNA were collected reporter cells prior (mCherry-positive) and after (mCherry-negative) transfection with Cre recombinase.

Example 2: Assembly of Distinct PcG Complexes

Figure 1A:
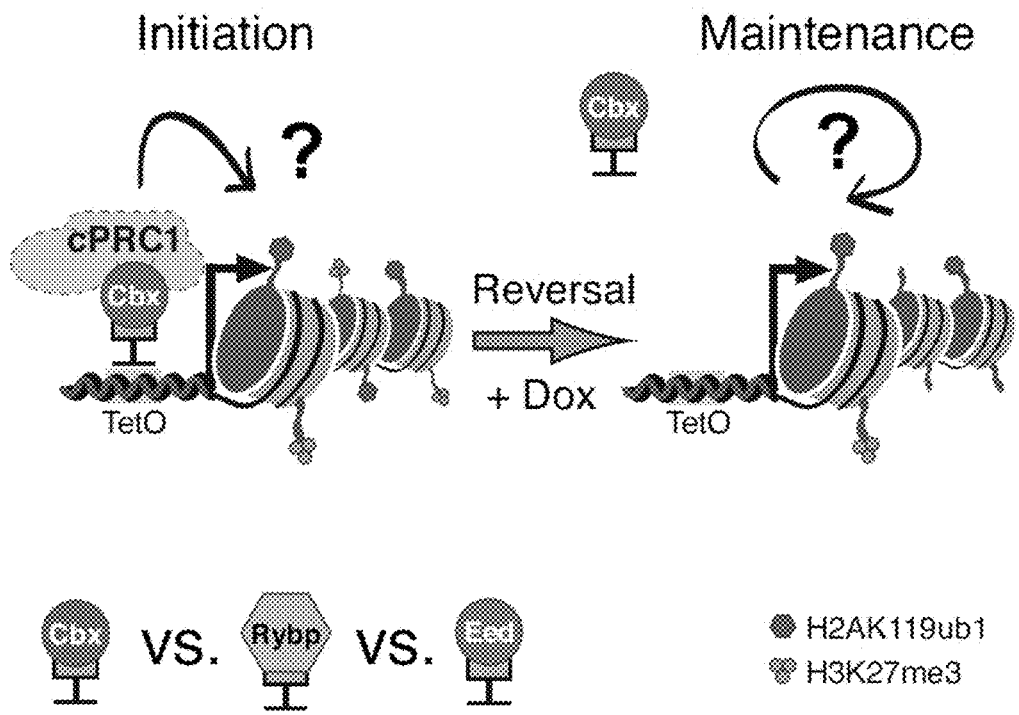

To uncover how canonical and variant PRC1 and PRC2 contribute to the initiation and maintenance of repressive chromatin, we engineered mouse embryonic stem cells (mESCs) that reversibly tether individual PcG complex members to distinct genomic Tet operator (TetO) sites via the Tet$^{OFF}$ system (Urlinger et al., *Proceedings of the National Academy of Sciences*. 97, 7963-7968 (2000)). We ectopically expressed different core subunits of mESC-specific PcG complexes fused to FLAG-Tet repressor (TetR) in these lines: Cbx7 as a member of canonical PRC1 (cPRC1-TetO), Rybp as a member of variant PRC1 (vPRC1-TetO) or Eed as a member of PRC2 (PRC2-TetO) (FIG. 1A). We hypothesized that their binding to TetO will facilitate nucleation of functional PcG complexes and thus enable a direct comparison of different modifying-activities on the same chromatin template. To determine the capacity of different modifying activities to induce gene silencing, we compared the consequences of PcG protein recruitment at a naïve locus and at a transcriptionally active site. Moreover, because TetR recruitment is reversible upon Doxycycline (Dox) treatment, we could monitor potential differences in heritability of PcG-dependent chromatin modifications and silencing through cell divisions, after loss of the initial stimulus.

Figure 1B:
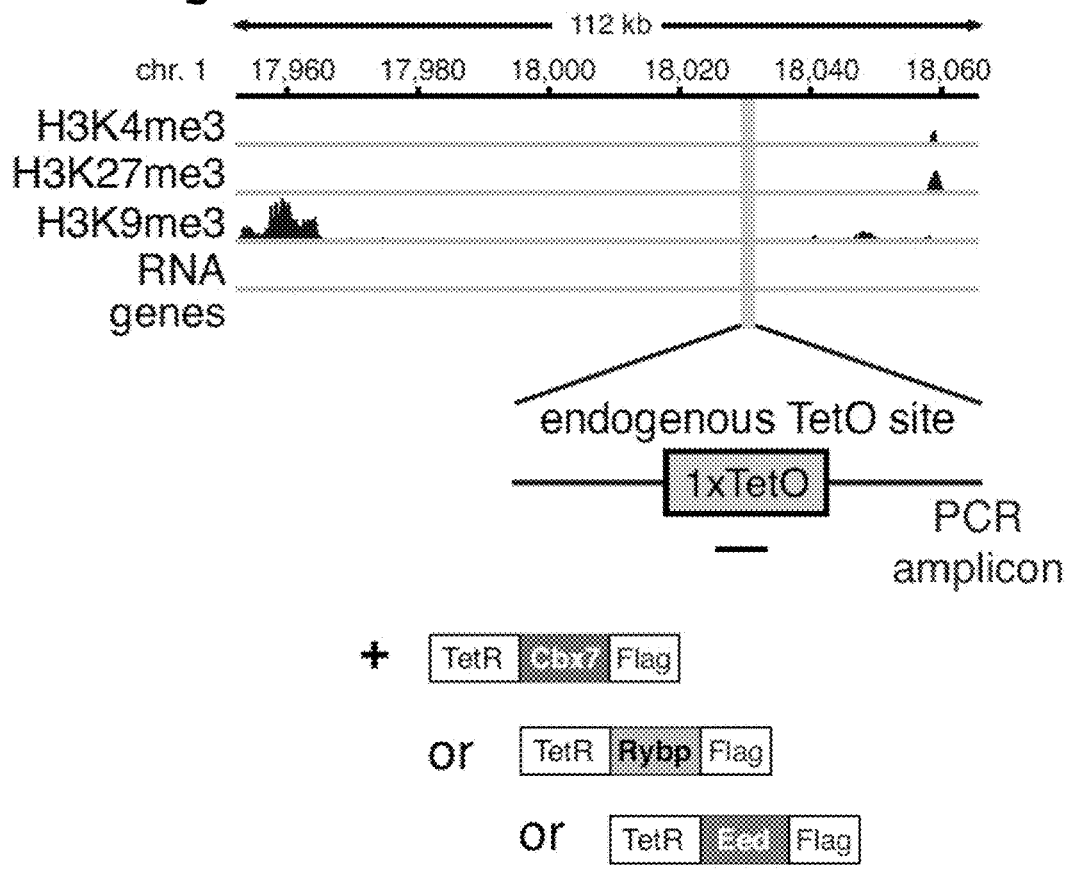
Figure 1C:
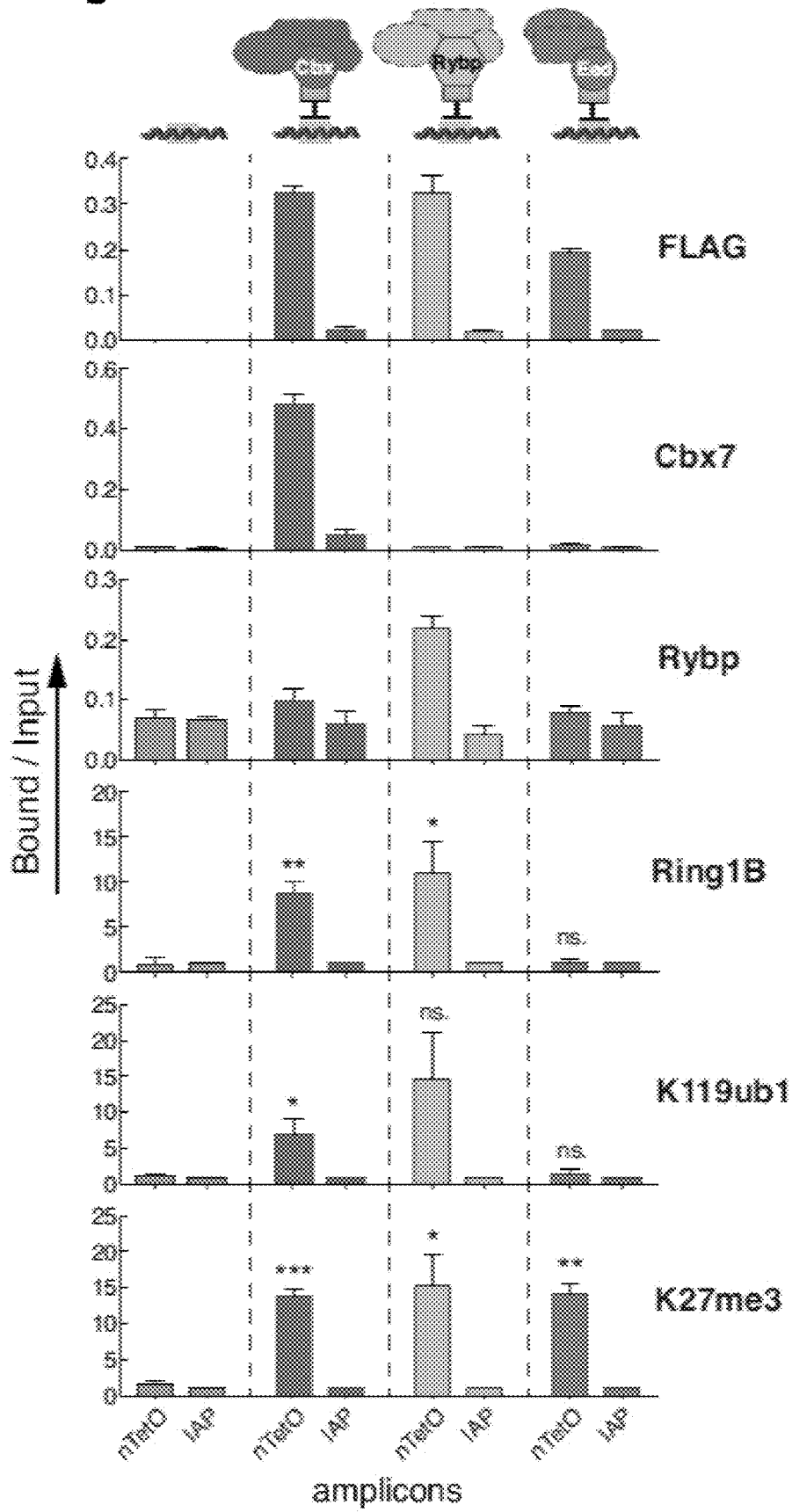
Figure 5A:
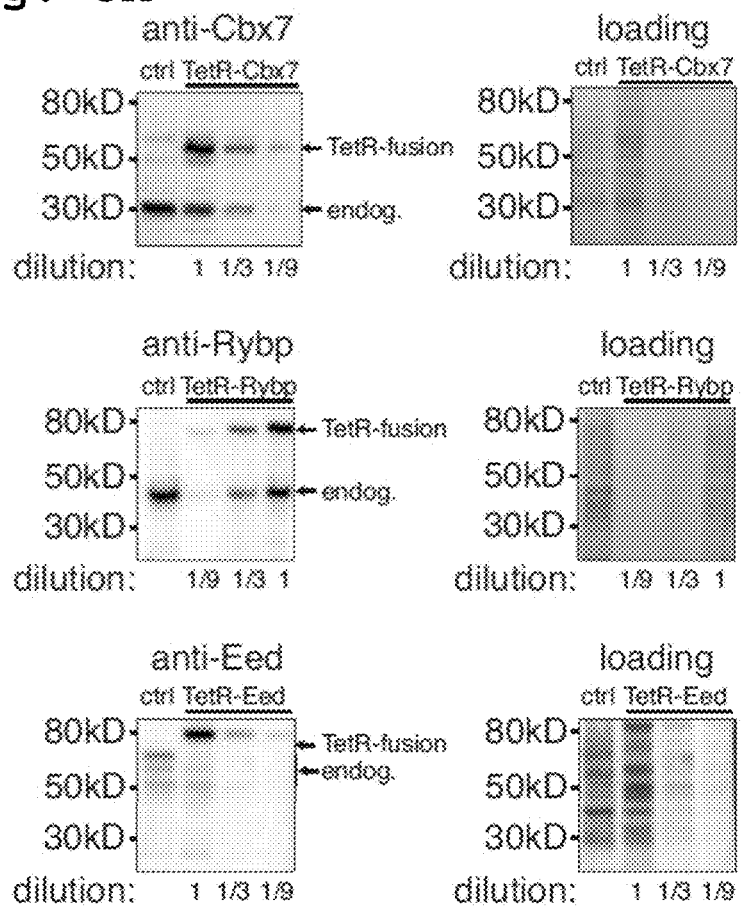
Figure 5B:
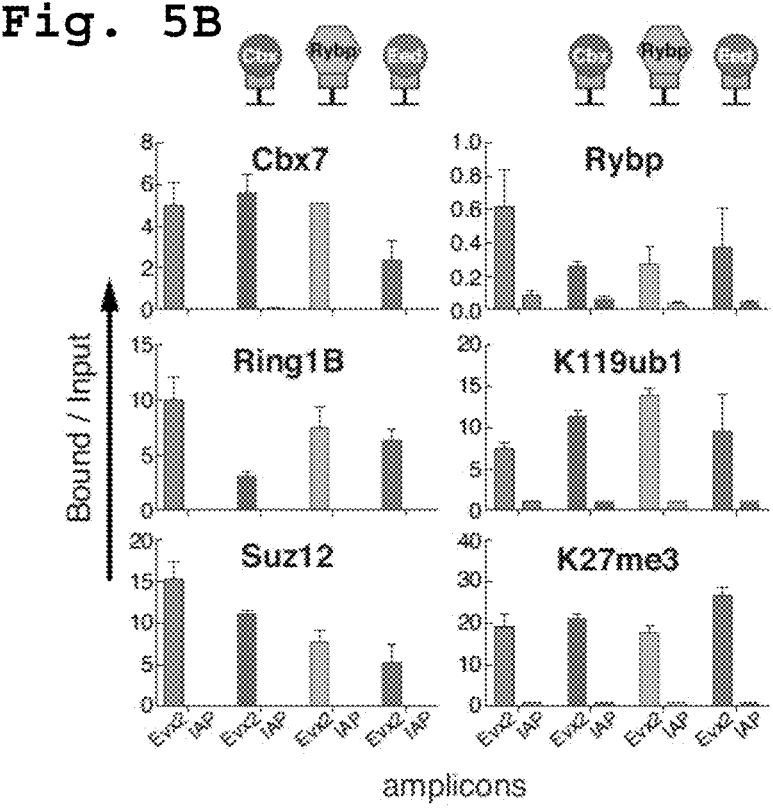

First, we asked if ectopic recruitment of different core subunits to a naïve landing site would direct the assembly of distinct PcG complexes. We monitored enrichment of FLAG, endogenous PcG proteins and chromatin modifications at a naturally occurring single TetO sequence located within a transcriptionally inactive region (naïve TetO-nTetO) on mouse chromosome 1 (FIG. 1B). Expression of TetR-Cbx7 or -Rybp led to enrichment of Ring1B and H2AK119ub1 at nTetO but not at a control site (FIG. 1C and FIG. 5A). This tethering formed distinct PRC1 complexes, since Rybp was not detected upon tethering of Cbx7 and vice versa. Furthermore, variant or canonical PRC1 targeting led to PRC2 recruitment and H3K27me3, establishing a pattern characteristic of endogenous Polycomb target genes (FIG. 1C and FIG. 5B). By comparison, Eed tethering led to enrichment of H3K27me3, suggesting nucleation of PRC2. However, PRC1 and H2AK119ub1 were not recruited as a result of PRC2 localization. To validate our findings in a $Tet^{OFF}$-independent setting, we generated an mESC line containing Gal4 UAS sites (5xUAS) within a region that lacks active and repressive histone modifications or signs of Polycomb activity (FIGS. 6A, B and C). The 5xUAS were upstream of a GFP:Puromycin reporter gene. This DNA binding array enables selective recruitment of canonical PRC1 complexes in the context of native chromatin structure. Ectopic tethering of PRC1 subunits, such as a CBX Kme reader, to a reporter locus results in localization of endogenous PRC1 components and the resulting histone modifications reflect assembly of fully functional canonical PRC1 complexes. Similar to the naive TetO site, Gal4-mediated recruitment of Cbx7, Rybp or Eed to the UAS sites resulted in enrichment of endogenous PcG proteins and histone modifications. Thus, ectopic recruitment of core PRC1 or PRC2 subunits is sufficient to nucleate assembly of functionally distinct PcG complexes and recapitulate PcG-dependent chromatin modifications. Strikingly, synthetic PRC1-mediated chromatin changes induce transcriptional repression in our reporter ES cells, thereby extending the Chromatin in vivo assay (CiA) to Polycomb signaling. Hence, we have built a unique cellular assay system that directly links transcriptional repression of a GFP reporter to the specific PRC1 CBX activities we seek to disrupt. In addition, since we can link any CBX domain, this assay can assess cellular potency and selectivity within the CBX family in the context of native chromatin structure.

Example 3: Disruption of TetO Binding

Figure 5C:
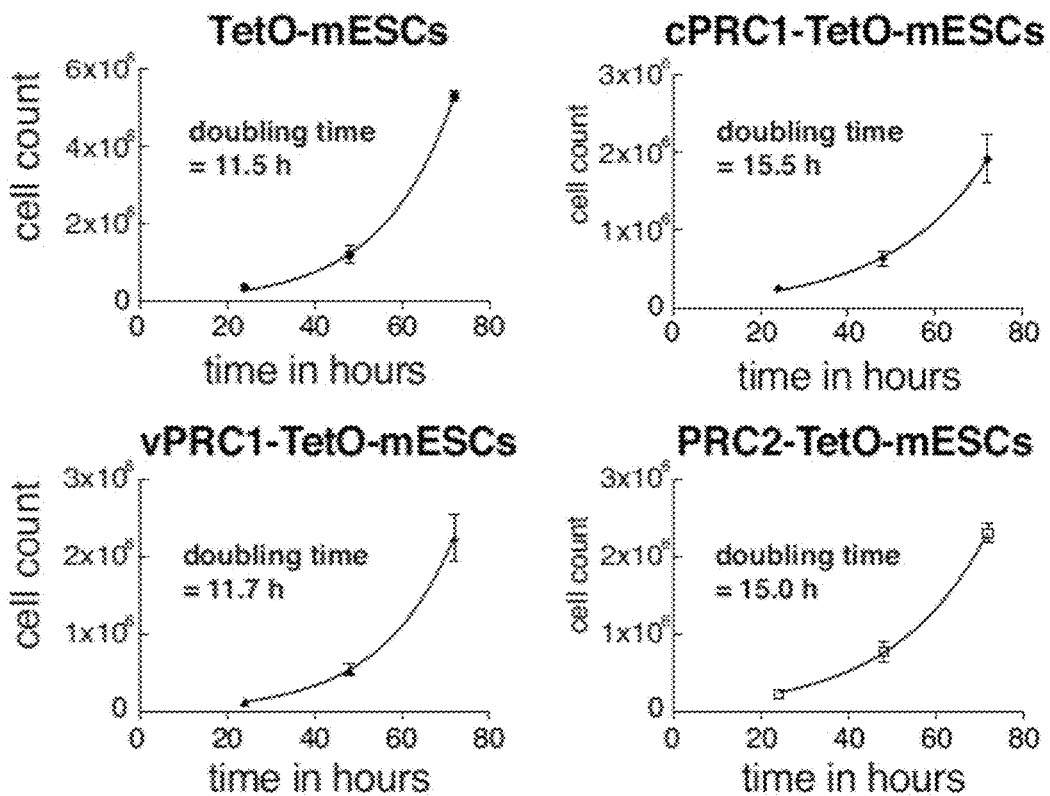

To determine if PcG protein targeting and histone modifications could be transmitted through mitotic cell divisions after reversal of the initiator, we released TetR PcG fusion binding from TetO sites by adding Doxycycline (Dox), a disruptor of binding to TetO. We treated the TetO-mESC lines with Dox for six days to allow approximately 10-12 cycles of replication and cell division based on the monitored growth rate (FIG. 5C). This time interval would be sufficient to dilute any chromatin modifications to base line that are not maintained in the absence of the TetR fusion stimulus (FIG. 1D—dashed line). ChIP analyses confirmed the release of TetR fusion proteins from the naive TetO site after Dox treatment (FIG. 1D). Reversal of ectopic Cbx7- or Rybp tethering resulted in a concomitant loss of endogenous Ring1B and H2AK119ub1. In contrast, H3K27me3 levels remained substantially enriched, albeit reduced, despite the loss of PRC1 activities. Similarly, H3K27me3 also remained enriched after reversal of TetR-Eed tethering (FIG. 1D). The persistence of H3K27me3 suggests an epigenetic mechanism of sequence-independent PRC2 retargeting in transcriptionally inactive regions. Conversely, H2AK119ub1 is not sufficient to promote self-reinforcing PRC1 recruitment, suggesting non-redundant roles of PRC1 and PRC2 and the epigenetic maintenance of their associated histone modifications.

Example 4: Reporter Assay

Figure 2A:
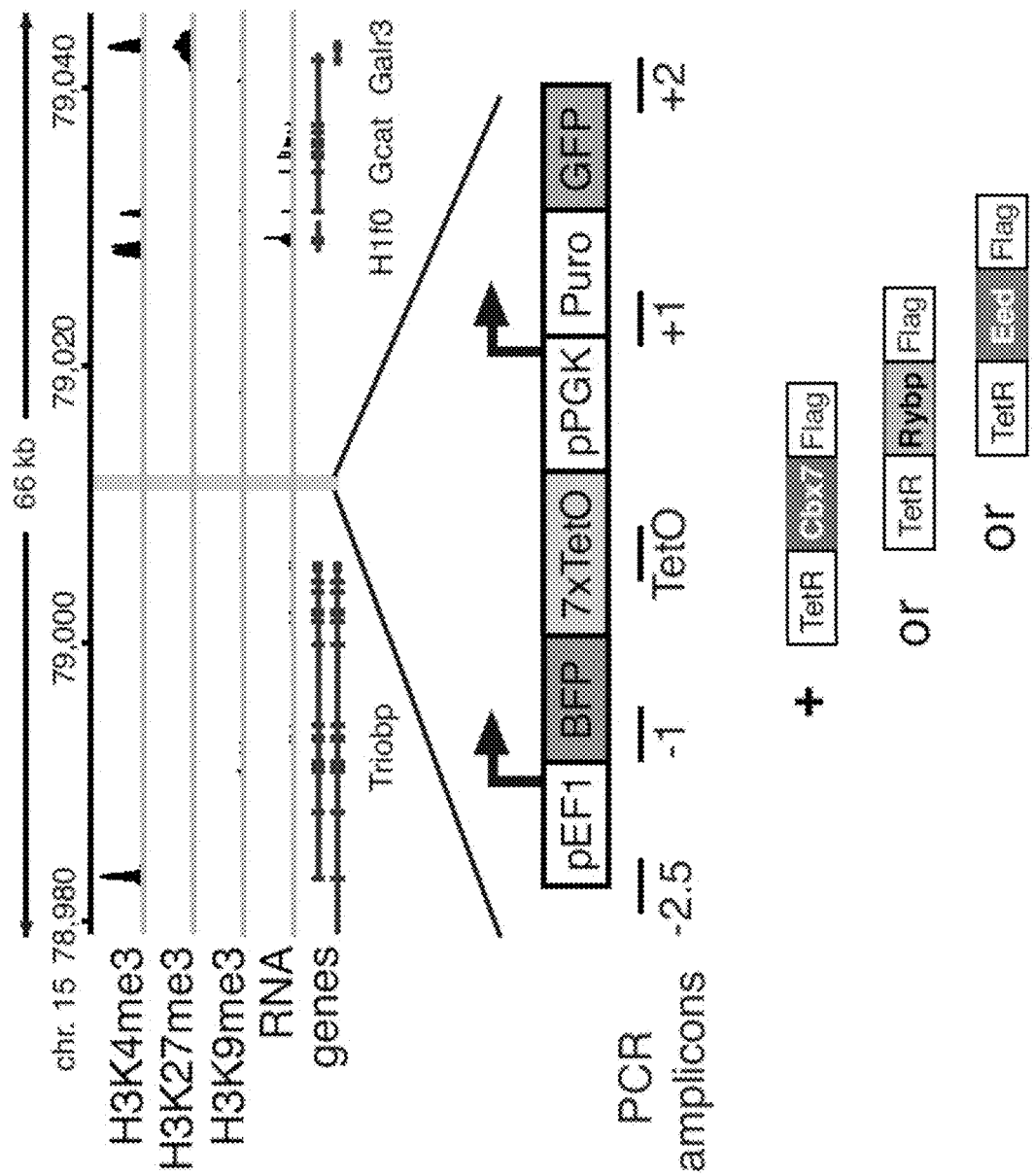
Figure 2B:
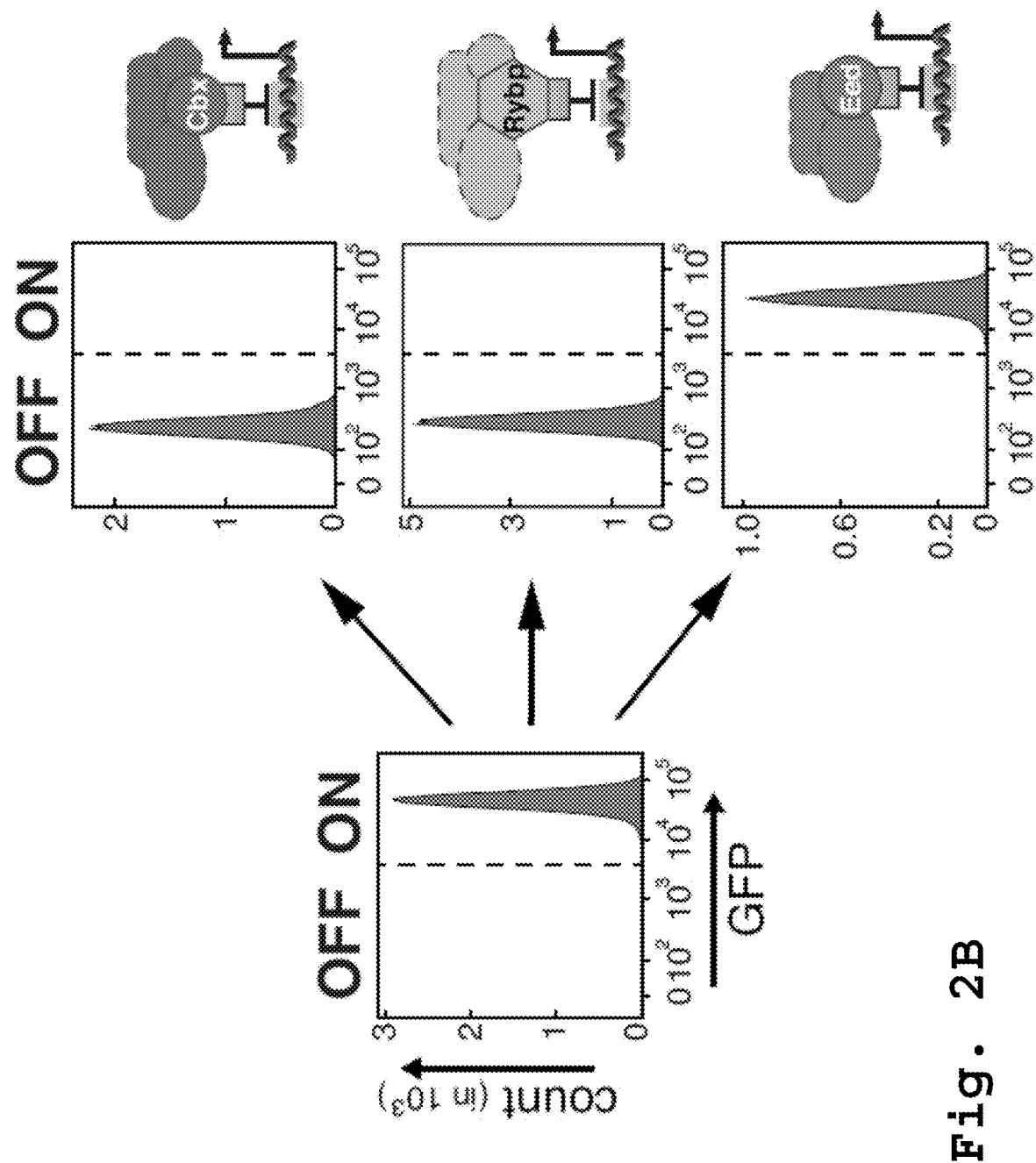
Figure 7A:
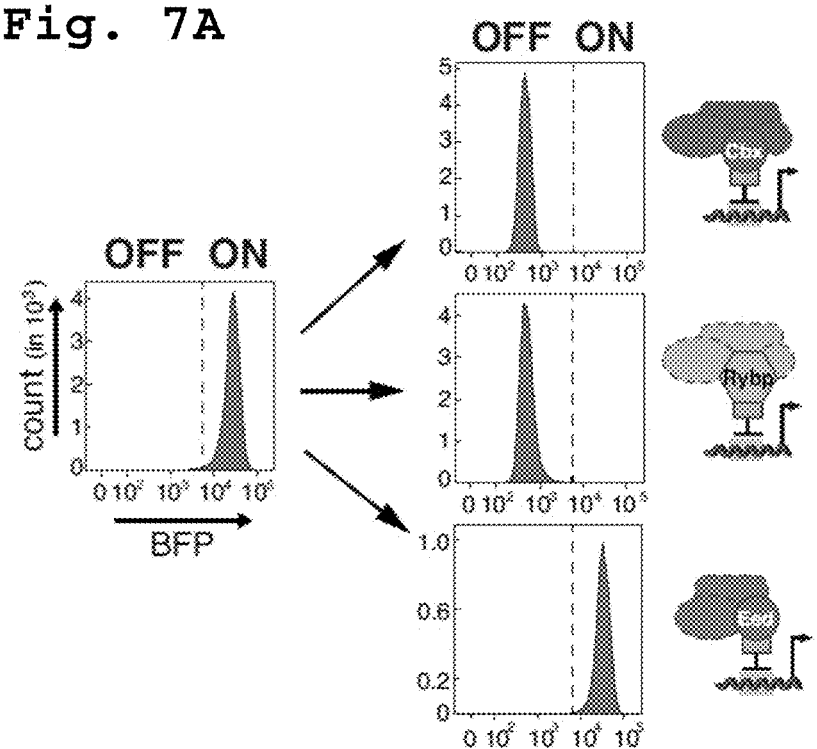
Figure 7B:
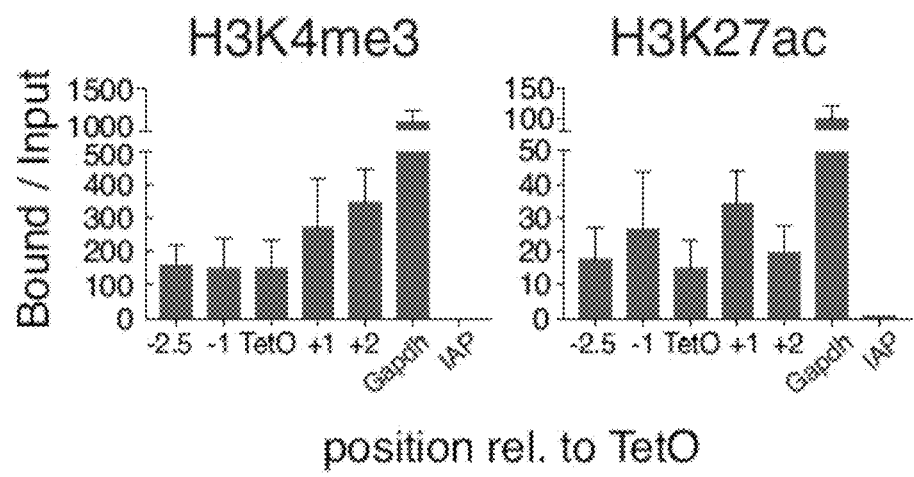

To extend our investigation to the consequences of PRC1 and PRC2 targeting to transcriptionally active regions, we monitored a second TetO site in TetO-mESC which was generated by homozygous insertion of an array of seven TetO sequences (7xTetO) flanked by a proximal GFP reporter and a distal BFP reporter (FIG. 2A). Similar to the naive locus, this (random) integration site on chromosome 15 was devoid of PcG-dependent histone modifications in the parental lines (FIG. 1B and FIG. 2A). Flow cytometry indicated that both reporters were highly and homogenously expressed in TetO-mESCs (FIG. 2B and FIG. 7A). Tethering of TetR-Cbx7 and -Rybp substantially reduced the expression of GFP and BFP (FIG. 2B and FIG. 7A). This silencing of the proximal and distal reporters was accompanied by Ring1B recruitment and H2AK119ub1 deposition across 7xTetO and flanking regions consistent with spreading of repressive chromatin domains (FIG. 2C). Moreover, tethering of Cbx7 or Rybp conferred distinct assemblies of canonical PRC1 or variant PRC1, respectively (FIG. 2C). In contrast to PRC1, TetR-Eed tethering failed to silence the reporter genes and did not result in Suz12 and H3K27me3 enrichment at 7xTetO (FIG. 2B, C and FIG. 7A). Given that Eed tethering nucleates PRC2 activity within the transcriptionally inactive region at nTetO, we conclude that PRC2 may primarily maintain, rather than initiate, PcG-dependent transcriptional repression. It is possible that active histone modifications at the transcriptional reporter in parental cells interfere with the catalytic activity of PRC2 (FIG. 7B).

Example 5: Persistence of Histone Modifications

Figure 3A:
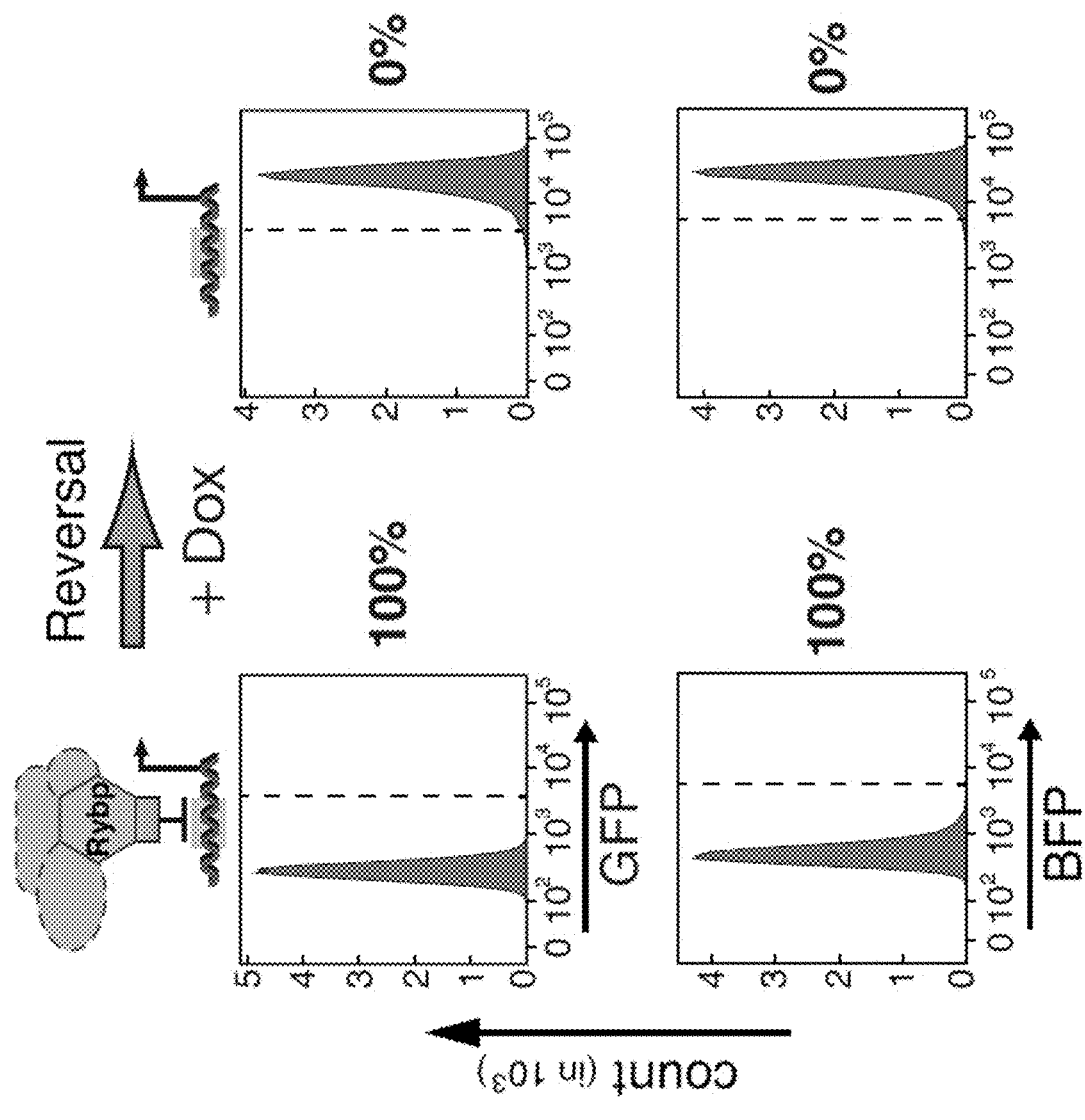
Figure 3B:
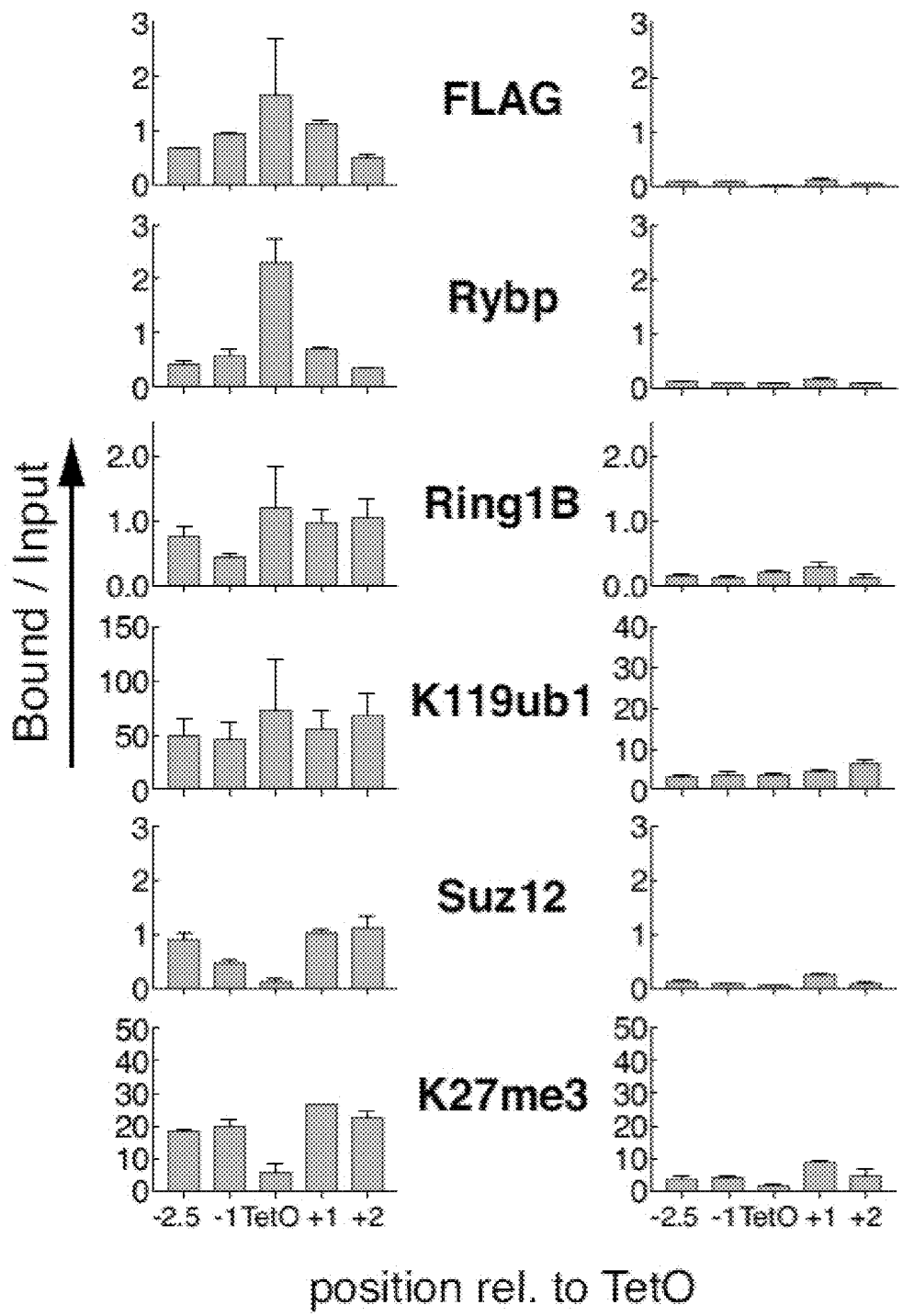
Figure 8A:
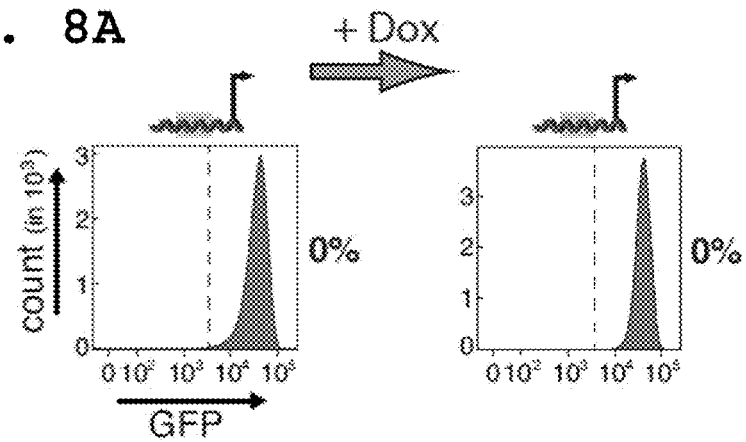

Having established that ectopic recruitment of PRC1 subunits is sufficient to initiate gene silencing and recapitulate large domains of PcG-dependent chromatin modifications (of both PRC1 and PRC2), we investigated whether the resulting repressive chromatin would persist through cell divisions after release of TetR PcG fusions. Reversing TetR tethering of variant PRC1 by Dox resulted in rapid reactivation of GFP and BFP reporters as measured by flow cytometry (FIG. 3A). Dox had no effect on reporter gene expression in parental reporter cells, indicating a specific response to lack of variant PRC1 (FIG. 8A). ChIP analysis revealed that loss of silencing reflected displacement of vPRC1 and PRC2, and concomitant loss of their respective histone modifications, from 7xTetO as well as flanking regions (FIG. 3B). Hence, similarly to the naive TetO site, variant PRC1-dependent chromatin modifications and gene silencing were not transmitted through genome replication and cell division in the absence of sequence-dependent TetR-Rybp recruitment.

Figure 8B:
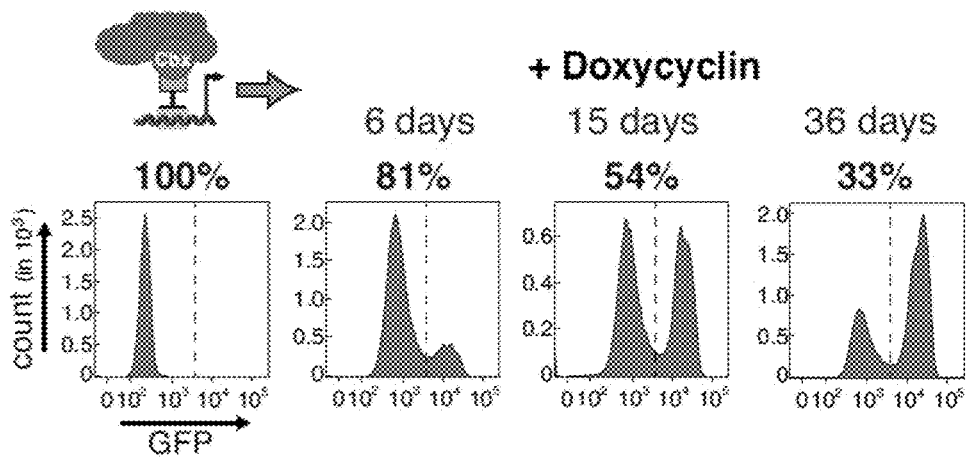
Figure 8C:
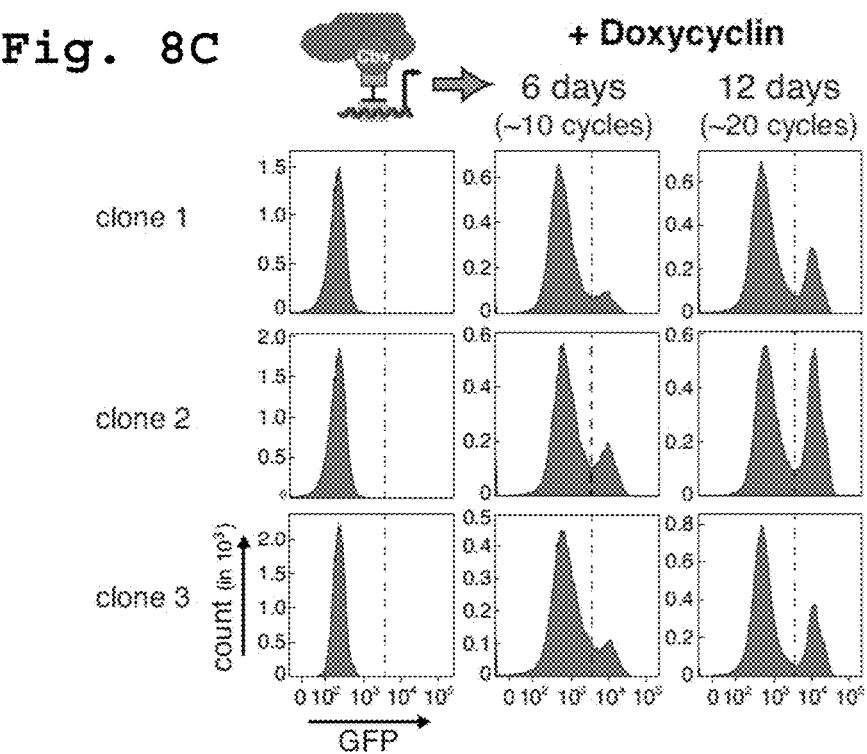
Figure 8D:
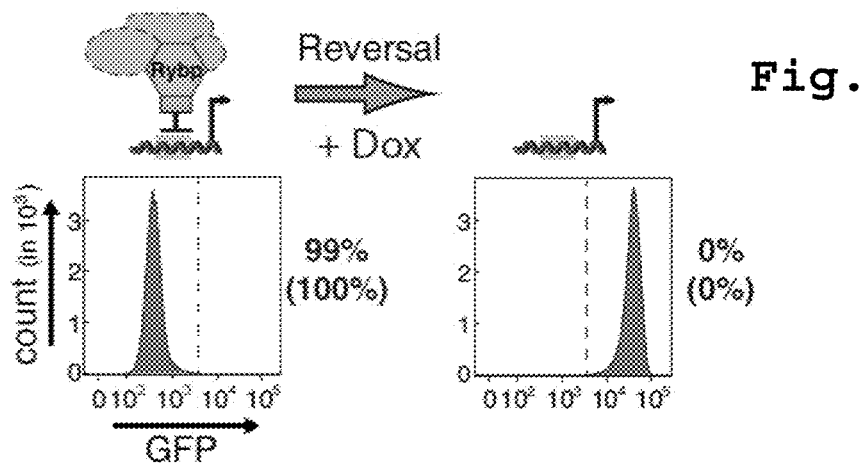
Figure 8E:
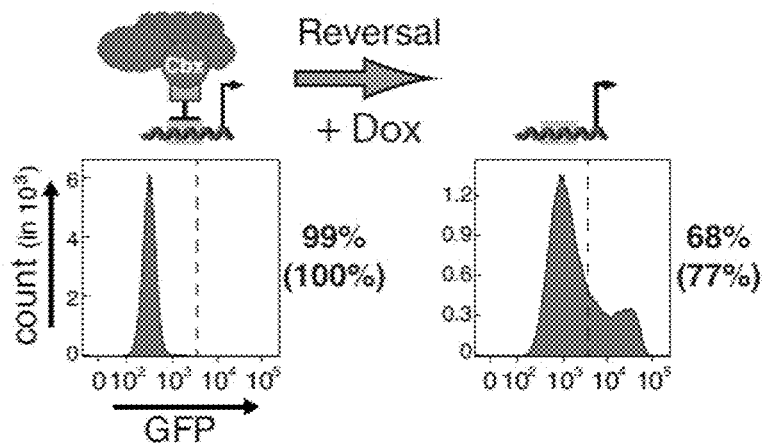
Figure 8E:
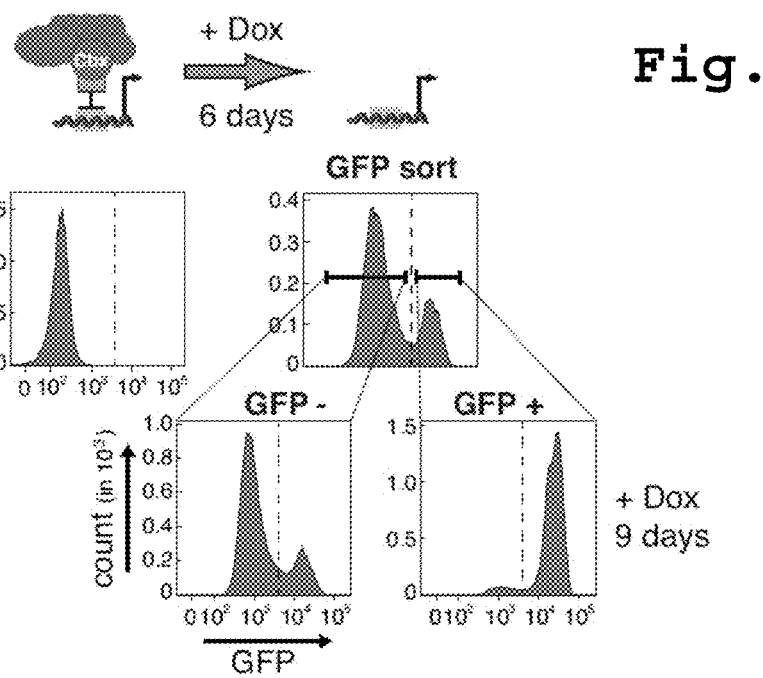

In sharp contrast, Dox-dependent release of TetR-Cbx7 gave rise to a bimodal cell population: a small fraction of cells reactivated the reporter genes, yet the majority continued to silence GFP and BFP (FIG. 3C). Prolonged Dox treatment gradually increased the fraction of reactivated reporter cells, nevertheless the bimodal distribution persisted for more than 36 days which reflects approximately 50-60 cell divisions (FIG. 8B). This maintenance of reporter silencing was reproducible between independent clones and with different expression levels of TetR-Cbx7 in a population (FIGS. 8C and D). In addition, sorting of GFP-positive and GFP-negative cells following Dox treatment demonstrated that the bimodal distribution reflects two separate populations (FIG. 8E).

Figure 3D:
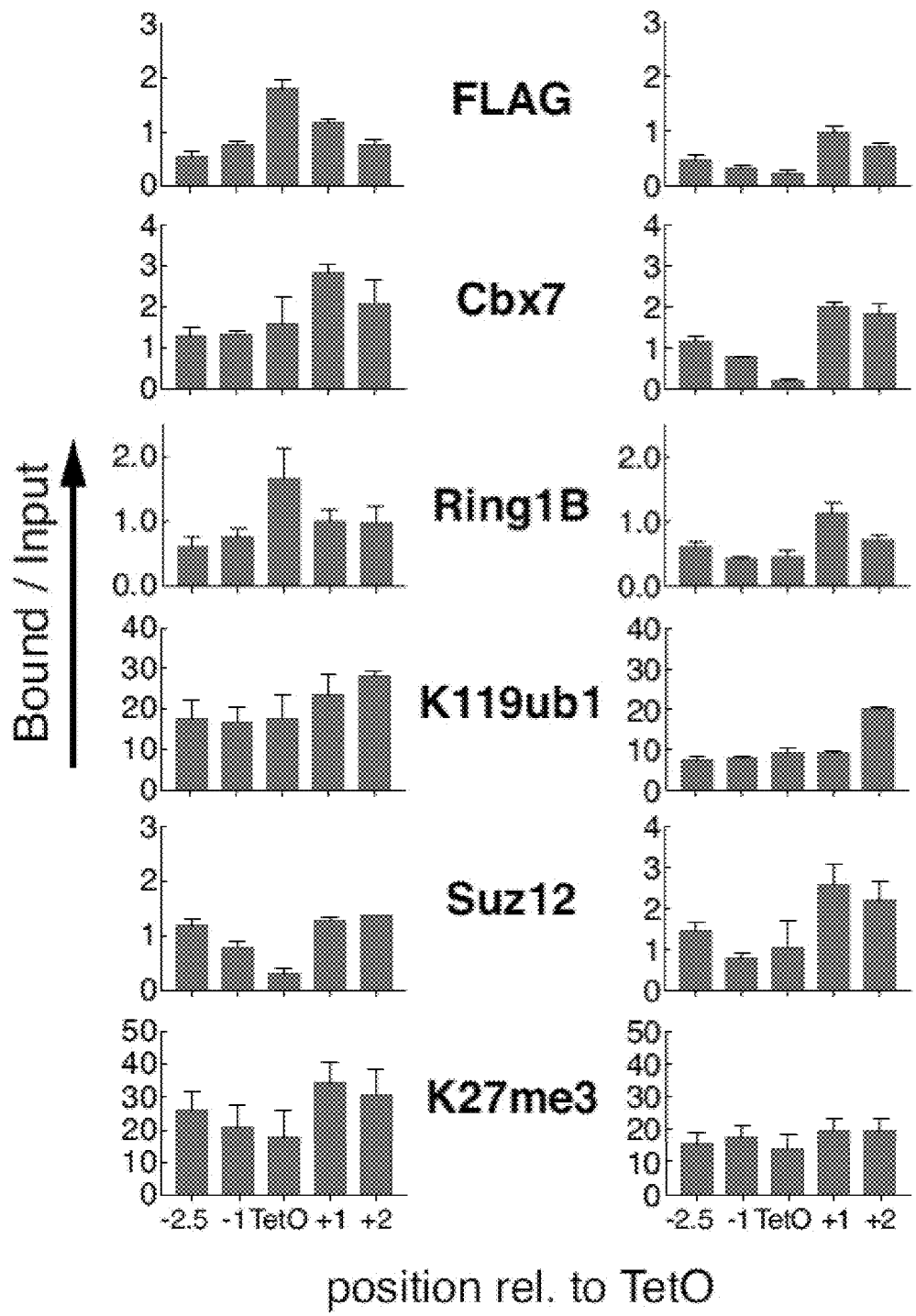

ChIP analysis after Dox-dependent TetR-Cbx7 release from the 7xTetO site confirmed that maintenance of repression reflected persistence of histone modifications and cPRC1 and PRC2 complexes in the absence of the original stimulus (FIG. 3D). To determine if transmission of TetR-Cbx7-dependent repression through cell divisions was limited to the tandem reporter design or its genomic integration site, we generated three additional TetO-mESC lines by inserting a 7xTetO sequence with a single GFP reporter gene on chromosomes 1, 7 and 15; at loci devoid of transcriptional activity and PcG-dependent histone modifications in the parental cell line. As in the original reporter line, expression of TetR-Cbx7 and -Rybp induced reporter gene silencing, yet maintenance of repression after Dox treatment was only observed in case of TetR-Cbx7 (FIG. 12a-f). Hence, our direct comparison of reversible tethering of variant and canonical PRC1 complexes revealed striking differences in the heritable transmission of Polycomb-dependent repression. Unlike vPRC1, cPRC1 promotes sequence-independent maintenance of PcG-dependent gene repression.

Figure 4A:
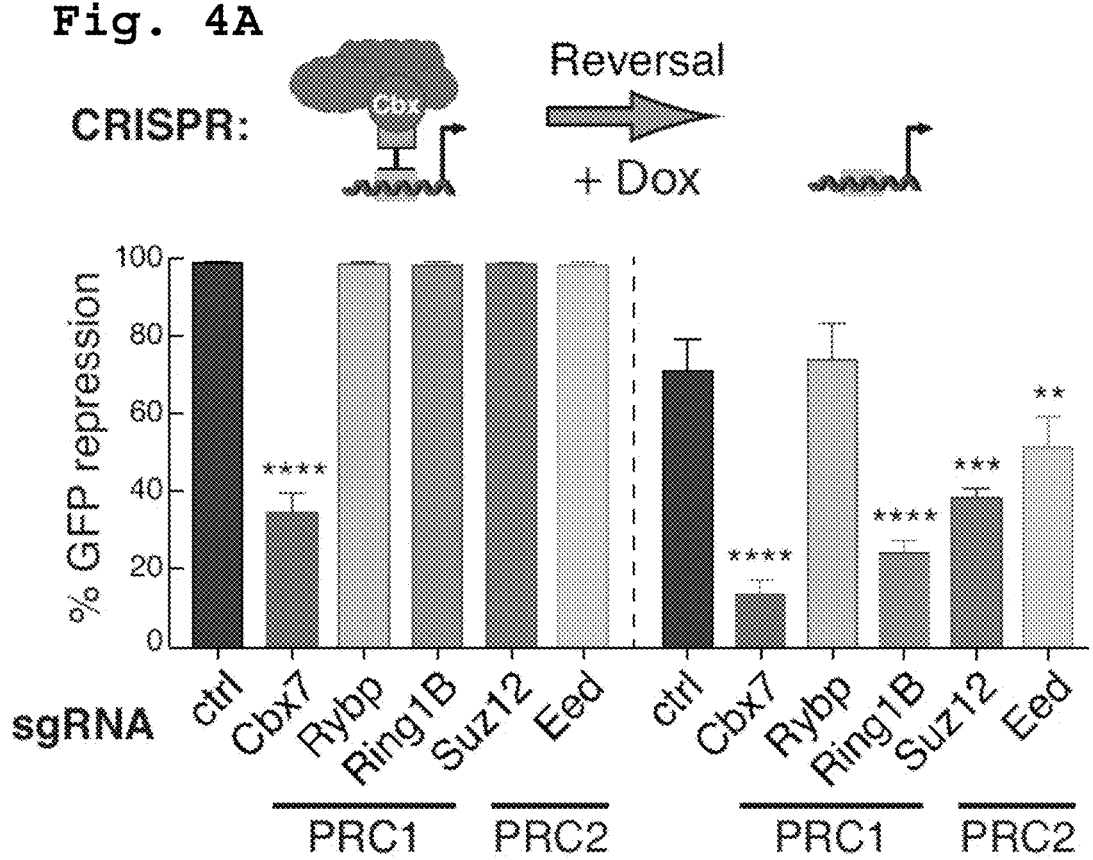

Although TetR-Cbx7 was depleted at the 7xTetO site upon Dox treatment, it was still enriched at flanking regions, co-localizing with Suz12 and H3K27me3 (FIG. 3D). To delineate the requirements for maintaining transcriptional gene silencing, we used CRISPR/Cas9 to generate loss-of-function alleles in genes encoding different PRC1 and PRC2 components. Flow cytometry was used to quantify maintenance of GFP repression in cPRC1-TetO-mESCs stably expressing Cas9 together with validated sgRNAs (FIGS. 9A and B). PRC1 functions were disrupted with sgRNAs targeting Cbx7 (cPRC1), Ring1B (both) and Rybp (vPRC1), whereas PRC2 function was disrupted with sgRNAs Eed and Suz12. sgRNAs against an unrelated gene (Slc6a6) served as control. Treating cells with Cbx7-sgRNAs disrupted the initiation of GFP reporter silencing consistent with loss of TetR-Cbx7 expression (FIG. 4A and FIGS. 9A and C). Upon Dox treatment, more than 70% of cells remained GFP-negative in wildtype and Rybp-sgRNA-treated reporter cells (FIG. 4A, compare to FIG. 9B) suggesting that variant PRC1 is not required to maintain repression established by canonical PRC1. In contrast, Dox treatment reactivated reporter gene expression in cells with sgRNA-mediated loss of Ring1B- and Cbx7. Thus, maintenance of cPRC1-initiated repression relies on functional integrity of endogenous, canonical PRC1. Mechanistically, Suz12 and Eed were also required for maintenance of repression, suggesting that PRC2 integrity and/or H3K27me3 are involved in sequence-independent cPRC1 targeting in mitotic cells (FIG. 4A and FIGS. 9A and C).

Figure 4B:
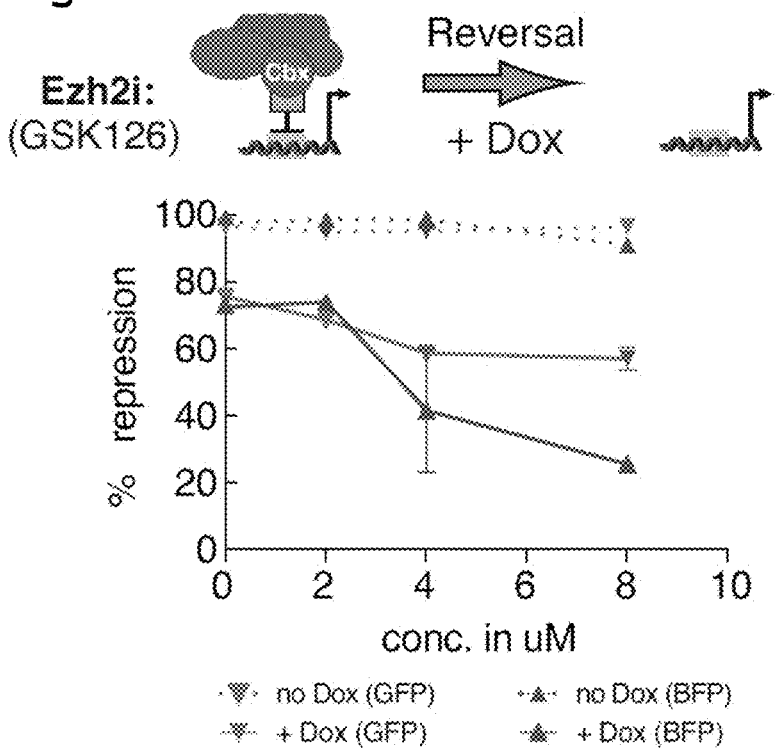
Figure 10A:
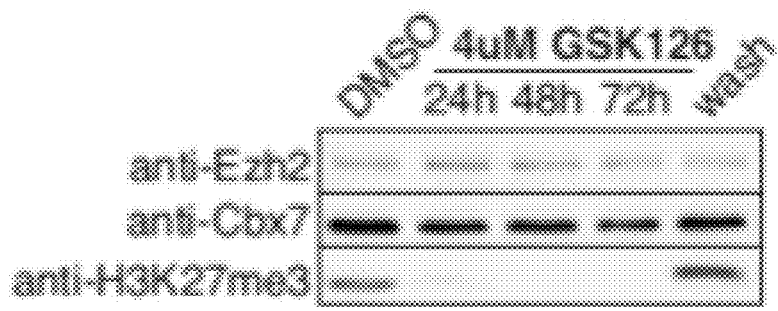
Figure 10D:
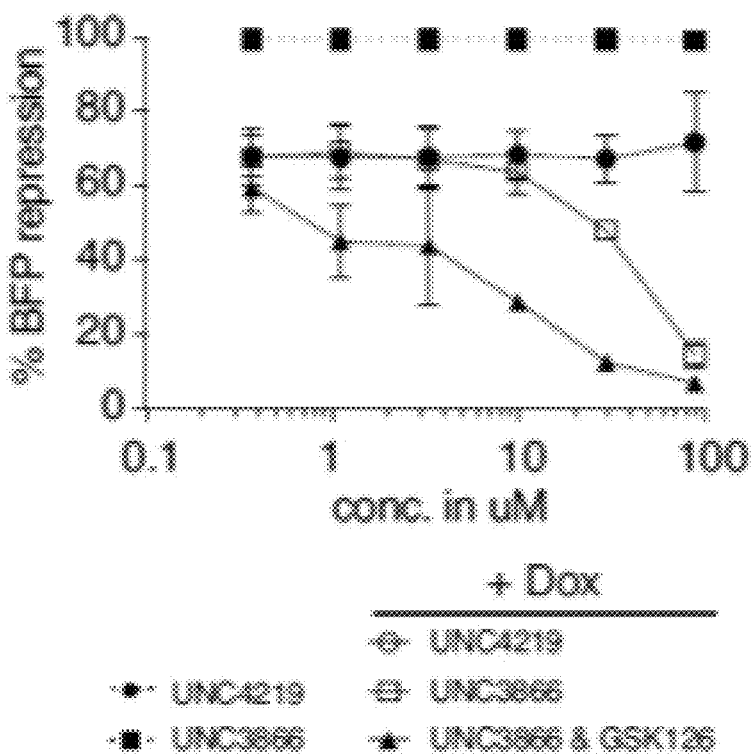
Figure 10B:
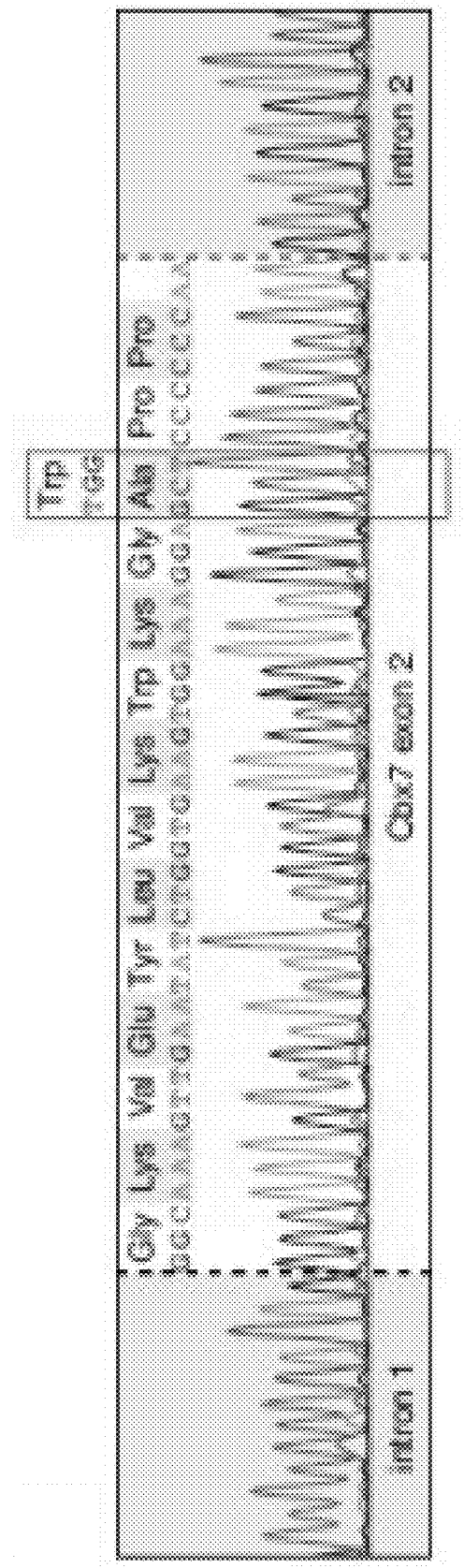

To determine if heritable gene silencing requires H3K27me3, we utilized a selective inhibitor of the histone methyltransferase Ezh2, GSK126, which blocks catalytic activity dose-dependently without affecting the overall integrity of the PRC2 complex (McCabe et al., Nature. 492, 108-112 (2012)). Indeed, in GSK126-treated parental mESCs H3K27me3 was undetectable by Western blot (FIG. 10A). Importantly, inhibitor treatment did not disrupt initiation of GFP reporter silencing in the context of TetR-Cbx7 tethering. In contrast, maintenance of reporter gene silencing was reduced by GSK126-treatment in a dose-dependent manner (FIG. 4B). Further, the GSK126-mediated reduction in silencing was more prominent at the distal BFP reporter than the proximal GFP promoter. Thus, H3K27me promotes heritable propagation of cPRC1 targeting in cis (FIG. 4B).

The chromodomain of Cbx7 displays affinity for H3K9me3 and H3K27me3 (Bernstein et al., *Molecular and Cellular Biology.* 26, 2560-2569 (2006)). To determine if this interaction is involved in maintenance of reporter gene repression, we transduced TetO-mESCs with a TetR-Cbx7 mutant encoding a loss-of-function amino acid substitution in the aromatic cage responsible for binding methylated histone (Cbx7$^{wt}$/TetR-Cbx7$^{W35A}$). In addition, we expressed the TetR-Cbx7$^{W35}$A mutant in TetO-mESCs whose endogenous Cbx7 genes harbour the same mutation (Cbx7$^{W35}$A/TetR-Cbx7$^{W35A}$, FIG. 10B). TetR-Cbx7$^{W35}$A was sufficient to initiate repression of the dual reporter locus in wildtype and Cbx7$^{W35}$A TetO-mESCs (FIG. 4C). However, upon Dox treatment, both wildtype and mutant reporter cells failed to maintain repression of GFP. Together, these results suggest that Cbx7 binding to methylated histones via its chromodomain is critical for maintaining gene silencing.

Example 6: Inhibitor Testing

Figure 4D:
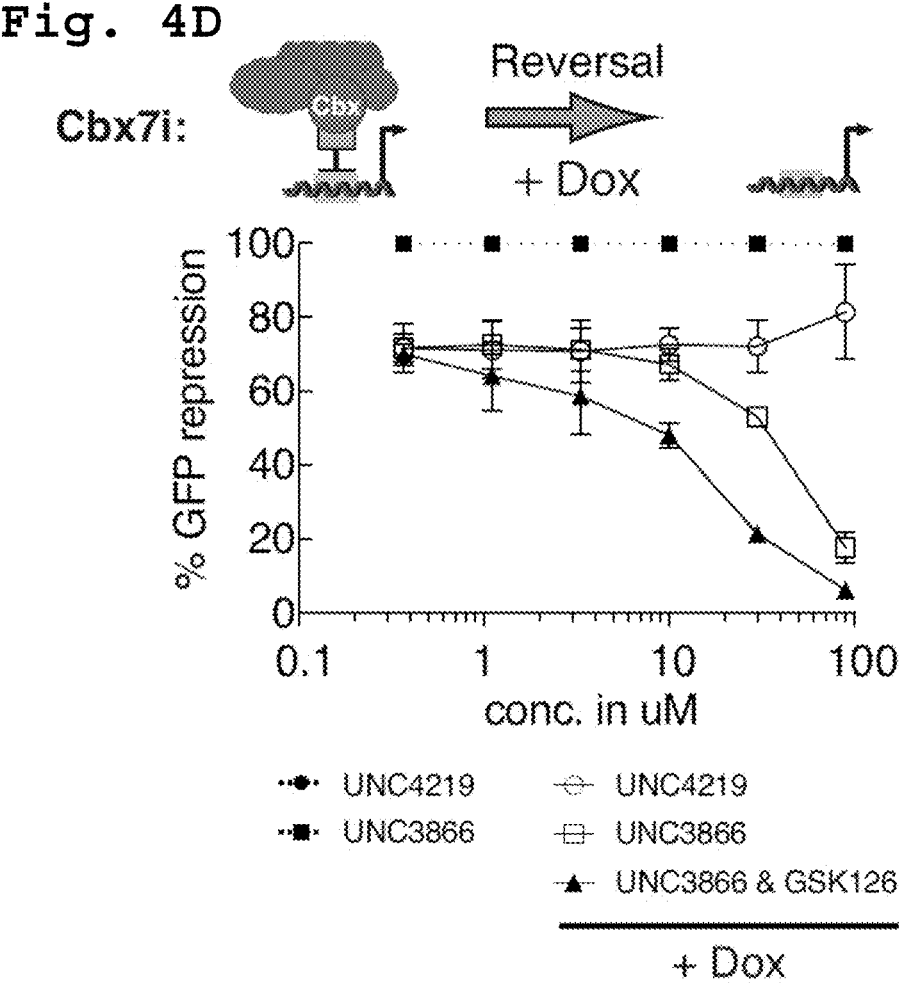
Figure 10C:
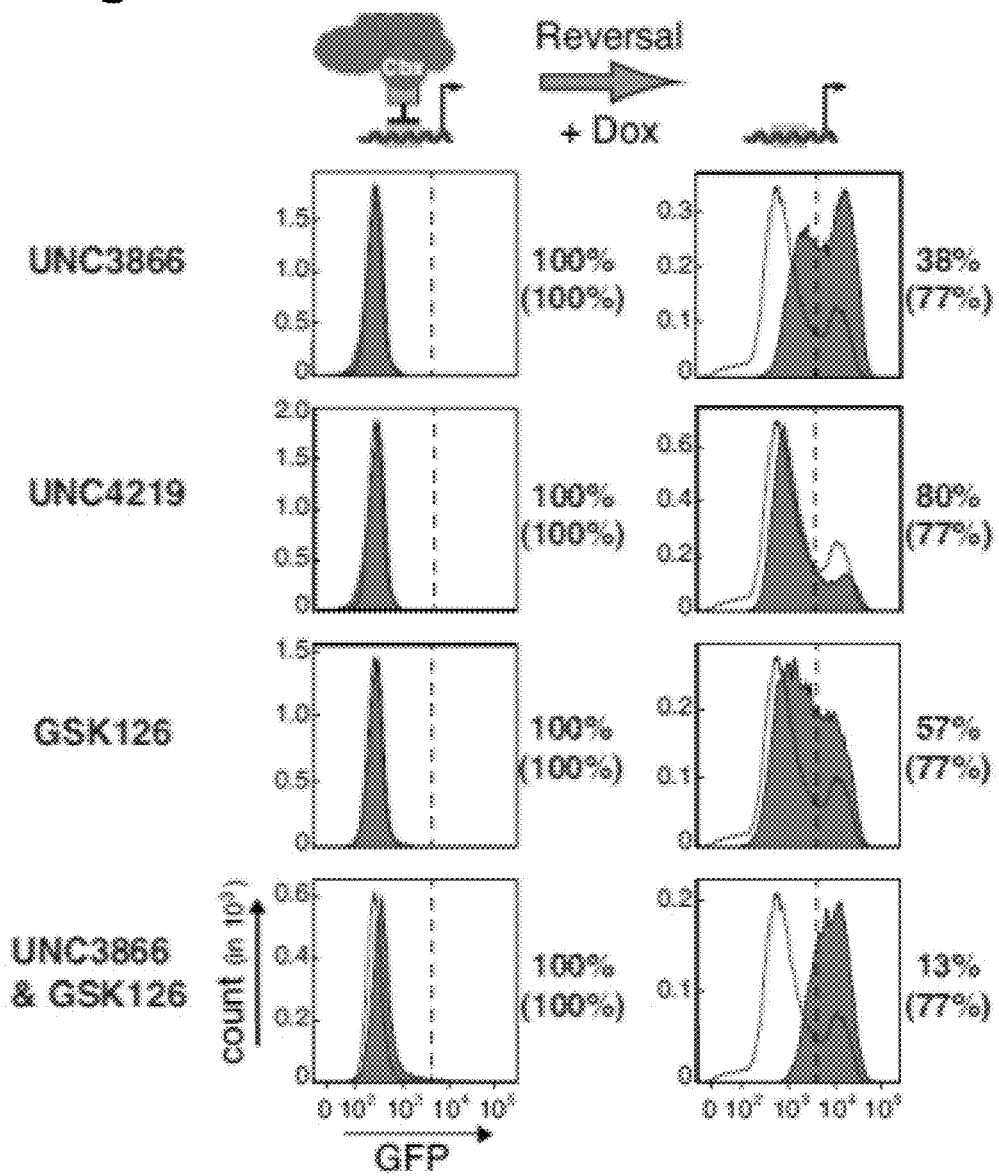

To validate this finding, we utilized the PRC1 inhibitor UNC3866, which selectively binds to Cbx4/7 and disrupts the interaction with methylated histones (Stuckey et al., *Nature Chemical Biology.* 12, 180-187 (2016)). CPRC1-TetO-mESCs were treated with either the Cbx7 antagonist UNC3866 or the negative control compound UNC4219, both in absence and presence of Dox. Neither compound had a significant effect on the initiation of reporter gene silencing, similar to the Cbx7$^{W35}$A mutant (FIG. 4D and FIGS. 10C and D). In the presence of Dox, maintenance of repression was disrupted only by UNC3866 treatment in a dose-dependent manner. In contrast, >70% of reporter cells treated with the control compound maintained GFP- and BFP repression. In line with Cbx7 interacting specifically with H3K27me3, failure to maintain gene repression was exacerbated by combined treatment with UNC3866 and GSK126 (FIGS. 4D and 10C and D).

To unequivocally rule out residual TetR initiation as a potential explanation for maintenance of PcG-dependent silencing in TetR-Cbx7 expressing reporter cells, we sought to reverse TetO recruitment by conditional genetic deletion of the TetR DNA binding domain within TetR-Cbx7. We transduced TetO-mESCs with TetR-Cbx7 or TetR-Rybp transgenes in which the sequence encoding the TetR DNA binding domain was fused to mCherry and flanked by loxP sites to enable Cre recombinase-mediated excision without disrupting the FLAG-Cbx7 or FLAG-Rybp coding sequences (FIG. 13a). TetR-dependent recruitment of Cbx7 and Rybp resulted in reporter gene silencing. Following Cre recombinase transfection, mCherry-negative cells were isolated by FACS and precise TetR domain deletion was confirmed by allele-specific PCR and Western blot (FIGS. 13b and c). Importantly, after genetic deletion of the TetR DNA binding domain, flow cytometry confirmed selective maintenance of reporter gene silencing in cPRC1-mESCs but not vPRC1-mESCs (FIG. 13d). Furthermore, Cbx7-dependent repression was abolished upon combined treatment with Cbx7i and Ezh2i, in agreement with the conclusion that persistent repression relies on H3K27me3 binding. These results demonstrate that cPRC1 can promote sequence-independent maintenance of PcG-dependent gene silencing. Moreover, Thus, disruption of the "reader function" of Cbx7, either via mutation or pharmacologic antagonism, abrogates sequence-independent targeting of canonical PRC1 after genome replication in mitotic cells. Hence, H3K27me3 recruits PRC2 and cPRC1 to promote epigenetic maintenance of PcG-dependent gene silencing.

Example 7: Recruitment of PRC2 and Canonical PRC1

Figure 4E:
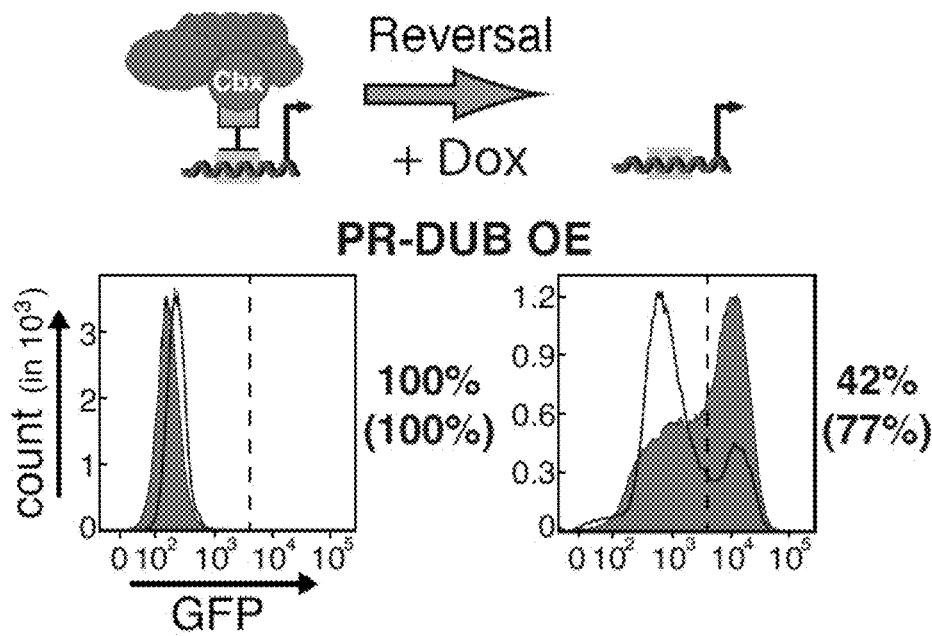
Figure 12E:
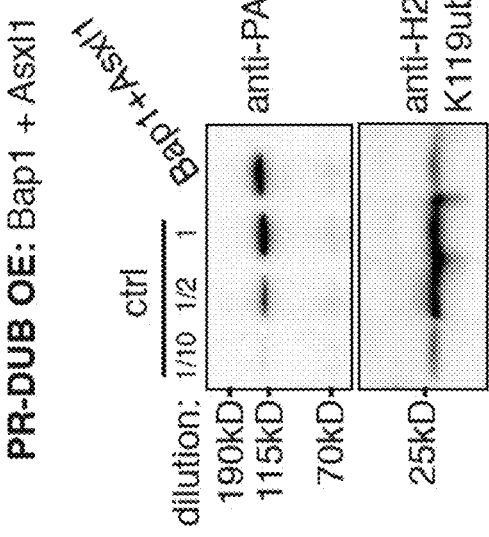
Figure 12G:
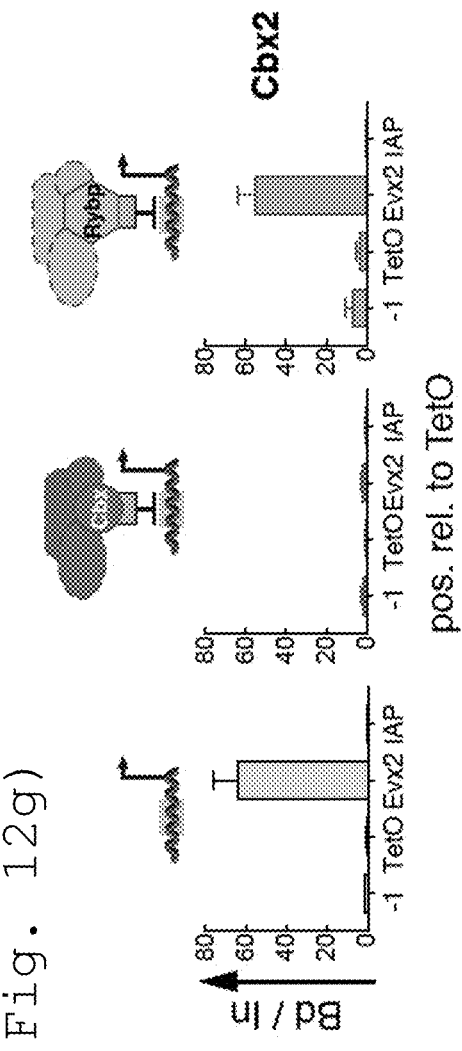

Our results suggest that PRC1 can promote PRC2 targeting (FIG. 1C). Indeed, Jarid2, an auxiliary component of PRC2, binds H2AK119ub1 (Cooper et al., *Nature Communications.* 7, 1-8 (2016)). H2AK119ub1 might also contribute by imposing gene repression, which otherwise would antagonize PRC2 activity (FIGS. 2B and 2C). To investigate the role of H2AK119ub1 in initiation and maintenance of cPRC1-mediated gene repression, we ectopically expressed Bap1 together with a truncated version of Asx11 (1-479 aa) to generate a hyperactive Polycomb Repressive-Deubiquitinase complex (DUB) in cPRC1-TetO-mESCs (FIG. 4E). Western blot analysis confirmed that DUB overexpression was sufficient to reduce total levels of H2K119ub1 (FIG. 12e). While bulk H2AK119ub1 reduction had a negligible effect on the initiation of gene silencing it significantly reduced maintenance of gene silencing (FIG. 4E and FIG. 12f), suggesting that H2AK119ub1 is important to recruit PRC2 and/or canonical PRC1 for epigenetic maintenance of cPRC1-initiated gene silencing.

Example 8: Cellular Pathways of Regulation

Figure 4F:
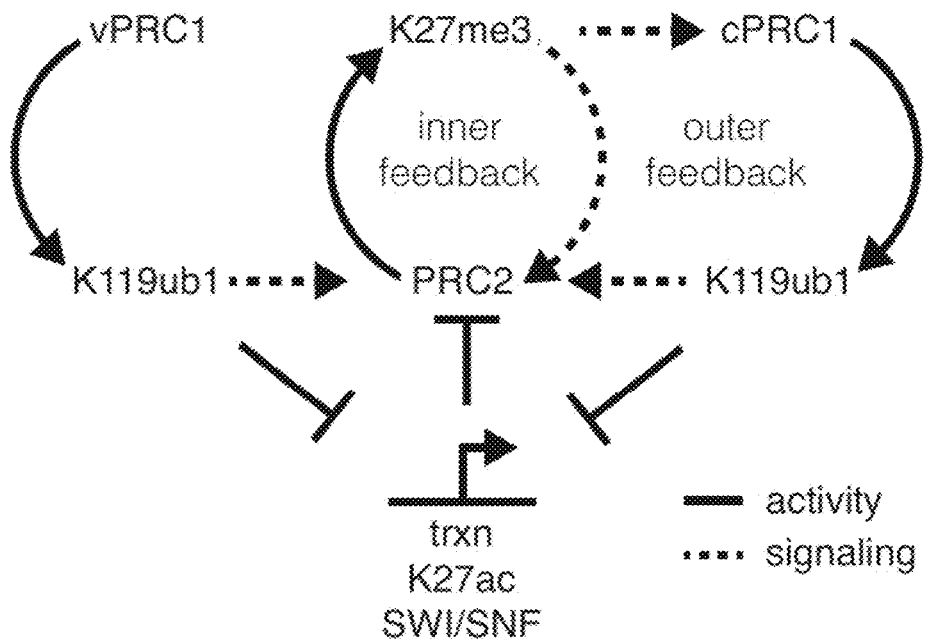

Together, our findings reveal non-redundant functions of the major vertebrate PcG complexes in initiation and maintenance of gene silencing. We demonstrate that Polycomb-dependent heritable gene repression is restricted to canonical PRC1 (FIG. 4F). In *Drosophila*, it was shown that transient tethering of Cbx homolog Pc was sufficient to establish gene silencing. Heritable maintenance required the presence of Polycomb Response Elements. There is little evidence for PREs in vertebrates arguing that in contrast to flies, canonical PRC1 mediates sequence-independent inheritance of gene repression by utilizing the positive feedback cycle between PRC2 and its catalytic output H3K27me3 (FIG. 4F). Notably, in the context of transcriptional antagonism, self-reinforcement of H3K27me3 requires feedback by cPRC1 activity ensuring robust repression and H2AK119ub1 to promote further PRC2 recruitment. Similar to its canonical counterpart, repressive chromatin-modifying activities of variant PRC1 can induce gene silencing. However, this silencing pathway lacks a feedback mechanism to promote epigenetic maintenance (FIG. 4F). Hence, variant PRC1 enforces a more dynamic mode of gene repression. We assume that the diversification of PRC1 complexes has allowed vertebrates to evolve a large repertoire of different chromatin regulatory mechanisms for fine-tuning gene repression in response to the increased complexity of intrinsic and extrinsic stimuli.

Example 9: Position Effect Variegation

In FIG. 13, we show selected representative examples to highlight the importance of inserting the landing site and reporter gene at genomic loci with well-defined chromatin modification states. FIGS. 13a) and b) demonstrate a variegated GFP expression pattern is linked to single insertions of the reporter gene in proximity of heterochromatic chromatin modifications including H3K9me3. As a result of predisposed reporter gene silencing, the transcriptional control of the chromatin in vivo assay will be compromised and the dynamic range of GFP signal is reduced. By comparison, FIGS. 13 c) and d) show that reporter gene insertion in proximity of active genes marked with H3K4me3 can promote GFP expression. In turn, "open" chromatin environment impacts the ability of induced transcriptional repression in response to tethering of chromatin modifiers to the landing site upstream of the reporter gene.

As shown in FIG. 14, we demonstrate the impact of an open, gene-rich chromatin environment on the ability of TetR fusions with Eed and Ezh2 (PRC2 core components) to induce reporter gene repression. FIG. 14 b)-d) show histone modifications and RNA expression at reporter gene insertion sites on chromosomes 1, 7 and 15. Flow cytometry shows GFP expression before and after expression of TetR fusions with Eed and Ezh2 (FIG. 14 e). Both fusion proteins can induce transcriptional repression of TetO reporter genes inserted in "naïve" chromatin environments on chromosomes 1 and 7. In contrast, only TetR-Ezh2, but not TetR-Eed, can nucleate repressive chromatin modifications at the insertion site on chromosome 15 which is proximal to active genes and "open" chromatin as marked by H3K4me3.

The problem of Position-Effect-Variegation affecting the expression of the reporter gene as well as the transgene encoding the effector fusion protein is further highlighted in FIG. 15. Partial repression of the reporter gene and heterogeneous transgene expression in the infected population severely limits the dynamic range and sensitivity of the reporter assay. We directly compare the GFP readout of a two clonal reporter cell lines before and after tethering of different PcG fusion proteins. Clonal mESC line with random insertion of reporter gene shows variegated GFP expression (FIG. 15 a, c). Clonal mESC line with known reporter insertion on chromosome 1 in chromatin that lack active and repressive histone modifications (FIG. 15 b, d). Transduced population of reporter cell line in a) with TetR fusions of Cbx7, Rybp and Eed in a population with heterogenous expression of transgene due to multiple random integrations shows variable degree of repression in response to tethering of the respective PcG protein (FIG. 15 c), whereas individual clones of reporter cell line in expressing TetR fusions with Cbx7, Rybp and Eed as single defined insertions show distinct on-off behaviours (FIG. 15 d).

The invention claimed is:

1. A method of detecting Polycomb Repressive Complex (PRC) activity in a vertebrate cell, the method comprising the step of providing vertebrate cells with a DNA having a protein binding site and at least one reporter gene expression site that is operatively connected to said protein binding site, wherein said protein binding site is located at a transcriptionally neutral locus or region of the genome of the vertebrate cells, wherein the transcriptionally neutral locus or region lacks active and repressive histone modifications, and the vertebrate cells comprise a DNA comprising a recombinant gene of a binding protein, said binding protein being capable of binding to said protein binding site, wherein said binding protein is fused to a member of the PRC, said method further comprising the steps of expressing said recombinant gene, letting said fused binding protein bind to said protein binding site and detecting at least one reporter gene expression.

2. The method of claim 1, wherein an operatively connected reporter gene expression site is within a distance of 12 kb in length from said protein binding site.

3. The method of claim 1, wherein the at least one reporter gene expression site comprises at least two reporter gene expression sites.

4. The method of claim 3, where the at least two reporter gene expression sites comprise a first reporter gene expression site within a distance from said protein binding site that is less than two thirds the distance of a second reporter gene expression site.

5. The method of claim 1, wherein the at least one reporter gene expression site comprises a nucleic acid encoding a fluorescent protein.

6. The method of claim 1, further comprising contacting one of the provided vertebrate cells with a candidate compound, wherein the at least one reporter gene expression detected is compared to at that least one reporter gene expression in another of the provided vertebrate cells that is not contacted with the candidate compound.

7. The method of claim 1, wherein the member of the PRC that is fused to the binding protein is selected from Cbx7, Rybp, Eed, Ring1a, Ring1b, PCGF1, PCGF2, PCGF3, PCGF4, PCGF5, PCGF6.

8. The method of claim 1, wherein the protein binding site is an inducible binding site.

9. The method of claim 8, wherein detecting at least one reporter gene expression is compared between induction and non-induction of the binding site.

10. The method of claim 1, wherein the protein binding site is a TetO site.

11. The method of claim 1, wherein the protein binding site is a zinc finger binding site and said binding protein comprises a zinc finger motif capable of binding to said zinc finger binding site.

12. The method of claim 1, wherein the vertebrate cells comprises only one copy of the reporter gene expression site that is operatively connected to said protein binding site.

13. The method of claim 1, wherein the transcriptionally neutral locus or region lacks an active histone modification and repressive histone modifications within 30000 nt of the protein binding site and the reporter gene.

14. The method of claim 13, wherein the active histone modification is H3K4 methylation and/or the repressive histone modifications are H3K27 methylation and H3K9 methylation.

15. A kit comprising: a) a vertebrate cell with a DNA having a protein binding site, wherein said protein binding site is located at a transcriptionally neutral locus or region of the genome of the vertebrate cell, wherein the transcriptionally neutral locus or region lacks active and repressive histone modifications, and the DNA further comprising at least one reporter gene expression site operatively connected to said protein binding site; said kit further comprises b) a DNA vector with a recombinant gene of a binding protein; said binding protein being capable of binding to said protein binding site, wherein said binding protein is fused to a member of a Polycomb Repressive Complex (PRC).

16. A method of generating a vertebrate cell usable in a method of claim 1, comprising providing a kit comprising: a1) a vertebrate cell with a DNA having a protein binding site, wherein said protein binding site is located at a transcriptionally neutral locus or region of the genome of the vertebrate cell, wherein the transcriptionally neutral locus or region lacks active and repressive histone modifications, and the DNA further comprising at least one reporter gene expression site operatively connected to said protein binding site or a2) a DNA vector for site specific integration into a transcriptionally neutral locus or region of the genome of a vertebrate cell, wherein the transcriptionally neutral locus or region lacks active and repressive histone modifications, the DNA vector having a protein binding site and at least one reporter gene expression site that is operatively connected to said protein binding site; said kit further comprises b) a DNA vector with a recombinant gene of a binding protein, said binding protein being capable of binding to said protein binding site, wherein said binding protein is fused to a member of a Polycomb Repressive Complex (PRC);
and introducing the vector b) into the vertebrate cell of a1) or introducing the vectors of a2) and b) into a vertebrate cell.

17. A vertebrate cell comprising: a DNA having a protein binding site and at least one reporter gene expression site that is operatively connected to said protein binding site; wherein said protein binding site is located at a transcriptionally neutral locus or region of the genome of the vertebrate cell, wherein the transcriptionally neutral locus or region lacks active and repressive histone modifications; and further comprising a DNA comprising a recombinant gene of a binding protein; said binding protein being capable of binding to said protein binding site, wherein said binding protein is fused to a member of a Polycomb Repressive Complex (PRC).

18. The method of claim 1, wherein the PRC is selected from variant PRC1, canonical PRC1 and PRC2.

19. The method of claim 3, wherein the at least one reporter gene expression site comprises two or more different reporter genes.

20. The method of claim 5, wherein the fluorescent protein is selected from GFP, CFP, YFP, drFP583, BFP, smURFP; and/or luciferase.

21. The method of claim 8, wherein the protein binding site is an inducible binding site, with an induction of binding being mediated by the presence of a binding co-factor or a binding disruptor.

22. The method of claim 21, wherein the inducible binding site is a TetO site, the binding protein is Tet repressor or tTA, and the binding disruptor is tetracycline or doxycycline.

23. The method of claim 12, wherein the vertebrate cells comprise only one copy of the reporter gene expression site that is operatively connected to said protein binding site integrated into the genome of the vertebrate cells.

24. The method of claim 1, wherein the member of the PRC that is fused to the binding protein is selected from Cbx7, Rybp, Eed, PCGF1, PCGF2, PCGF3, PCGF4, PCGF5, PCGF6, Ring1a, Ring1b, EZH1, EZH2, RBBP4, RBBP7, SUZ12, JARID2, AEBP, Epop, CBX2, CBX4, CBX6, CBX8, PHC1, PHC2, PHC3, AUTS2, BCL-6, ASXL1, ASXL2, BAP1, and OGT1.

25. The method of claim 1, where the vertebrate cells are mammalian cells.

* * * * *